(12) United States Patent
Fahrni et al.

(10) Patent No.: US 11,604,141 B2
(45) Date of Patent: Mar. 14, 2023

(54) ZINC-SELECTIVE FLUORESCENT PROBES FOR EMISSION-RATIOMETRIC IMAGING

(71) Applicant: Georgia Tech Research Corporation, Atlanta, GA (US)

(72) Inventors: Christoph J. Fahrni, Atlanta, GA (US); Adam M. McCallum, Atlanta, GA (US); Michael Thomas Morgan, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 136 days.

(21) Appl. No.: 16/619,620

(22) PCT Filed: Jun. 12, 2018

(86) PCT No.: PCT/US2018/037125
§ 371 (c)(1),
(2) Date: Dec. 5, 2019

(87) PCT Pub. No.: WO2018/231843
PCT Pub. Date: Dec. 20, 2018

(65) Prior Publication Data
US 2020/0158735 A1    May 21, 2020

Related U.S. Application Data

(60) Provisional application No. 62/518,250, filed on Jun. 12, 2017.

(51) Int. Cl.
*G01N 21/64* (2006.01)
*C07D 417/04* (2006.01)
(Continued)

(52) U.S. Cl.
CPC ....... *G01N 21/6428* (2013.01); *C07D 417/04* (2013.01); *C07D 417/14* (2013.01);
(Continued)

(58) Field of Classification Search
CPC .... G01N 33/1813; G01N 31/22; G01N 33/52; G01N 21/6428; G01N 21/77;
(Continued)

(56) References Cited

U.S. PATENT DOCUMENTS

2014/0080168 A1   3/2014  Pang et al.
2014/0134665 A1*  5/2014  Que ...................... A61K 31/40
                                                          435/29

FOREIGN PATENT DOCUMENTS

CN   104610139   5/2015
CN   105859706   8/2016
WO   2007/013201  2/2007
WO   2016/128103  8/2016

OTHER PUBLICATIONS

Sumalekshmy, S. et al. "Design of Emission Ratiometric Metal-Ion Sensors with Enhanced Two-Photon Cross Section and Brightness," J. Am. Chem. Soc. 2007, 129, 39, 11888-11889, including Supporting Information. (Year: 2007).*

(Continued)

*Primary Examiner* — Jennifer Wecker
*Assistant Examiner* — Michelle Adams
(74) *Attorney, Agent, or Firm* — Troutman Pepper Hamilton Sanders LLP; Ryan A. Schneider; Sarah M L Wilkening

(57) ABSTRACT

The compounds relate to zinc-sensitive fluorescent probes, compositions and methods utilizing the same. Such compounds provide an emission-ratiometric fluorescence response upon binding of an analyte. In some embodiments, compounds can be used for two-photon excitation microscopy or conventional fluorescence microscopy. The compounds described herein can also contain one or more functional groups to improve the emission-ratiometric fluorescence response.

15 Claims, 45 Drawing Sheets

(51) Int. Cl.
*C07D 417/14* (2006.01)
*G01N 21/77* (2006.01)
*G01N 33/58* (2006.01)
*A61K 49/00* (2006.01)

(52) U.S. Cl.
CPC .......... *G01N 21/77* (2013.01); *G01N 33/582* (2013.01); *A61K 49/0021* (2013.01); *G01N 2021/6439* (2013.01); *G01N 2021/7786* (2013.01)

(58) Field of Classification Search
CPC ......... G01N 33/582; G01N 2021/6439; G01N 2021/7786; C07D 417/04; C07D 417/14; A61K 49/0021
USPC .......................................................... 436/81
See application file for complete search history.

(56) References Cited

OTHER PUBLICATIONS

Hüttinger, Karl J. Semi-Synthetic Proteins for Catalytic and Analytical Applications. Georgia Institute of Technology, May 2009. Doctoral Thesis. Published by ProQuest, 2010 (Year: 2010).*
Dalle, K.E. et al. "Ligand modifications modulate the mechanism of binuclear phosphatase biomimetics," Polyhedron 52 (2013) 1336-1343 (Year: 2013).*
Siegel, Nisan Naftali. Two-Photon Absorption in Cruciform and Dipolar Chromophores: Excitonic Interactions and Response to Metal Ions. Georgia Institute of Technology, Aug. 2010. Doctoral Dissertation. Published by ProQuest, 2011. (Year: 2011).*
International Search Report and Written Opinion from Application No. PCT/US2018/037125 dated Aug. 10, 2018 (7 pages).
1-Phenyl-N-(pyridin-2-ylmethyl) methanamine, PUBCHEM.CID 795879, Jul. 2005 (pp. 1-16).

* cited by examiner $^1$H NMR (DMSO-d6, 400 MHz)

$^{13}$C NMR (DMSO-d6, 100 MHz)

¹H NMR (DMSO-d6, 400 MHz)

<sup></sup>13C NMR (DMSO-d6, 100 MHz)

¹H NMR (CDCl₃, 400 MHz)

¹³C NMR (CDCl₃, 100 MHz)

¹H NMR (MeOD, 400 MHz)

$^{13}$C NMR (MeOD, 100 MHz)

¹H NMR (CDCl₃, 400 MHz)

$^{13}$C NMR (CDCl$_3$, 100 MHz)

$^1$H NMR (CDCl$_3$, 400 MHz)

<sup>13</sup>C NMR (CDCl$_3$, 100 MHz)

$^1$H NMR (CDCl$_3$, 400 MHz)

$^{13}$C NMR (CDCl$_3$, 100 MHz)

Figure 24
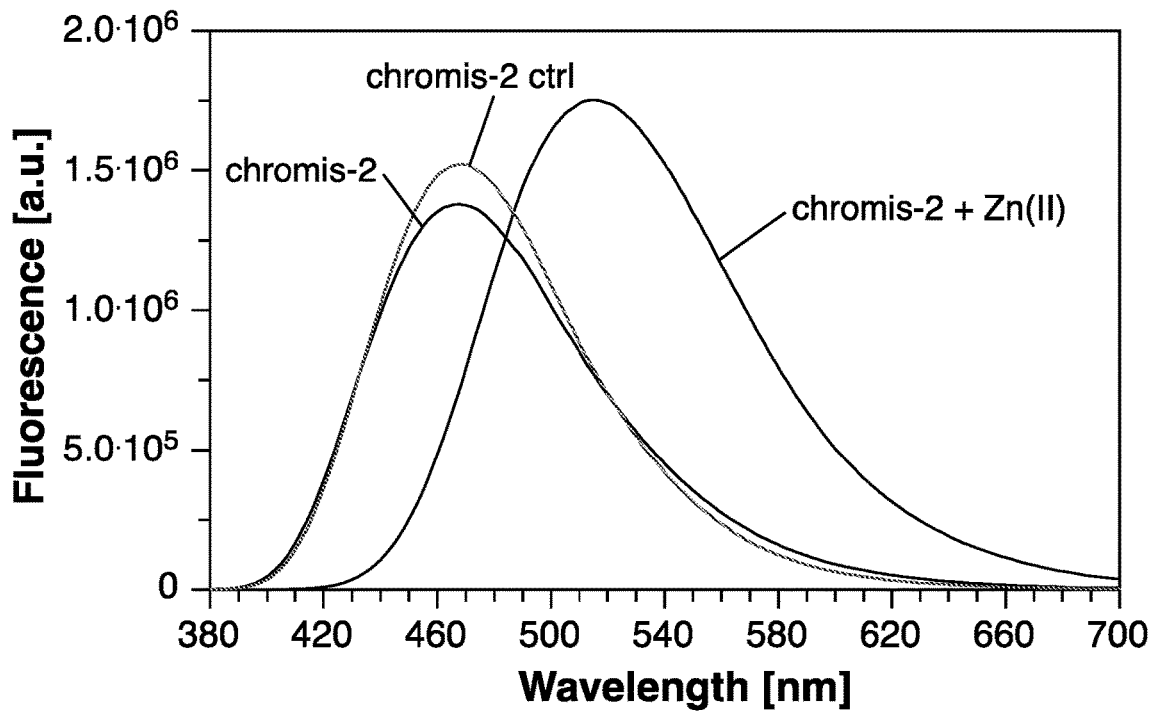
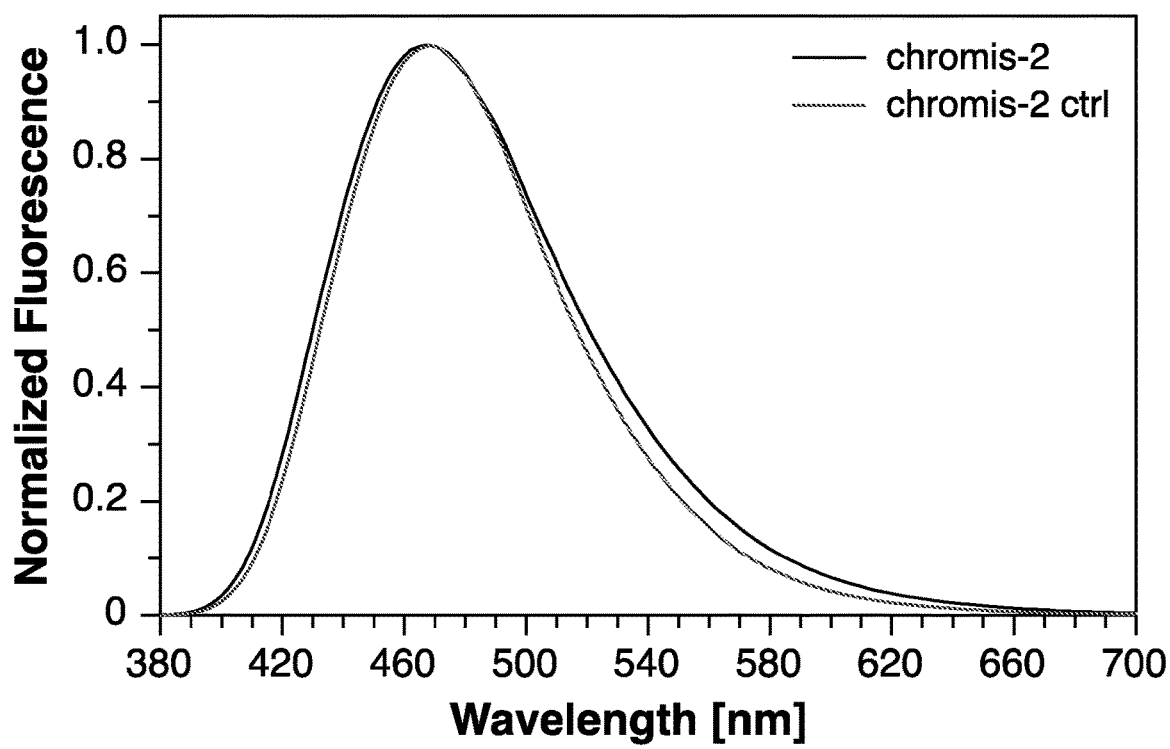

ZINC-SELECTIVE FLUORESCENT PROBES FOR EMISSION-RATIOMETRIC IMAGING

CROSS-REFERENCE TO RELATED APPLICATIONS

This application, filed 12 Jun. 2018, claims the benefit of U.S. Provisional Patent Application No. 62/518,250, filed 12 Jun. 2017, entitled "Zinc-Selective Fluorescent Probes for Emission-Ratiometric Imaging" the entire contents and substance of which are hereby incorporated by reference as if fully set forth below.

GOVERNMENT SPONSORSHIP

This invention was made with government support under Grant No. CHE-1306943 awarded by the National Science Foundation (NSF). The government has certain rights in the invention.

TECHNICAL FIELD

Embodiments of the present disclosure relate to zinc-sensitive fluorescent probes, compositions and methods utilizing the same and in particular to emission-ratiometric fluorescent compounds which can be used in two-photo excitation microscopy (TPEM) or conventional fluorescence microscopy and can be suitable for the selective detection of labile Zn(II) pools in various sample such as live cells, tissues, and whole organisms.

BACKGROUND OF THE INVENTION

Zinc (Zn) is an essential trace nutrient required for the vitality of all living organisms. It plays a central role in major cellular processes, including gene regulation, protein synthesis, and metabolic pathways. Cell development and proliferation critically depend on the presence of zinc ions. For example, the requirements for zinc are increased during pregnancy and lactation and hence critical to growth and development of the fetus and neonate. Zinc also plays also an important role in bone metabolism and is essential for the normal development of the skeleton in humans and animals. The availability of zinc generally affects processes that involve rapid proliferation, such as wound healing, angiogenesis, and tumor growth. At the cellular level, zinc deprivation inhibits proliferation via cell cycle arrest at the late G1 phase as well as the G2/M transition, and blocks progression past telophase I of the meiotic cell cycle. Conversely, zinc supplementation promotes proliferation of healthy mouse cells as well as tumor cells.

Despite the importance of zinc in biology, mechanisms governing zinc regulation and redistribution within cells, tissues, or whole organisms remain largely unexplored. Progress has been hampered in part due to the challenges associated with quantifying the distribution of zinc in situ. The total concentration of Zn in eukaryotic cells lies in the high micromolar to low millimolar range, which corresponds to 108-109 atoms per cell. Regulated through an intricate network of Zn-selective membrane transporters, cells are capable of maintaining intracellular Zn levels approximately two orders of magnitude higher compared to the extracellular environment. While the majority of intracellular Zn is bound to proteins, either as catalytic or structural component, cells also maintain a labile subpool that can readily exchange with exogenous chelators. According to measurements with a range of synthetic and genetically encoded fluorescent probes, this labile cytosolic Zn pool is buffered at picomolar to low nanomolar concentrations.

Several modern microanalytical techniques, notably secondary ion mass spectrometry, nuclear microprobes, and synchrotron x-ray fluorescence microscopy (microXRF), offer much improved detection limits compared to traditional methods such as inductively coupled plasma mass spectrometry and are also capable of quantifying trace metal within single cells with submicron spatial resolution. However, these methods can report only on total trace metal levels and are not suitable for analyzing dynamic changes in live cells. Ratiometric fluorescent probes represent a complementary tool for visualizing and quantifying dynamic changes of labile trace metal levels in live cells, tissues, or whole organisms.

Because biological samples are often extremely delicate and sensitive, the use of high energy lasers with which confocal microscopes are equipped can pose deleterious effects, such as phototoxicity and photobleaching, that are manifested as a result of applying fluorescent probes in cells. Two-photon excitation microscopy (TPEM) can be employed in detection and quantification methods because compared to conventional fluorescence microscopy, TPEM offers multiple advantages, including reduced photo toxicity, increased depth penetration, and negligible background fluorescence, thus making it a superior method for prolonged in vivo imaging studies. Relying on a single Ti-sapphire femtosecond-pulsed laser as excitation source, ratiometric TPEM requires fluorescent probes that respond with a spectral shift of the emission rather than excitation profile upon analyte binding, a requirement that is currently not met by most ratiometric indicators.

BRIEF SUMMARY

An embodiment of the present disclosure can be a compound according to Formula I:
wherein Z can be:

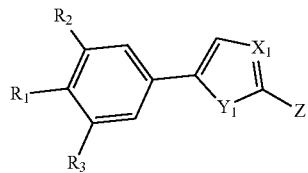

Formula I

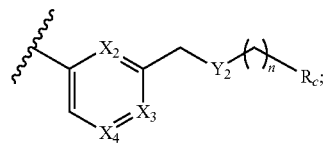

$X_1$, $X_2$, $X_3$, and $X_4$ can be each independently selected from —N and —CH; $Y_1$ can be selected from —NR$_4$, —S—, and —O; $Y_2$ can be selected from —NR$_5$, —S—, and —O; $R_e$ can be Ar, —OR$_4$, —N(CH$_2$)$_q$—Ar)$_2$; $R_1$, $R_2$, $R_3$, and $R_4$ can be each independently selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl; or $R_1$ and $R_2$; or $R_1$ and $R_3$ may together form a moiety selected from cycloalkyl, cycloalkenyl, aryl, heterocycloalkyl, heterocycloalkenyl, and heteroaryl; $R_5$ can be selected from Cr-alkyl optionally substituted with —$OR_4$ or Ar; and Ar can be independently at each occurrence selected from aryl and heteroaryl; n can be 1, 2, or 3; q can be 1, 2, or 3 and wherein any one of the aforementioned can be substituted or unsubstituted.

An embodiment of the present disclosure can be a method of detecting zinc in a sample comprising the steps of: (1) treating the sample with the compound of Formula I; (2) detecting a light emission from the compound of Formula I, the light emission comprising a first wavelength emission and a second wavelength emission, wherein the first wavelength emission intensity is associated with an unbound compound of Formula I and the second wavelength emission intensity is associated with a zinc-bound compound of Formula I; and (3) comparing the first wavelength emission intensity to the second wavelength emission intensity to determine the concentration of zinc in the sample.

BRIEF DESCRIPTION OF THE DRAWINGS

(FIG. 1A) Buffer isotope effect on the fluorescence intensity and shape of compound 1. (FIG. 1B) Normalization of fluorescence spectra of compound 1 shown in (FIG. 1A). (FIG. 1C) Buffer isotope effect on the fluorescence intensity and shape of compound 2.

(FIG. 2A) Measurement of fluorescence intensity of 3b in deuterated and non-deuterated aqueous buffer (10 mM PIPES, 0.1 M KCl, pH/D 7.0, 25° C.). (FIG. 2B) Overlay of the comparison between chromis-2 and 3b in deuterated and non-deuterated aqueous buffer, demonstrating the increase in quantum yield of free and Zn(II)-saturated chromis-2.

(FIG. 3A) Synthetic scheme of chromis-2. (FIG. 3B) ORTEP representation and atomic numbering for the crystal structure of the chromis-2-Zn(II) complex [(4) Zn(II)]. The ellipsoids shown represent 50% probability. Hydrogen atoms, counter ions, and additional solvent molecules have been omitted for clarity.

(FIG. 4A) Absorption spectral changes with chromis-2 (10 µM) upon incremental saturation of Zn(II) in aqueous buffer (10 mM PIPES, 0.1 M KCl, pH 7.0, 25° C.). (FIG. 4B) Fluorescence spectral changes with chromis-2 (10 µM) upon incremental saturation of Zn(II). (FIG. 4C) Emission-ratiometric response to biologically relevant divalent metal cations at 80% fractional saturation (calculated based on ratio of the integrated fluorescence intensity between 510-570 nm and 440-495 nm (excitation at 361 nm).

FIG. 16A-16H) Black traces represent free compound 3b (5 µM) in pH 7.0 buffer (10 mM PIPES, 0.1 M KCl, 25° C.) supplemented with 10 µM EDTA. Red and blue traces represent the addition of 20 µM and 40 µM, respectively, of interfering divalent metals. Excitation: 361 nm.

(FIG. 17A-17H) Black (dashed) traces represent free compound 3b (5 µM) in pH 7.0 buffer (10 mM PIPES, 0.1 M KCl, 25° C.) supplemented with 10 µM EDTA, black (solid) traces represent the subsequent addition of interfering metal ions, and red traces represent saturation of the remaining 20% probe with Zn(II). Excitation: 361 nm.

(FIG. 19A) Spectrophotometric titration of [(compound 4)Zn(II)] with EGTA as the competing ligand in pH 7.0 buffer (10 mM PIPES, 0.1 M KCl, 25° C.). The red trace represents the Zn(II)-saturated ligand before addition of EGTA. (FIG. 19B) Non-linear least-squares fitting of the absorbance data, showing the change in absorbance and corresponding fit at 530 nm. Fitting the absorbance data over the entire spectral window (250-500 nm) yielded an average Log $K_{Zn(II)L}=7.97\pm0.03$ (n=2).

FIG. 20A-20H) Black traces represent free chromis-2 (5 μM) in pH 7.0 buffer (10 mM PIPES, 0.1 M KCl, 25° C.) supplemented with 10 μM EDTA. Red and blue traces represent the addition of 20 μM and 40 μM, respectively, of interfering divalent metals. Excitation: 361 nm.

FIG. 21A-21H) Black (dashed) traces represent free chromis-2 (5 μM) in pH 7.0 buffer (10 mM PIPES, 0.1 M KCl, 25° C.) supplemented with 10 μM EDTA, black (solid) traces represent the subsequent addition of interfering metal ions, and red traces represent saturation of the remaining 20% probe with Zn(II). Excitation: 361 nm.

(FIG. 22A) Fluorimetric titration of chromis-2 with $MnSO_4$ $H_2O$ in pH 7.0 aqueous buffer (10 mM PIPES, 0.1 M KCl, 25° C.). The red trace represents free chromis-2 before addition of Mn(II). (FIG. 22B) Non-linear least-squares fitting of the absorbance data, showing the change in fluorescence and corresponding fit at 465 nm. Fitting the absorbance data over the entire spectral window (250-500 nm) yielded an average Log $K_{Zn(II)L}=7.97\pm0.03$ (n=2).

FIG. 24. Spectral comparison between chromis-2 compound (4) and chromis-2 ctrl (compound 4a).

(FIG. 25A) Left: Phase contrast image (DIC) and fluorescence intensity images acquired with 425-462 nm (BP1) and 478-540 nm (BP2) bandpass filters, respectively. Right: Intensity ratio image with R=BP2/BP1. (FIG. 25B) Left: Ratio images (BP2/BP1) prior (at 3 min) and after addition of 50 μM $ZnSO_4$ and 5 μM pyrithione (at 9 min). Further addition of 100 μM TPEN at 10 min resulted in a reversal of the intensity ratio (shown at 16 min). Right: Time course of the average intensity ratio change for the ROI indicated with a white circle in the left panel. The asterisks indicate time points for the respective ratio images shown to the left. Scale bars: 40 μm.

DETAILED DESCRIPTION

Figure 1A:
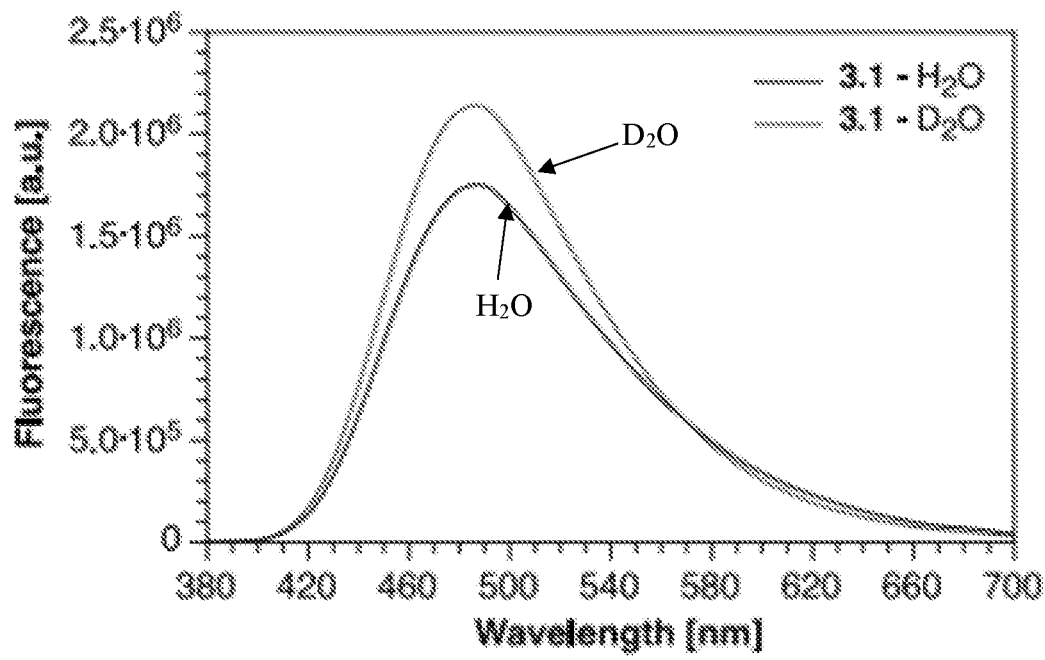
FIG. 1A-1C. Comparison of fluorescence emission spectra of compounds 1 and 2 (10 µM) in deuterated and non-deuterated buffer (10 mM PIPES, 0.1 M KCl, pH/D 7.0, 25° C.).

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Embodiments of the present disclosure can comprise Zn(II)-responsive fluorescent probes, which can generally comprise a donor-π-acceptor design, where the analyte (e.g., the Zn ion) can coordinate to the acceptor moiety rather than the donor moiety. Without wishing to be bound by theory, it is thought that this design strategy can allow bathochromic shifts (e.g., a red shift to a longer wavelength) in both the absorption and emission by inducing an increased intramolecular charge transfer upon photoexcitation when the metal analyte (e.g., Zn(II)) is bound. In some embodiments, the probe can be a 3-unit scaffold comprising: (1) an aryl ring system moiety; (2) a pi-bridge moiety; and (3) a Zn-chelator moiety. The probe can be of general Formula A-B-C, wherein "A" represents the aryl ring system moiety, "B" represents the pi-bridge moiety, and "C" represents the Zn-chelator moiety. Accordingly, in some embodiments, the probe can be represented by the structure:

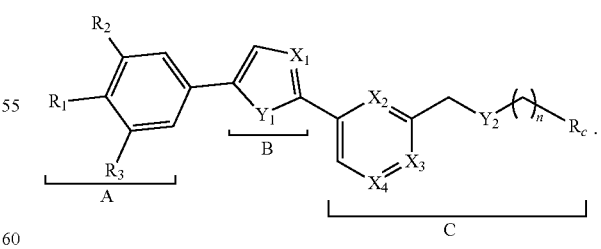

Component A: Aryl Ring System Moiety

Component A can generally comprise any aryl moiety that imparts electron-donating properties and allows for further functionalization, e.g. to enhance water-solubility or to attach a linker for conjugation to a biomolecule. In an embodiment, Component A can be selected from a substituted or unsubstituted aryl and a substituted or unsubstituted heteroaryl. In some embodiments, Component A can have the structure:

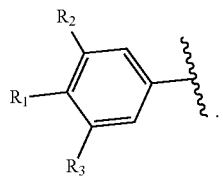

In some embodiments, $R_1$, $R_2$, and $R_3$ can be each independently selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl. In some embodiments, Component A can comprise a fused ring system, for example, $R_1$ and $R_2$; or $R_1$ and $R_3$ can together form a moiety selected from cycloalkyl, cycloalkenyl, aryl, heterocycloalkyl, heterocycloalkenyl, and heteroaryl. Each $R_1$, $R_2$, and $R_3$ can be unsubstituted or substituted. Without wishing to be bound by theory, it is thought that $R_1$, which is in the para-position with respect to the pi-bridging component (Component B) can be critical for the photophysical properties of the compound. Accordingly, in some embodiments, $R_1$ can include an amine derivative to increase the electron-donating properties. Moreover, in some embodiments, $R_1$ can be used for further conjugation to additional compounds through various linking moieties, e.g., an amide, ester, or ether linker, and the like. In some embodiments, $R_1$ can be selected from —$OCH_3$, $OCH_2COOR_g$, $OCH_2CH_2COOR_g$, $OCH_2CH_2CH_2SO_2R_g$, $NH_2$, $NHR_g$, $NR_2$, where $R_g$ can independently at each occurrence be methyl, ethyl, or any heterocycloalkyl, heterocycloalkenyl, and heteroaryl.

In some embodiments, Component A can be selected from:

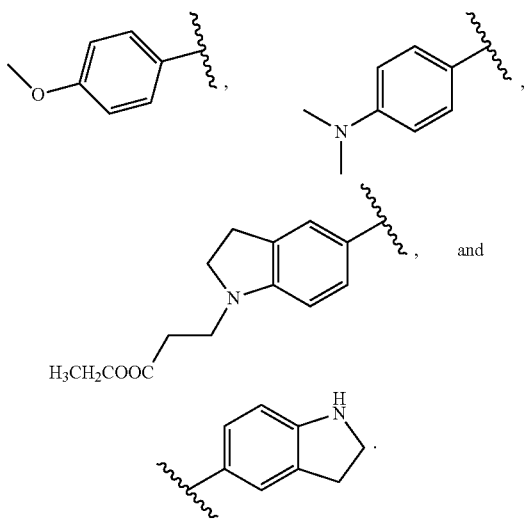

Component B: Pi-Bridge Moiety

Component B can generally comprise any pi-system moiety that bridges Component A (aryl system) and Component C (Zn(II)-chelator moiety). Component B can be a conjugated system that can include delocalized pi electrons across all the adjacent aligned p-orbitals in the pi-bridging moiety. Such extension of the pi-conjugation length typically produces a bathochromic (i.e., red) shift in the absorption and emission spectrum. Accordingly, in some embodiments, Component B can be any aryl or heteroaryl moiety including, but not limited to, thiazole, oxazole, imidazole, thiophene, furan, or pyrrole. In some embodiments, Component B can have the structure:

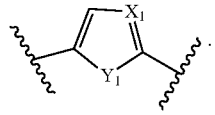

In some embodiments, $X_1$ can be selected from —N, and —CH. In some embodiments, $X_1$ can be —N. In some embodiments, $Y_1$ can be selected from —$NR_4$, —S—, and —O, where $R_4$ can be selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl. In some embodiments, $Y_1$ can be —S—. In some embodiments, Component B can be selected from

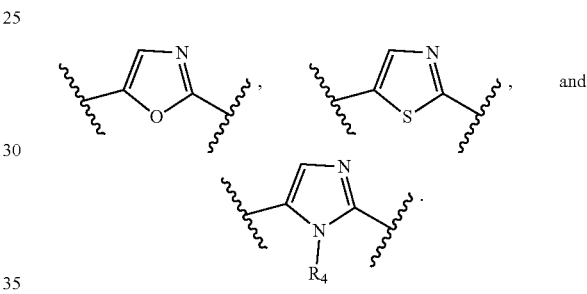

Component C: Zn-Chelator Moiety

Component C can generally comprise any moiety that will selectively bind to Zn(II) to form a Zn(II)-probe complex with a high fluorescent quantum yield of the bound Zn(II)-probe complex species. In other words, as defined herein, "selectively" means that the resulting bound complex has a fluorescent quantum yield of at least 15%. In some embodiments, Component C can have the structure:

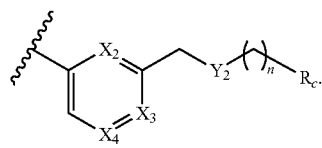

In some embodiments, $X_2$, $X_3$, and $X_4$ can be each independently selected from —N and —CH. In some embodiments, $X_2$ can be —N. In some embodiments, $X_3$ and $X_4$ can be —CH. In some embodiments, $Y_2$ can be selected from —$NR_5$, —S—, and —O, where $R_5$ can be selected from $C_n$-alkyl, optionally substituted with —OH or Ar, where n can be 1 or 2. In some embodiments, $R_5$ can be —$CH_2CH_2OH$. In some embodiments, $R_5$ can be —$CH_2$—Ar. In some embodiments, $R_c$ can be Ar, —$OR_4$, —$N(CH_2$—$Ar)_2$, where $R_4$ can be selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl. In some embodiments, Component C can be selected from

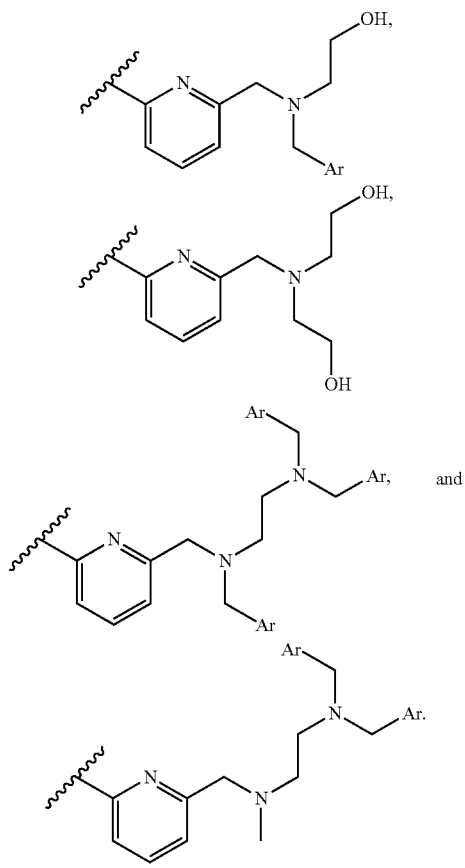

In some embodiments, Component C can be selected from:

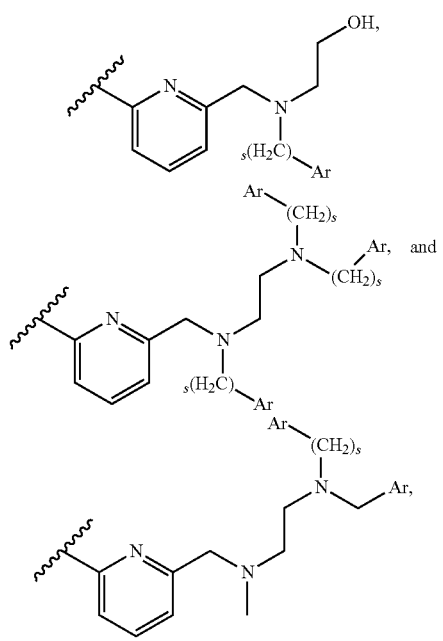

where s is 1, 2, or 3. In some embodiments, Ar can be selected from aryl and heteroaryl. In some embodiments, Ar can be independently at each occurrence selected from:

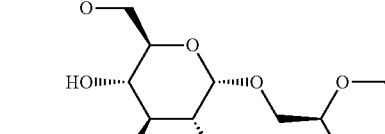

where m can be any integer from 0 to 3 and $R_4$ can be independently selected from at each occurrence hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl. In some embodiments Ar can be different at each occurrence. In some embodiments, Ar can be the same at each occurrence.

Additional Compounds

In some embodiments, the probe can be further conjugated to additional compounds. For example, in some embodiments, the probe can be conjugated to a dextran to decrease permeability of the probe across the cell membrane. In some embodiments, the dextran can be an amine-functionalized dextran with a molecular weight of about 70 kDa, e.g.:

Additional compounds for further conjugation include, but are not limited to SNAP, CLIP, or Halo tag. As would be clear to persons of ordinary skill in the art, SNAP-tag is a self-labeling protein tag which includes 182 residues polypeptide (19.4 kDa) that can be fused to any protein of interest and further specifically and covalently tagged with a suitable ligand, such as a fluorescent dye. CLIP-tag is an orthogonal tag further engineered from SNAP-tag to accept O2-benzylcytosine derivatives as substrates, instead of 06-benzylguanine. The HaloTag is a modified bacterial enzyme designed to covalently bind to a synthetic ligand of choice and fuse to a protein of interest. The HaloTag includes two covalently bound segments including a haloalkane dehalogenase and a synthetic ligand which can be chosen to suit the experiment. As such, the probe can include linking moieties, such as amide linker, through which additional compounds can be linked, for example an active ester for conjugation to amines, maleimide for thiol-selective conjugation, or an azide or alkyne for Cu-catalyzed alkyne-azide 1,3-dipolar cycloaddition (click chemistry).

One issue with fluorescent probes is the generation of other species upon excitation that can cause partial or complete quenching of fluorophore/probe. Such quenching can render potential probes ineffective for ratiometric imaging applications. For example, depending on the photophysical properties of the probe, various inter- and intra-molecular reactions can occur to cause fluorescence quenching. One such reaction is excited-state proton transfer (ESPT), which is a pH-dependent reaction that can cause fluorescence quenching of the fluorophore/probe. Such quenching can be an issue for ratiometric imaging in cellular environments, as intracellular pH is not uniform and can vary between pH~5 and pH~7. The propensity for a compound to undergo ESPT can depend on the excited-state pKa of the compound. The inventors have surprisingly discovered that both the ground- and excited-state pKa's of the inventive probes are such that the probes do not undergo any ESPT at physiological/intracellular pH ranges. Accordingly, one advantage of some embodiments of the disclosed invention is that the probe can be an emission-ratiometric fluorophore that can permit pH-independent ratiometric imaging (e.g., TPEM imaging) in biological samples for monitoring dynamic labile Zn(II) fluctuations in a wide array of biological applications, including, but not limited to, live cells, and tissue, and the like.

Accordingly, in some embodiments, the disclosed probes can be configured to bind to zinc(II) (Zn(II)) to form a fluorescent Formula I-Zn(II) complex. In some embodiments, the maximum absorption wavelength of the Formula I-Zn(II) complex can be from about 10 nm to about 50 nm, about 15 nm to about 50 nm, about 15 nm to about 40 nm, about 15 nm to about 35 nm, about 15 nm to about 30 nm, about 15 nm to about 25 nm, about 20 nm to about 50 nm, about 25 nm to about 45 nm, or about 25 nm to about 35 nm greater than a maximum absorption wavelength of the free compound of Formula I (i.e., the unbound compound). In some embodiments, the maximum emission wavelength of the Formula I-Zn(II) complex is from about 30 nm to about 80 nm, about 40 nm to about 60 nm, about 40 nm to about 50 nm, about 30 nm to about 60 nm, about 30 nm to about 50 nm, about 20 nm to about 40 nm greater than a maximum emission wavelength of the free compound of Formula I (i.e., the unbound compound).

Exemplary Probe Compounds

In an embodiment, the probe can be a compound according to Formula I:

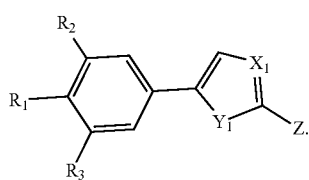

Formula I

In an embodiment, Z can be:

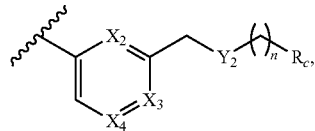

$X_1$, $X_2$, $X_3$, and $X_4$ can be each independently selected from —N and —CH; $Y_1$ can be selected from —NR$_4$, —S—, and —O; $Y_2$ can be selected from —NR$_5$, —S—, and —O; $R_e$ can be Ar, —OR$_4$, —N(CH$_2$)$_q$—Ar)$_2$; $R_1$, $R_2$, $R_3$, and $R_4$ can be each independently selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl; or $R_1$ and $R_2$; or $R_1$ and $R_3$ may together form a moiety selected from cycloalkyl, cycloalkenyl, aryl, heterocycloalkyl, heterocycloalkenyl, and heteroaryl; $R_5$ can be selected from $C_n$-alkyl optionally substituted with —OR$_4$ or Ar; and Ar can be independently at each occurrence selected from aryl and heteroaryl; where n can be 1, 2, or 3; q can be 1, 2, or 3; and any one of the aforementioned functional groups can be substituted or unsubstituted.

In some embodiments, $R_1$ can be selected from —OCH$_3$, OCH$_2$COOR$_9$, OCH$_2$CH$_2$COOR$_9$, OCH$_2$CH$_2$CH$_2$SO$_2$R$_9$, NH$_2$, NHR$_9$, N(R$_9$)$_2$; where $R_9$ is selected from —CH$_3$, C$_2$H$_5$, substituted or unsubstituted heteroalkyl, substituted or unsubstituted heteroalkenyl, substituted or unsubstituted heteroalkynyl, and substituted or unsubstituted heteroaryl. In some embodiments, $R_1$ is —OCH$_3$.

In some embodiments, $X_1$, $X_2$, and $Y_2$ can each be —N. In some embodiments, Z can be

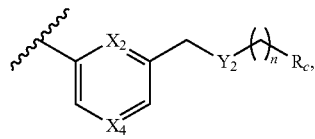

$X_2$ can be —N and $X_4$ can be —CH; or $X_2$ can be —N and $X_4$ can be —N.

In some embodiments, Z can be

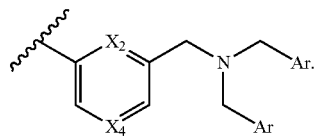

In some embodiments, Z can be selected from Ar,

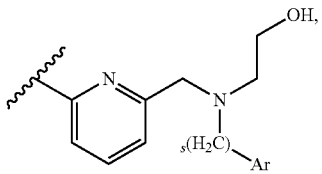

-continued

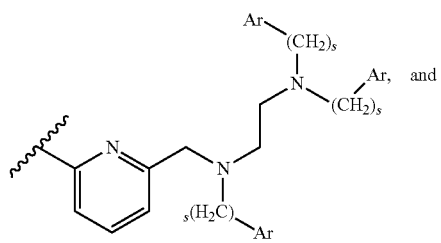

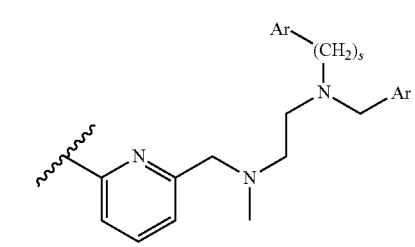

where s can be 1, 2, or 3.

In some embodiments, Z can be selected from:

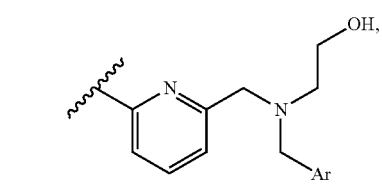

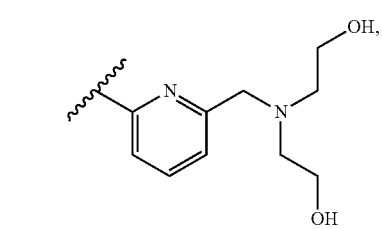

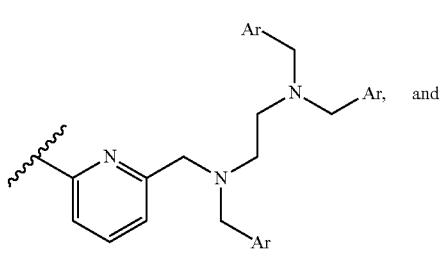

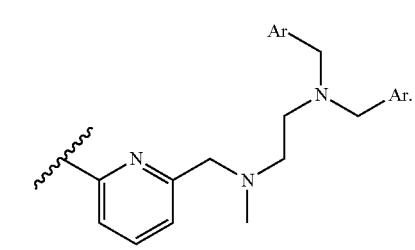

In some embodiments, Formula I can be selected from

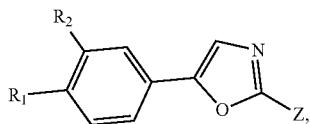

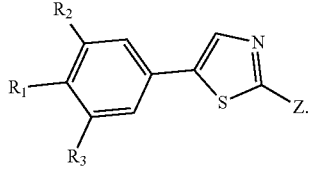

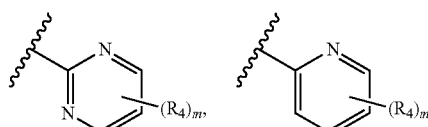

In some embodiments, Ar can be independently at each occurrence selected from:

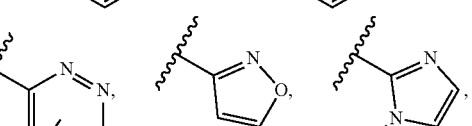

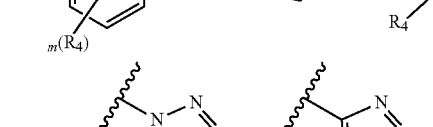

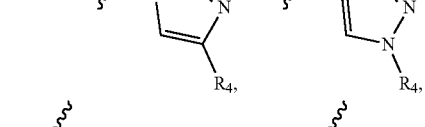

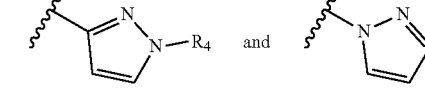

where m can be any integer from 0 to 3. In some embodiments Ar can be the same at each occurrence. In some embodiments, Ar can be different at each occurrence.

In some embodiments, Formula I can be

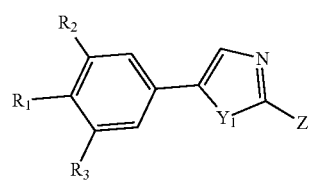

and $Y_1$ can be selected from O, S, and $NR_4$, where $R_4$ can be selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl.

In some embodiments, Formula I can be

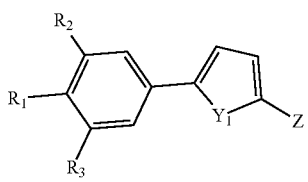

and $Y_1$ can be selected from O, S, and $NR_4$, where $R_4$ can be selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl.

In some embodiments, Formula I can be

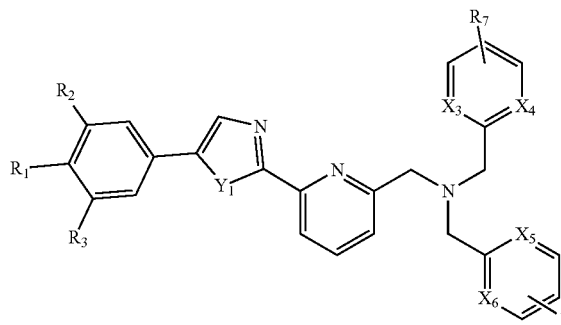

wherein $X_3$ and $X_5$ can be each independently selected from absent, —CH, —O— and —N; $X_4$, and $X_6$ can be each independently selected from —CH, —O— and —N; and $R_7$ and $R_8$ can be each independently selected from H, —CH$_3$, —OR$_4$, —CF$_3$, —F, —Cl, —CN, —COOR$_4$, —SO$_2$R$_4$, where $R_4$ can be selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl, where $R_1$ can be selected from —OCH$_3$, OCH$_2$COOR$_9$, OCH$_2$CH$_2$COOR$_9$, OCH$_2$CH$_2$CH$_2$SO$_2$R$_9$, NH$_2$, NHR$_9$, N(R$_9$)$_2$ and $R_9$ can be selected from —CH$_3$, C$_2$H$_5$, substituted or unsubstituted heteroalkyl, substituted or unsubstituted heteroalkenyl, substituted or unsubstituted heteroalkynyl, and substituted or unsubstituted heteroaryl. In some embodiments, $R_1$ is —OCH$_3$.

In some embodiments, $R_1$ and $R_2$ can together form a moiety selected from substituted or unsubstituted heterocycloalkyl, substituted or unsubstituted heterocycloalkenyl, and substituted or unsubstituted heteroaryl; and $R_3$ can be hydrogen.

In some embodiments, Formula I can be:

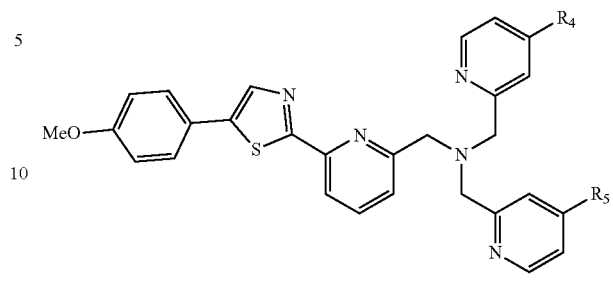

Wherein $R_4$ and $R_5$ can be independently selected from hydrogen and CO$_2$R$_7$; and $R_7$ can be a C$_1$-C$_8$ alkyl. In some embodiments, $R_7$ can be selected from H, —CH$_3$, and —C$_2$H$_5$.

In some embodiments, Formula I can be selected from:

Compound 1

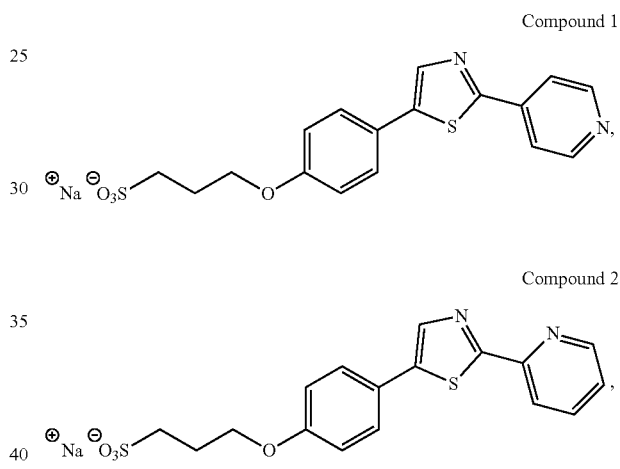

Compound 2

Compound 3a

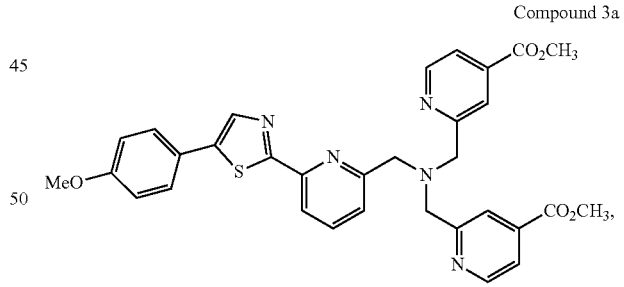

Compound 3b

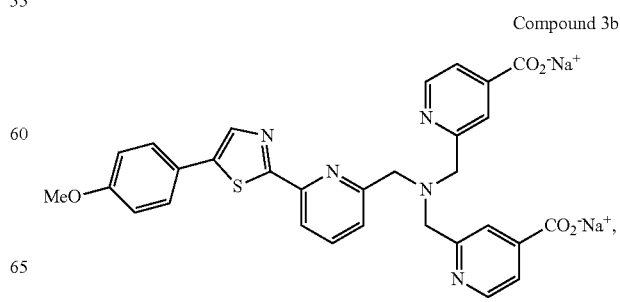

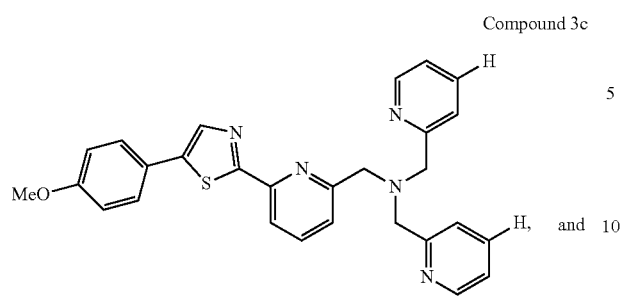
Compound 3c
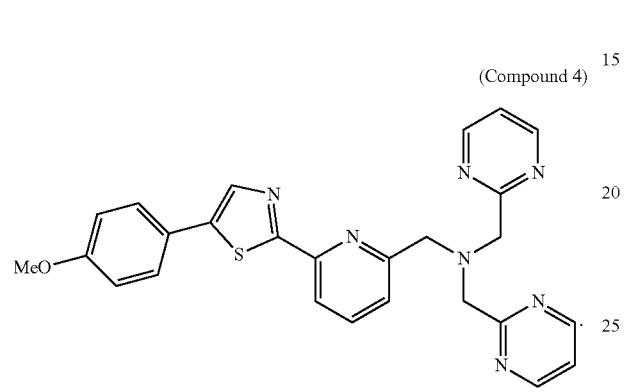
(Compound 4)
Chromis-2
In some embodiments, Formula I can be selected from:
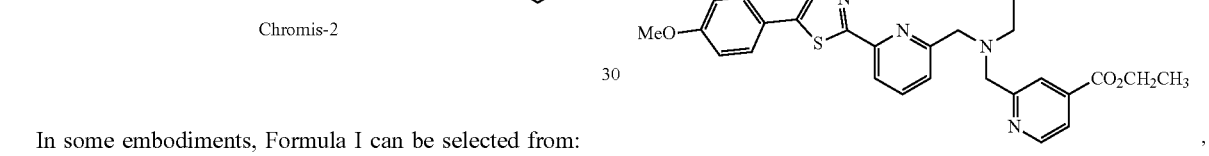
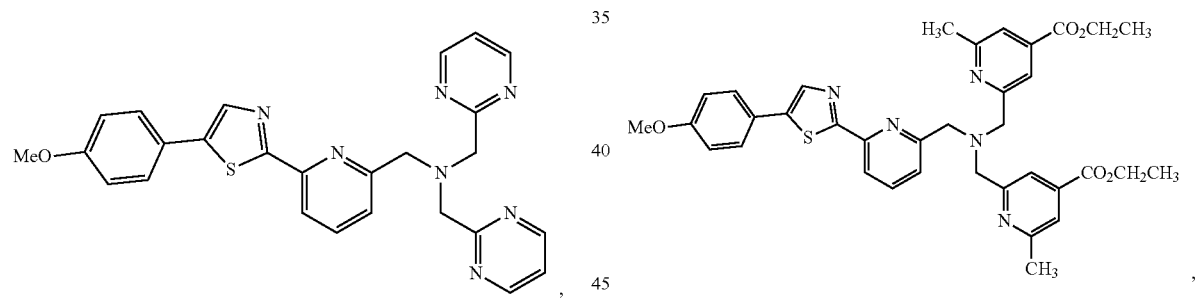
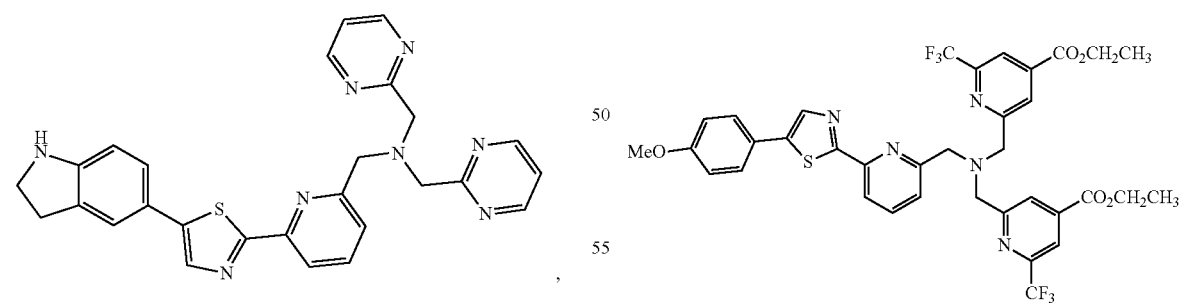
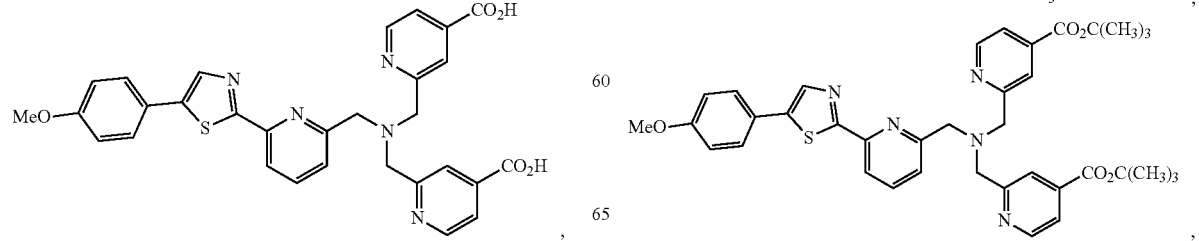
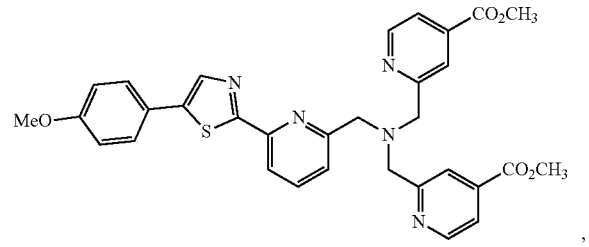
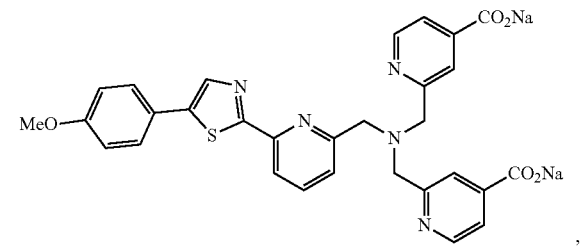
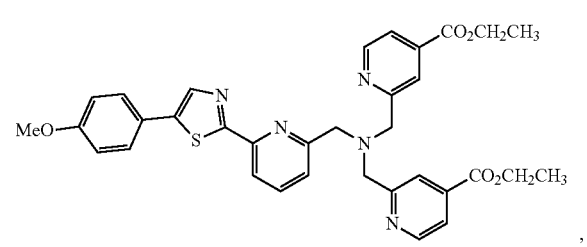

-continued
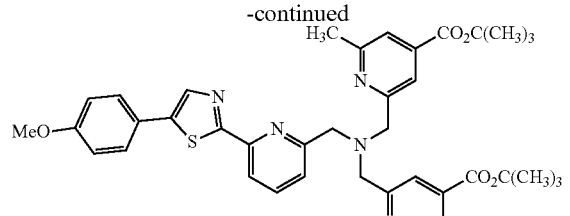
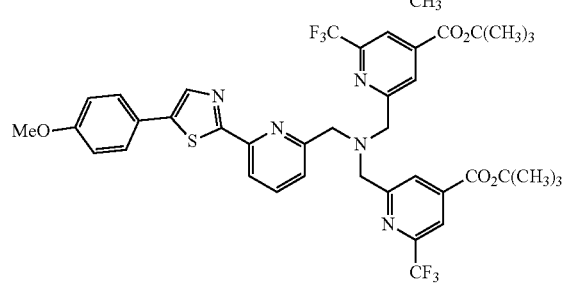
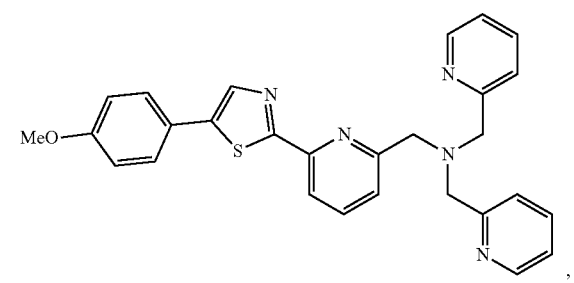
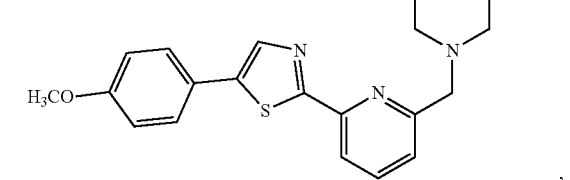
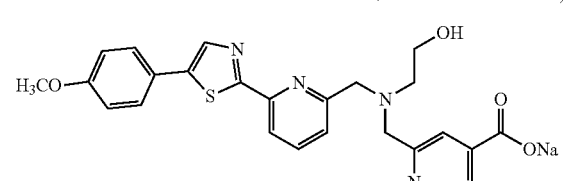
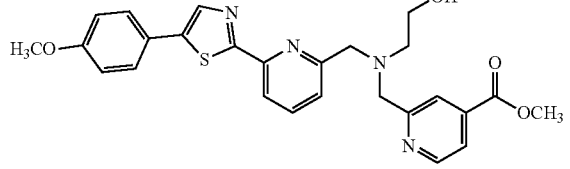
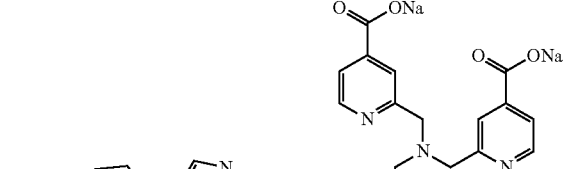
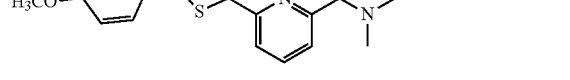
-continued
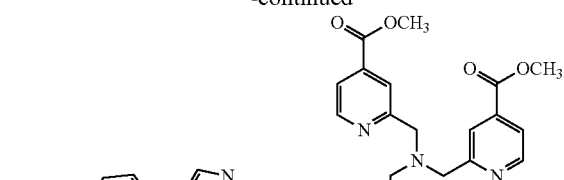
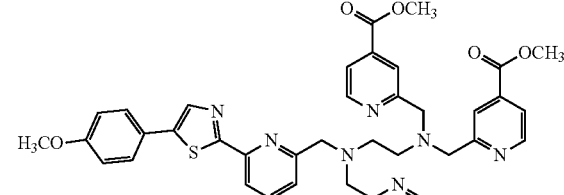
, and

In some embodiments, the probe can be any one of the following compounds:
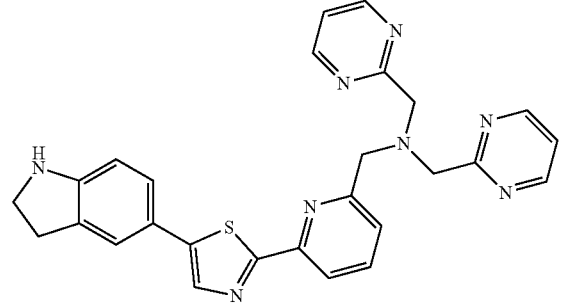
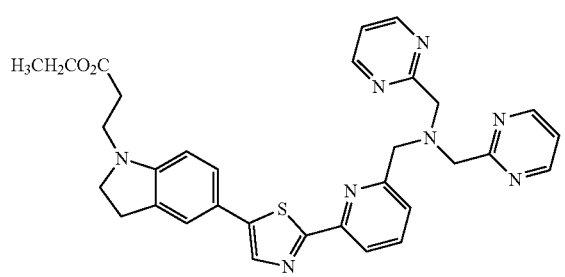
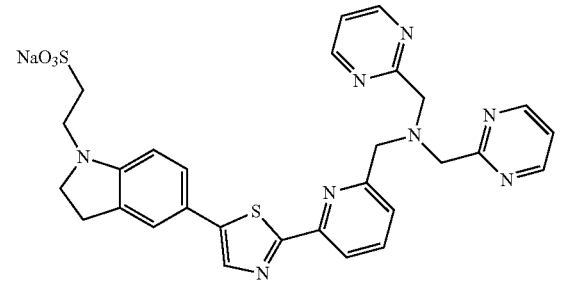
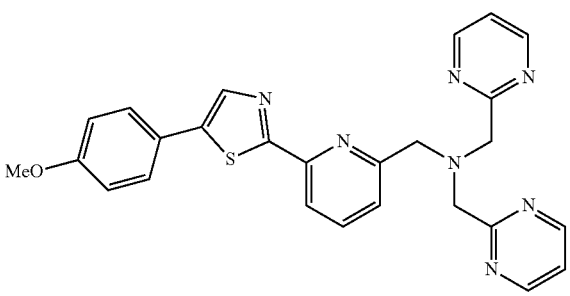
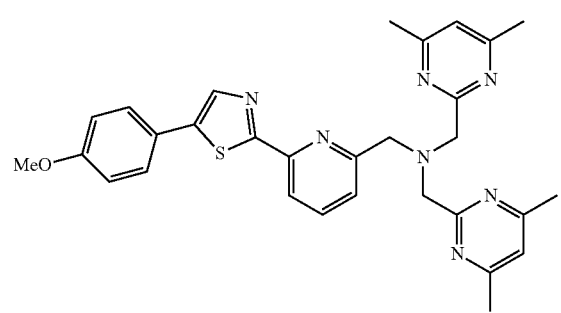
-continued
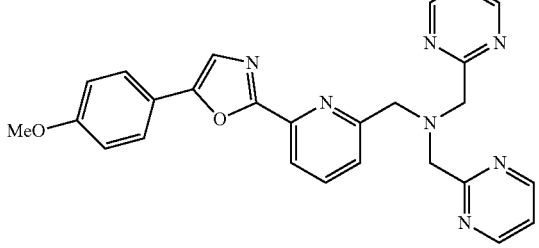
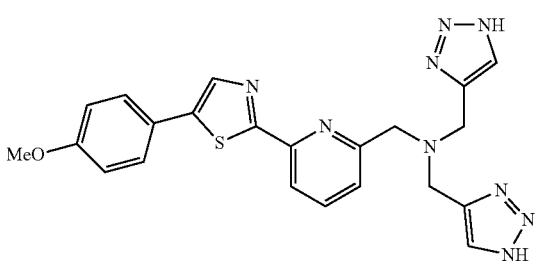
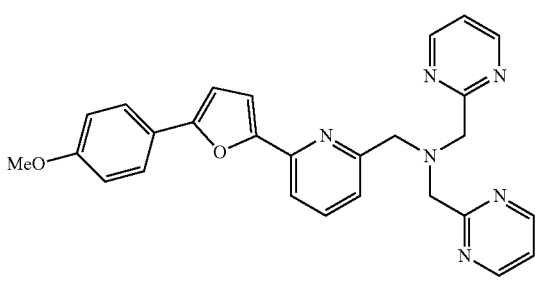
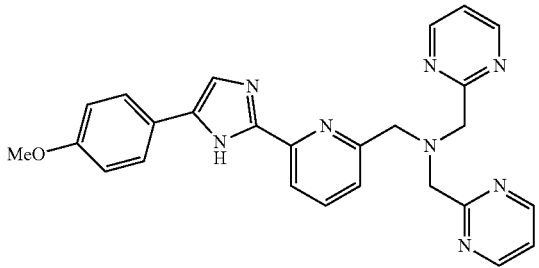
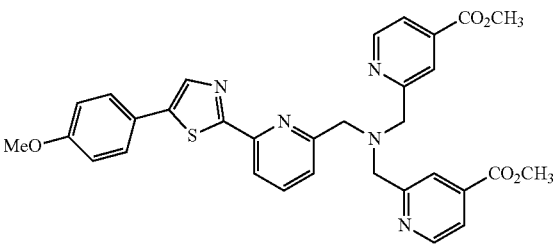
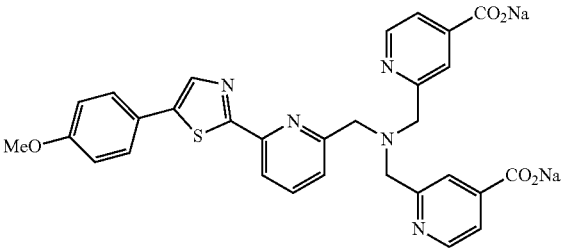

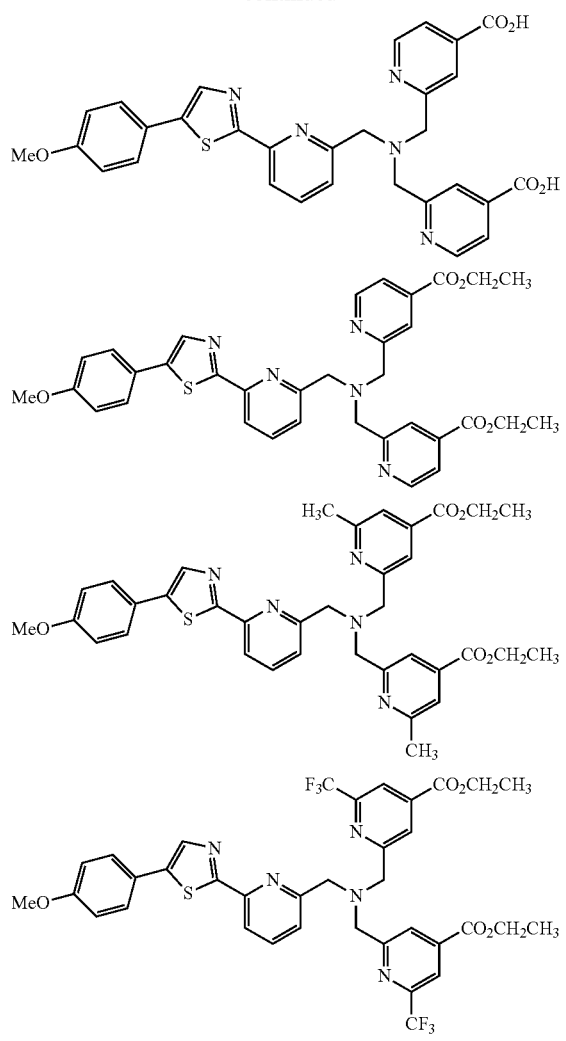
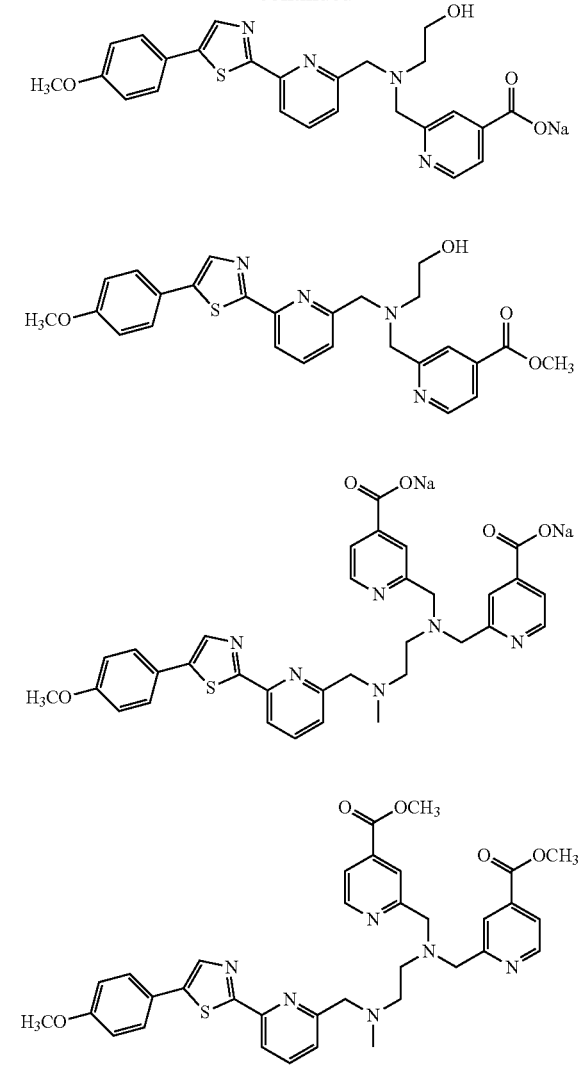
In some embodiments, the probe can be any one of the following compounds:
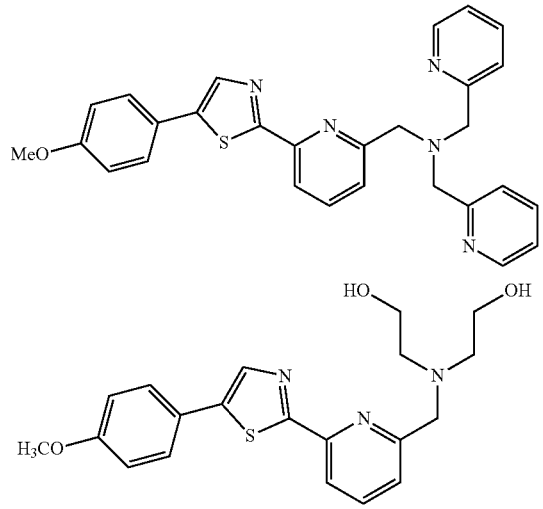
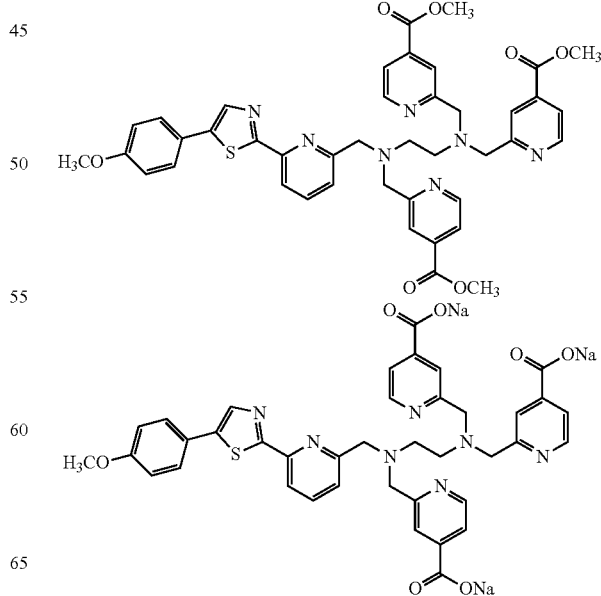

-continued

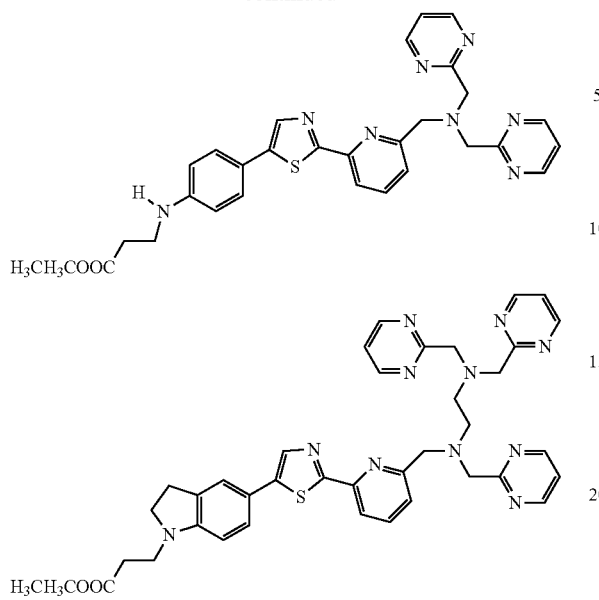

In some embodiments, the probe can be selected from:

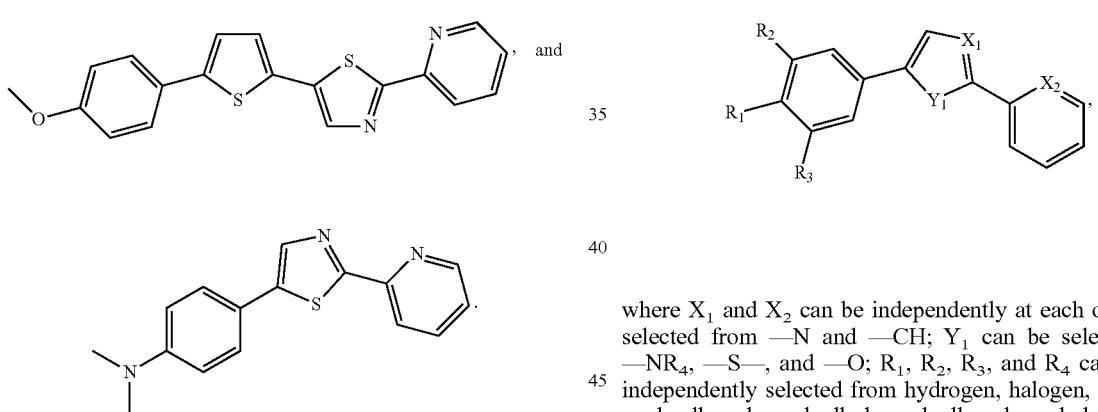

In some embodiments, the compound of Formula I can be:

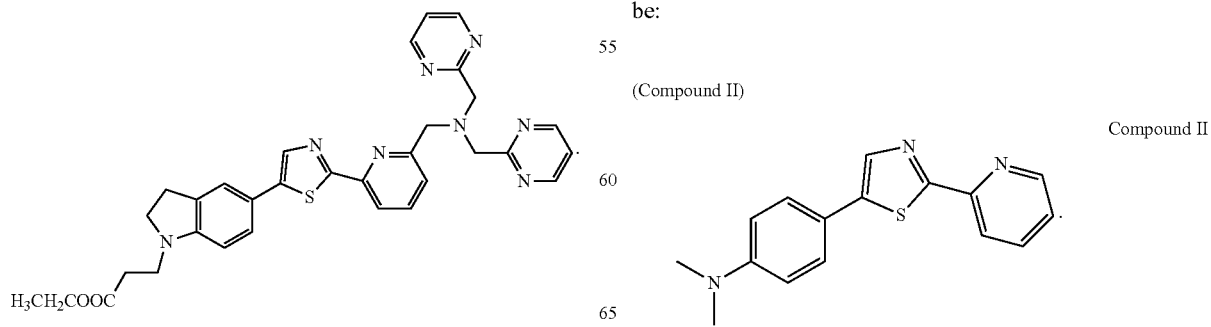

In some embodiments, the compound of Formula I can be:

(Compound 4)

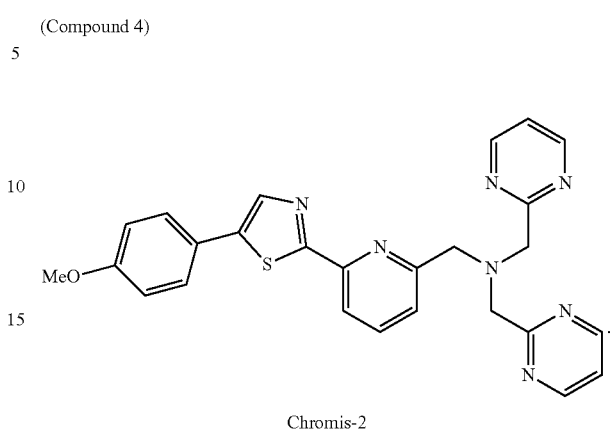

Chromis-2

In some embodiments, the probe can be a compound of Formula IA:

Formula IA where $X_1$ and $X_2$ can be independently at each occurrence selected from —N and —CH; $Y_1$ can be selected from —NR$_4$, —S—, and —O; $R_1$, $R_2$, $R_3$, and $R_4$ can be each independently selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl; or $R_1$ and $R_2$; or $R_1$ and $R_3$ may together form a moiety selected from cycloalkyl, cycloalkenyl, aryl, heterocycloalkyl, heterocycloalkenyl, and heteroaryl.

In some embodiments, the compound of Formula IA can be:

(Compound II)

Compound II

In some embodiments, the probe can be a compound of Formula 2:

Formula 2

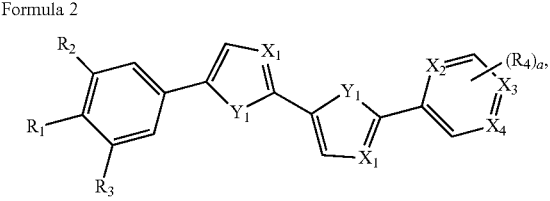

$X_1$, $X_2$, $X_3$, and $X_4$ can be independently at each occurrence selected from —N and —CH; $Y_1$ can be selected from —$NR_4$, —S—, and —O; $R_1$, $R_2$, $R_3$, and $R_4$ can be each independently selected from hydrogen, halogen, alkyl, alkenyl, alkynyl, cycloalkyl, cycloalkenyl, aryl, heteroalkyl, heteroalkenyl, heteroalkynyl, heterocycloalkyl, heterocycloalkenyl, and heteroaryl; or $R_1$ and $R_2$; or $R_1$ and $R_3$ may together form a moiety selected from cycloalkyl, cycloalkenyl, aryl, heterocycloalkyl, heterocycloalkenyl, and heteroaryl; "a" can be 1, 2, 4, or 4; and any one of the aforementioned functional groups can be substituted or unsubstituted.

In some embodiments, the compound of Formula II can be:

(Compound III)

Compound III

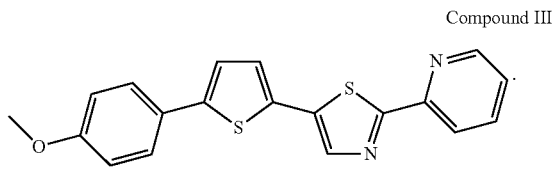

In some embodiments, the probe compound of Formula I is configured to bind to zinc(II) (Zn(II)) to form a fluorescent complex comprising Formula I-Zn(II) in a 1:1 stoichiometric ratio.

For example, in some embodiments, the bound probe-Zn(II) complex can have the structure:

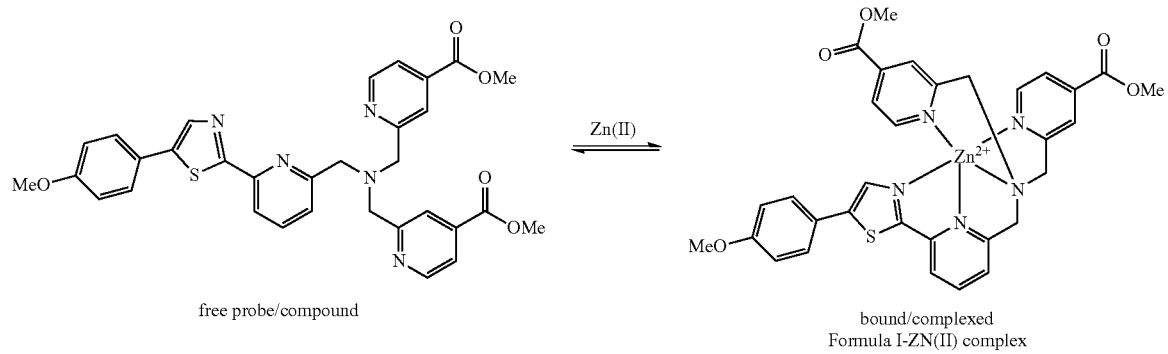

free probe/compound bound/complexed
Formula I-ZN(II) complex

In some embodiments, the fluorescent complex, e.g., the probe-Zn(II) complex can comprise an additional ligand. The additional ligand can be selected from any possible ligands (L) that may be present in or near a cell, including, but not limited to, chloride, and the like. In an embodiment, the probe-Zn(II)-ligand complex can have the structure:

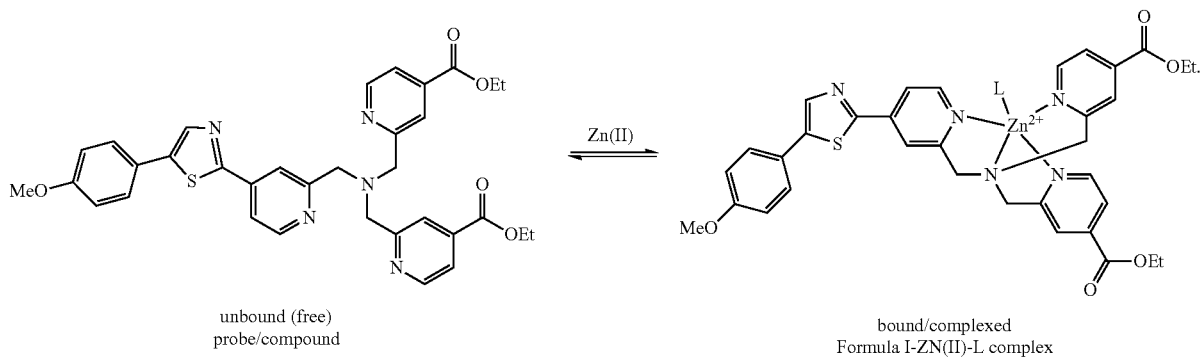

unbound (free)
probe/compound bound/complexed
Formula I-ZN(II)-L complex

Exemplary Methods

The probe compounds described herein can be used in a wide variety of metal detecting methods, including, but not limited to UV-vis absorption spectroscopy, steady state fluorescence spectroscopy, and time-resolved fluorescence spectroscopy.

An embodiment of the present disclosure can be a method of detecting zinc in a sample comprising the steps of: (1) treating the sample with a Zn probe, for example, the Zn probe can comprise or consist of a compound of Formula I Formula I

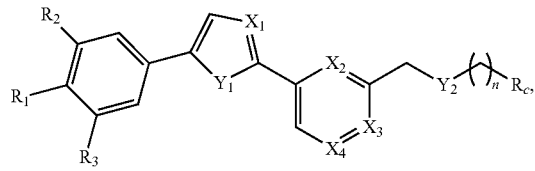

and/or a compound of Formula IA

Formula IA

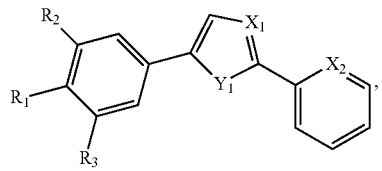

and/or a compound of Formula 2

Formula 2

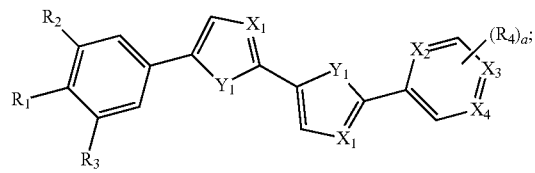

(2) detecting a light emission from the Zn probe, the light emission comprising a first wavelength emission and a second wavelength emission, wherein the first wavelength emission intensity can be associated with an unbound Zn probe and the second wavelength emission intensity can be associated with a zinc-bound Zn probe complex; and (3) comparing the first wavelength emission intensity to the second wavelength emission intensity to determine the concentration of zinc in the sample. In some embodiments, the method can further comprise excitation of the at a wavelength associated with the absorption of the Zn probe, the Zn(II)-probe complex, or both. In some embodiments where the excitation wavelength is only associated with the Zn(II)-probe complex, the detected light emission can be associated only with the Zn(II)-probe I complex. In some embodiments, the single photon excitation wavelength can be from about 300 nm to about 500 nm, about 350 nm to about 480 nm, or about 350 nm to about 460 nm. As such, the two-photon excitation wavelength can be from about 600 nm to about 1000 nm, about 700 nm to about 960 nm, or about 700 nm to about 920 nm. A person of ordinary skill in the art would know that various lasers can be employed as single wavelength excitation sources.

In some embodiments, the method can further comprise excitation of the at a wavelength associated with the absorption of the compound of Formula I, the Zn(II)-Formula I complex, or both. In some embodiments where the excitation wavelength is only associated with the Zn(II)-Formula I complex, the detected light emission can be associated only with the Zn(II)-Formula I complex. In some embodiments, the single photon excitation wavelength can be from about 300 nm to about 500 nm, about 350 nm to about 480 nm, or about 350 nm to about 460 nm. As such, the two-photon excitation wavelength can be from about 600 nm to about 1000 nm, about 700 nm to about 960 nm, or about 700 nm to about 920 nm. A person of ordinary skill in the art would know that various lasers can be employed as single wavelength excitation sources.

In some embodiments, the detection method can be two-photon excitation microscopy. In some embodiments, the detection method can be traditional single-photon fluorescence microscopy. In some embodiments, the detection method can be confocal laser scanning microscopy. In some embodiments, the single photon excitation wavelength can be from about 300 nm to about 500 nm, about 350 nm to about 480 nm, or about 350 nm to about 460 nm. As such, the two-photon excitation wavelength can be from about 600 nm to about 1000 nm, about 700 nm to about 960 nm, or about 700 nm to about 920 nm. A person of ordinary skill in the art would know that various lasers can be employed as single wavelength excitation sources.

In some embodiments, the light emission from the compound of Formula I can be from about 350 nm to about 700 nm, about 380 nm to about 700 nm, or about 400 nm to about 680 nm.

As used herein, "chromis-2" and "compound 4" are interchangeable. As used herein, "probe" refers to the inventive compounds described herein, and unless otherwise specified, "probe" may describe the compounds in free state, bound/complexed to zinc or any other metal, and/or further linked or conjugated to any other compound, linker, ligand, and the like. For example and not limitation, "Zn probe" can refer to, e.g., compounds included in general Formula I, Formula IA, and/or Formula 2. Additionally, by way of example only "Zn-probe complex" can include Zn(II)—Formula I complex, Zn(II)—Formula IA complex, and/or Zn(II)-Formula 2 complex.

The term "optionally substituted" or "substituted" means that the referenced group may be substituted with one or more additional group(s) individually, including various known protecting groups. The protecting groups that may form the protective derivatives of the above substituents are known to those of skill in the art and may be found in references such as Greene and Wuts, above. Unless otherwise specified, any of the substituents described herein can be substituted or unsubstituted. For example, "alkyl" can include, e.g., propyl or substituted propyl e.g. propyl bromide.

EXAMPLES

Example 1. Characterization of Chromis-2 (Compound 4)

Depending on the excited-state pKa, pyridines have the propensity to act as photobases, and protonation of the heterocyclic nitrogen can lead to quenching of the fluorophore, as is the case with 8-hydroxyquinoline. A water-soluble, chelator-less compound (compound 1, Chart 1) was synthesized. The inventors surprisingly discovered that both the ground- and excited-state pKas of the pyridyl acceptor nitrogen dropped 2 log units when the nitrogen was isomerized from the 4-thiazolyl to the 2-thiazolyl position. Solvent deuterium isotope studies also revealed a complete eradication of a deuterium-mediated fluorescence-intensity increase. The inventors surprisingly found that this new acceptor design can be used in the synthesis of a less pH-sensitive ratiometric fluorophore (compounds 3a/b). However, analysis of water-soluble compound 3b still showed a solvent-deuterium isotope effect, as well as an unbalanced emission profile between the apo and Zn(II)-saturated forms, suggesting that the chelator pyridines are eliciting an excited-state intramolecular proton transfer (ES-IPT) that leads to partial quenching of the fluorophore. To overcome ESIPT, the inventors designed an alternative chelator that utilized pyrimidine rings instead of pyridine rings to significantly reduce protonation at or below neutral pH.

Compounds described herein include:

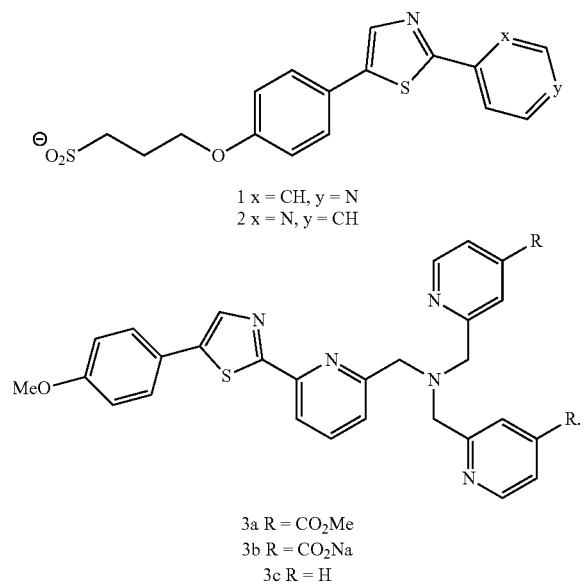

1 x = CH, y = N
2 x = N, y = CH

3a R = CO$_2$Me
3b R = CO$_2$Na
3c R = H

Elucidating the photobasicity of chromis-1.

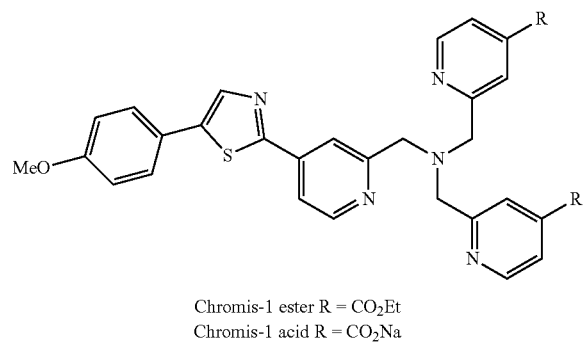

Chromis-1 ester R = CO$_2$Et
Chromis-1 acid R = CO$_2$Na

Figure 5:
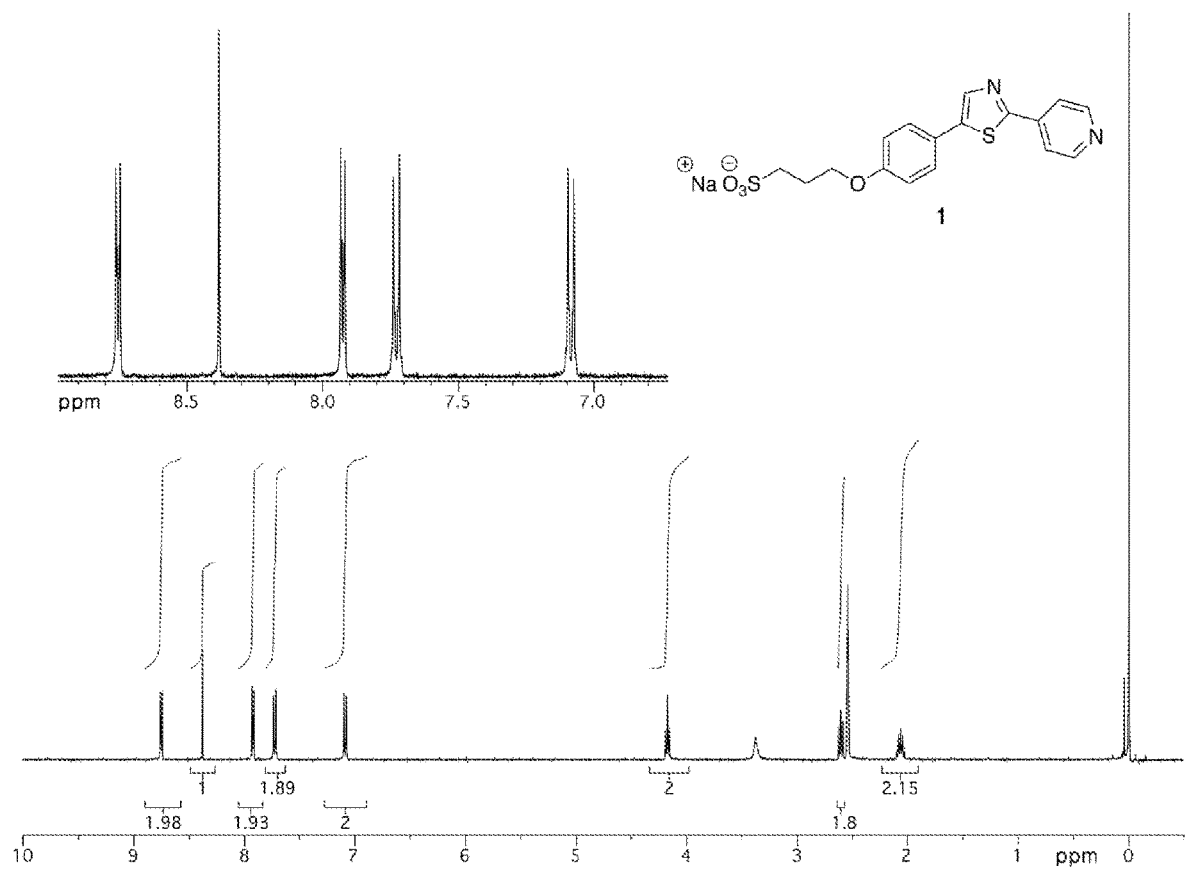
FIG. 5. NMR spectra of compound 1, including $^1$H NMR (DMSO-d6, 400 MHz) and $^{13}$C NMR (DMSO-d6, 100 MHz).
Figure 5:
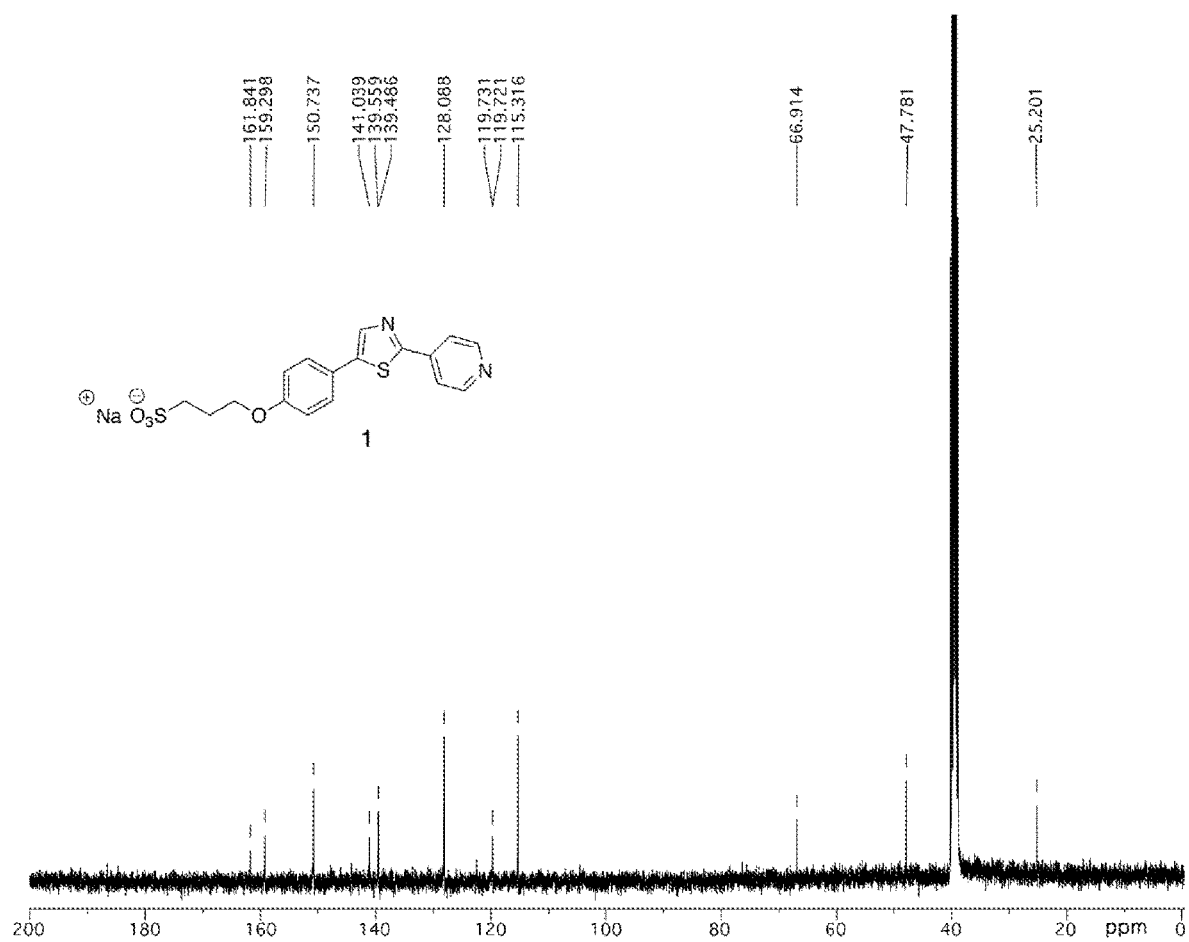
Figure 6:
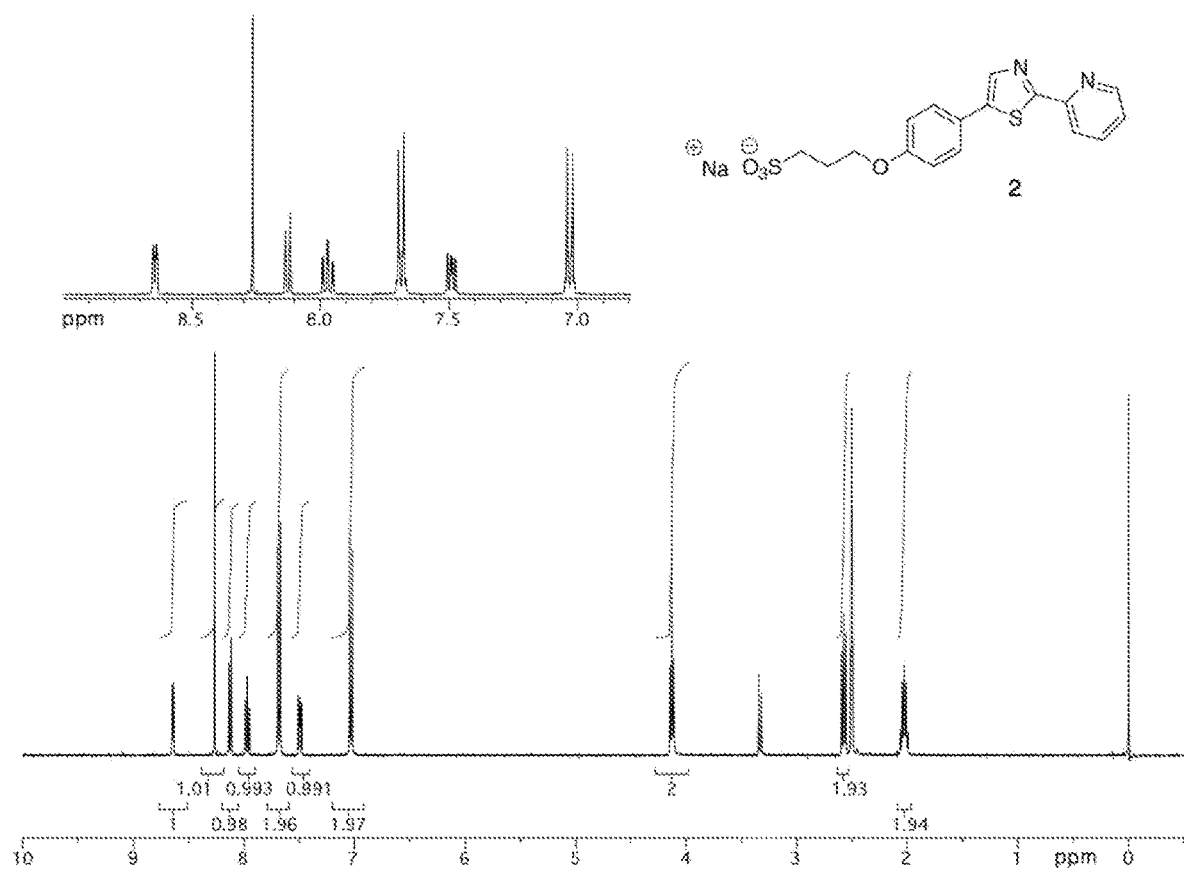
FIG. 6. NMR spectra of compound 2, including $^1$H NMR (DMSO-d6, 400 MHz) and $^{13}$C NMR (DMSO-d6, 100 MHz).
Figure 6:
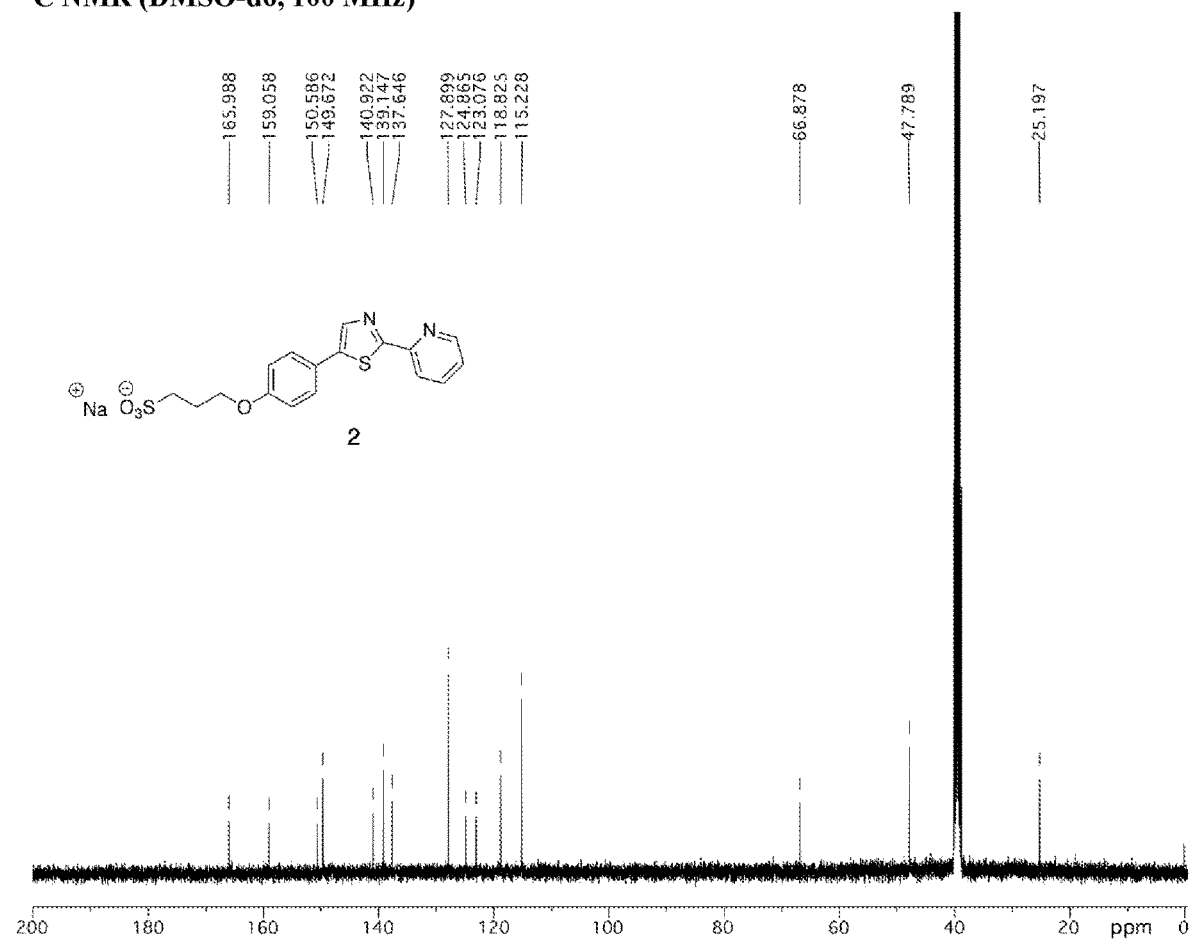

Spectrophotometric determination of the individual pKa's of chromis-1 acid revealed a slight bathochromic shift and decrease in absorbance between pH 7 and pH 5, but a distinguishable red-shift in the absorbance, attributed to the protonation of the fluorophore's pyridine, was not observed until below pH 2 (FIG. 5). However, analogous fluorimetric determination of these pKa values revealed a ~50% decrease in fluorescence intensity, as well as the emergence of a second emission maximum at ~560 nm, between pH 7 and pH 5, suggesting that the fluorophore is being partially protonated in the excited state, even at or slightly below neutral pH (FIG. 5). Analysis of the emission spectrum of chromis-1 at pH 1 shows a further 20-nm bathochromic shift to ~580 nm, consistent with a species in which all three pyridine rings are protonated based on pKa values determined by UV-Vis measurements. Without wishing to be bound by theory, it was suggested that the 560-nm emission maximum results from the production of a species in which only the fluorophore pyridine is protonated in the excited state, and the other two pyridines remain negatively charged; therefore, this species can only be transiently produced in the excited state, as the basicity of the chelator pyridines would favor protonation of these two groups before protonation of the fluorophore.

Figure 1B:
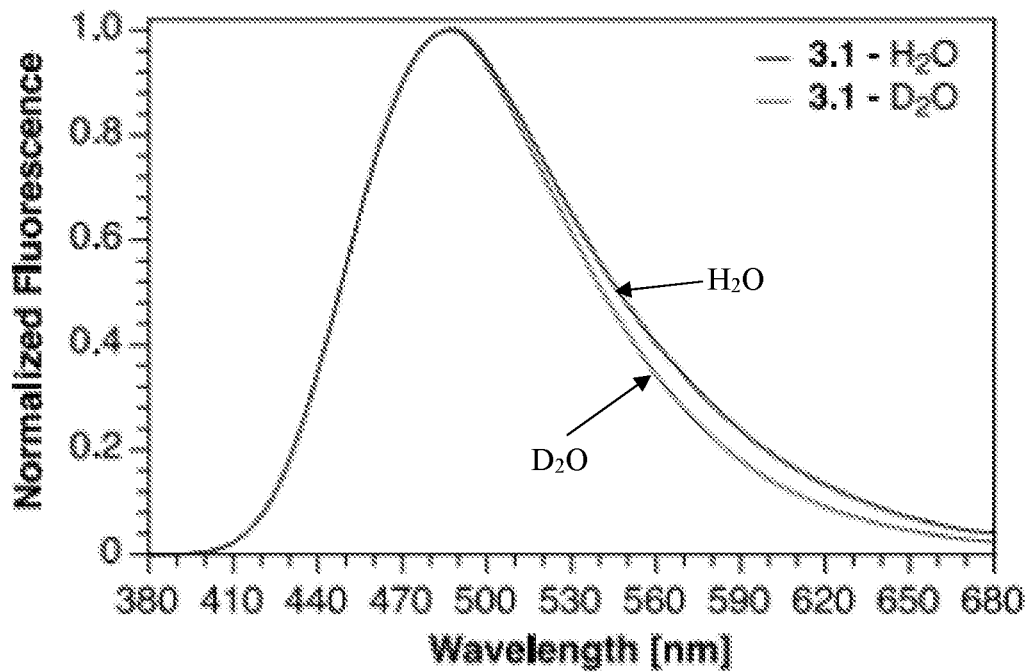
Figure 1C:
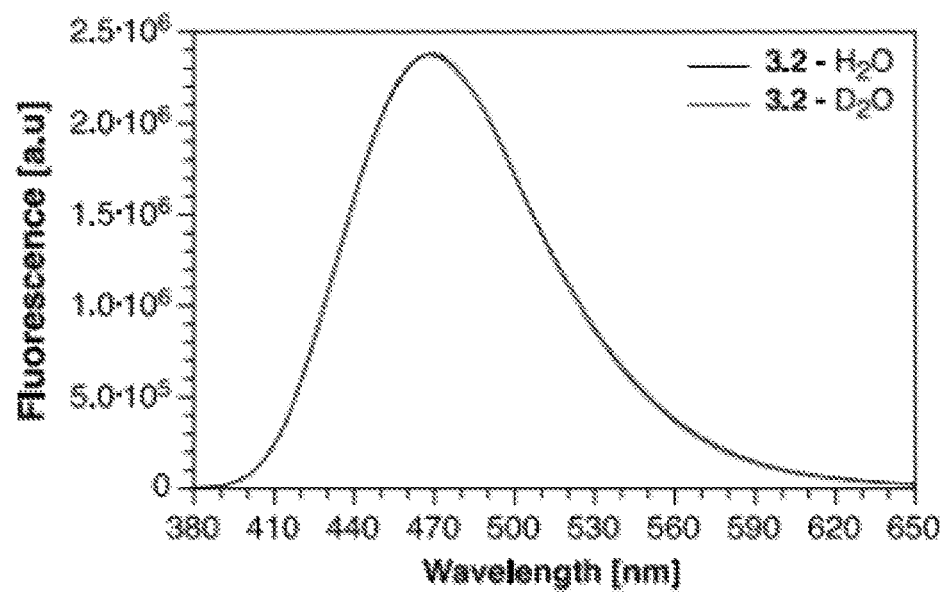

To circumvent the issue of excited-state protonation of the fluorophore, the inventors synthesized a chromis-1 compound 1, whose structure lacked the bis(2-pyridylmethyl) amine chelating moiety but incorporated an O-alkylsulfonate group to enhance water solubility, to determine the unperturbed ground-state pKa of the pyridyl acceptor. Spectrophotometric data (FIG. 5) of 1 fitted to a single protonation equilibrium displayed a pKa of 4.49±0.002, more than 3 log units higher than the pKa of the pyridyl acceptor with the chelator moiety attached. In addition, using the Forster Cycle, the inventors calculated the excited-state pKa to be approximately 11.7, suggesting that the pyridyl acceptor can act as a photobase. Solvent deuterium isotope measurements of 1 in deuterated and non-deuterated buffers (10 mM PIPES, 0.1 M KCl, pH/D 7.0, 25° C.) revealed an 18% increase in fluorescence intensity in D$_2$O relative to H$_2$O buffer (FIG. 1A), and, when normalized to the spectrum in D$_2$O, the spectrum of 1 in H$_2$O is broader and less featured, demonstrating that ESPT is disfavored in deuterated solvents (FIG. 1B).

Optimization of the fluorophore design. The surprising decrease in the protonation constants of the 2-oxazolyl versus the 4-oxazolyl fluorophores served as an impetus for designing a compound in which the pyridyl acceptor was isomerized from the 2-position relative to the bridging thiazole to the 4-position. The ground-state pKa of the pyridyl acceptor in compound 2 surprisingly decreased from 4.49 to 2.34; the calculated excited-state pKa of 2 also dropped two log units from 11.7 to 9.4, which indicated a substantial reduction in the photobasicity of the pyridine nitrogen. Fluorescence quantum yield measurements of 2 gave a $\Phi_F$ of 0.65 when referenced to quinine sulfate ($\Phi_F$=0.546 in 1N H$_2$SO$_4$)$_3$, whereas 1 gave a $\Phi_F$ of 0.80. In addition, solvent deuterium isotope measurements of 2 revealed identical emission profiles in D$_2$O versus H$_2$O buffers, alluding to the eradication of ESPT. Therefore, the inventors incorporated the isomerized pyridyl acceptor into the design of a less pH-sensitive ratiometric fluorophore (3a/b) for two-photon excitation microscopy.

Figure 2A:
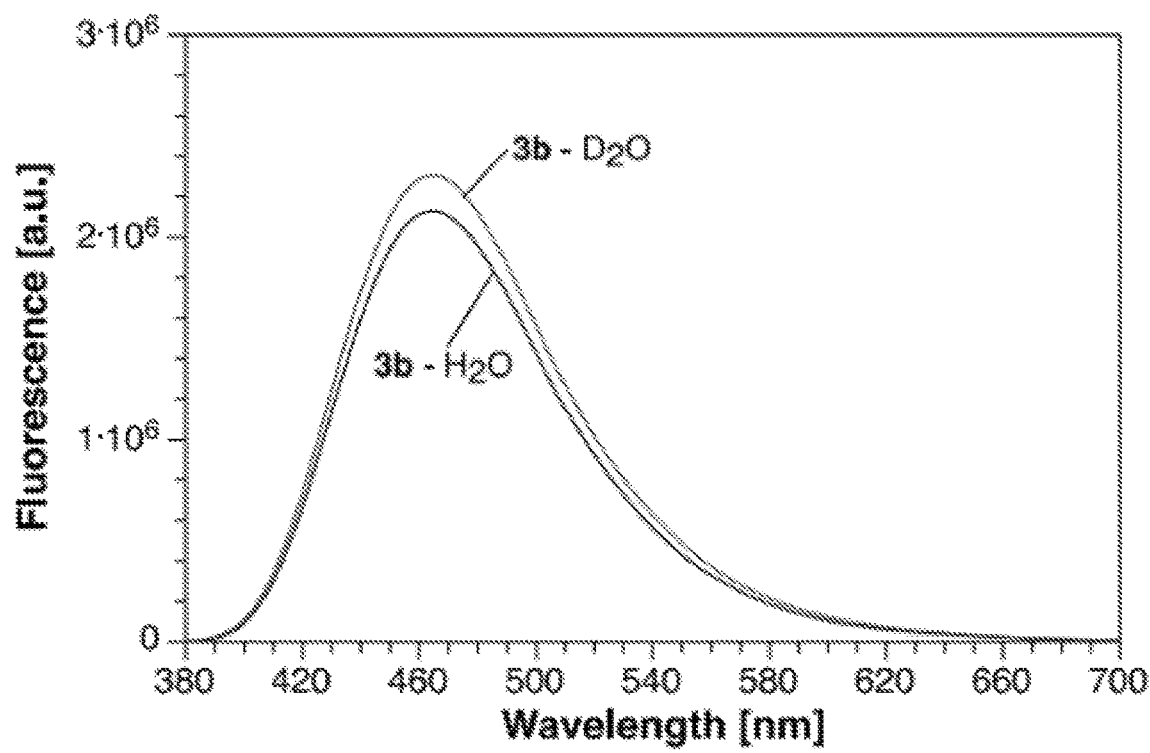
FIG. 2A-2B. Comparison of solvent deuterium isotope effect between compound 3b and chromis-2 (compound 4).
Figure 2B:
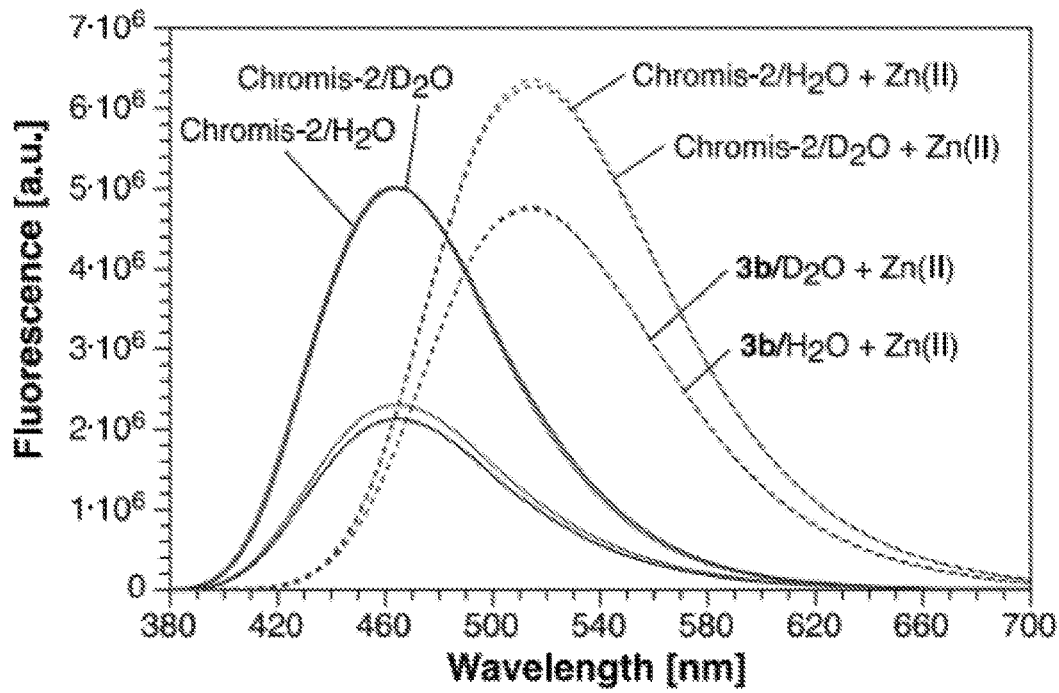

Despite the substantial difference in the pKas of the pyridyl acceptor between 1 and chromis-1, it was hypothesized that the two-log-unit discrepancy in the pKa between 1 and 2 should render the water-soluble 3b pH insensitive physiologically relevant conditions. Despite the lack of a deuterium-isotope effect in 2, fluorimetric measurements of 3b in pH 7.0 buffer showed a deuterium-isotope effect with a 10% increase in fluorescence intensity in D$_2$O relative to H$_2$O (FIG. 2A), suggesting that ESPT to the pyridyl acceptor of the fluorophore is still a viable phenomenon, resulting in a partial quenching and a reduction in the quantum yield of the free fluorophore. Fluorescence quantum yield measurements of 3b gave a modest $\Phi_F$ of 0.25 compared to 0.65 in the corresponding compound (2), indicating that the bis(2-pyridylmethyl)amine chelator may influence the reduction in fluorescence quantum yield of the free form of 3b.

Figure 7:
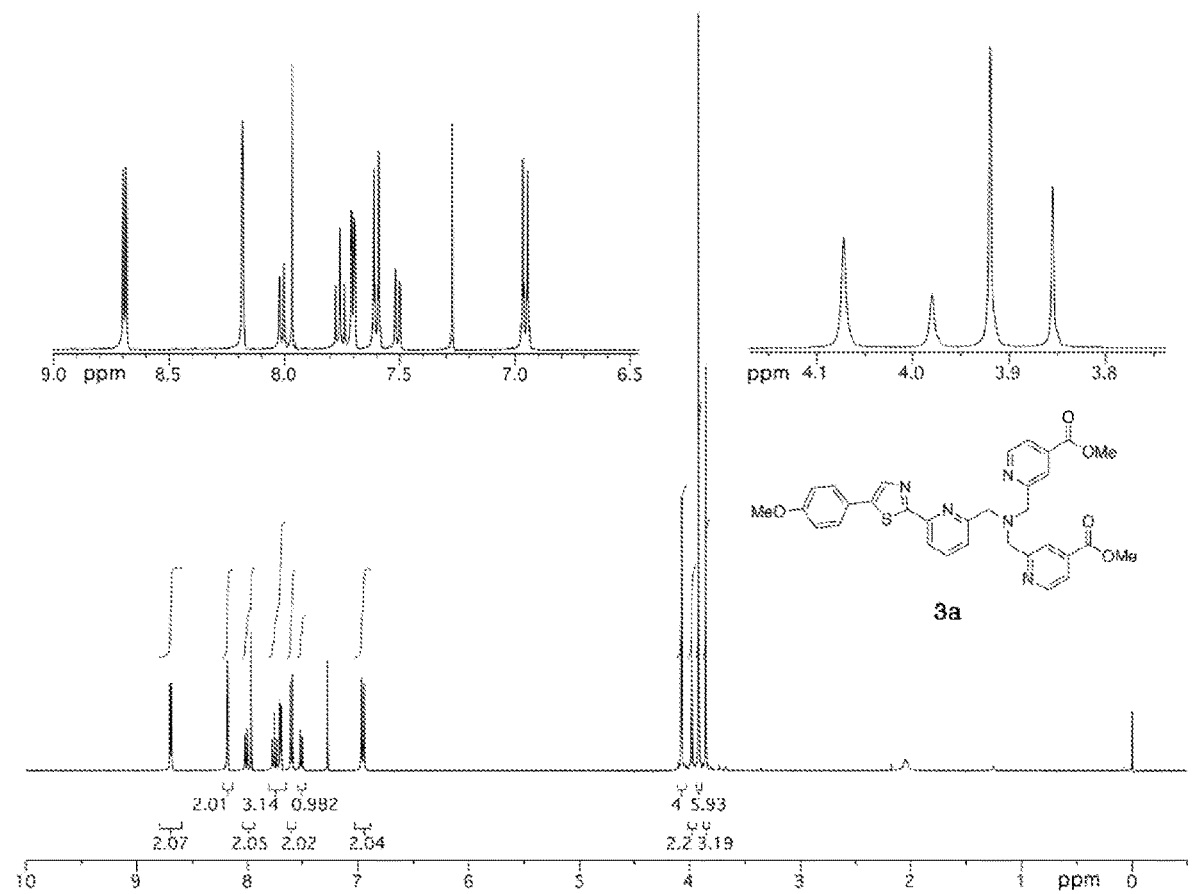
FIG. 7. NMR spectra of compound 3a, including $^1$H NMR (DMSO-d6, 400 MHz) and $^{13}$C NMR (DMSO-d6, 100 MHz).
Figure 7:
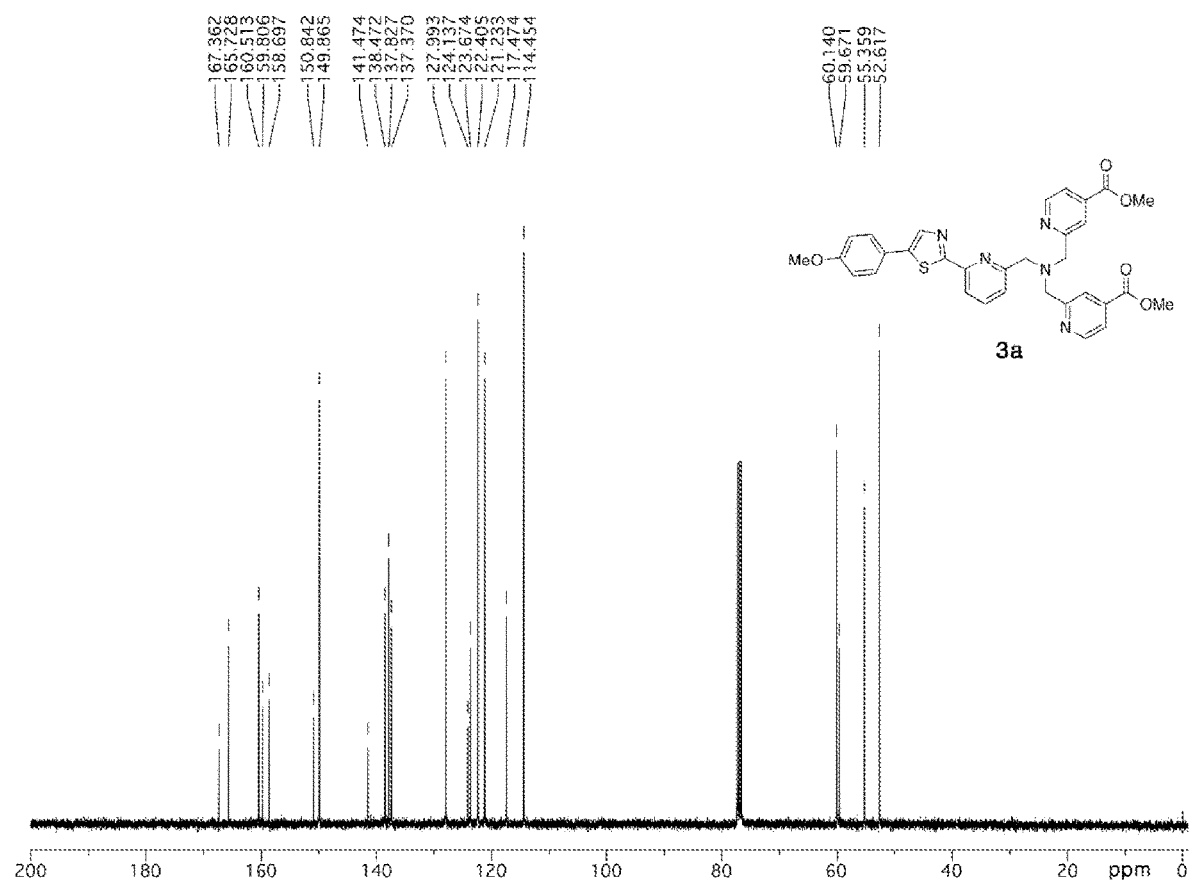
Figure 8:
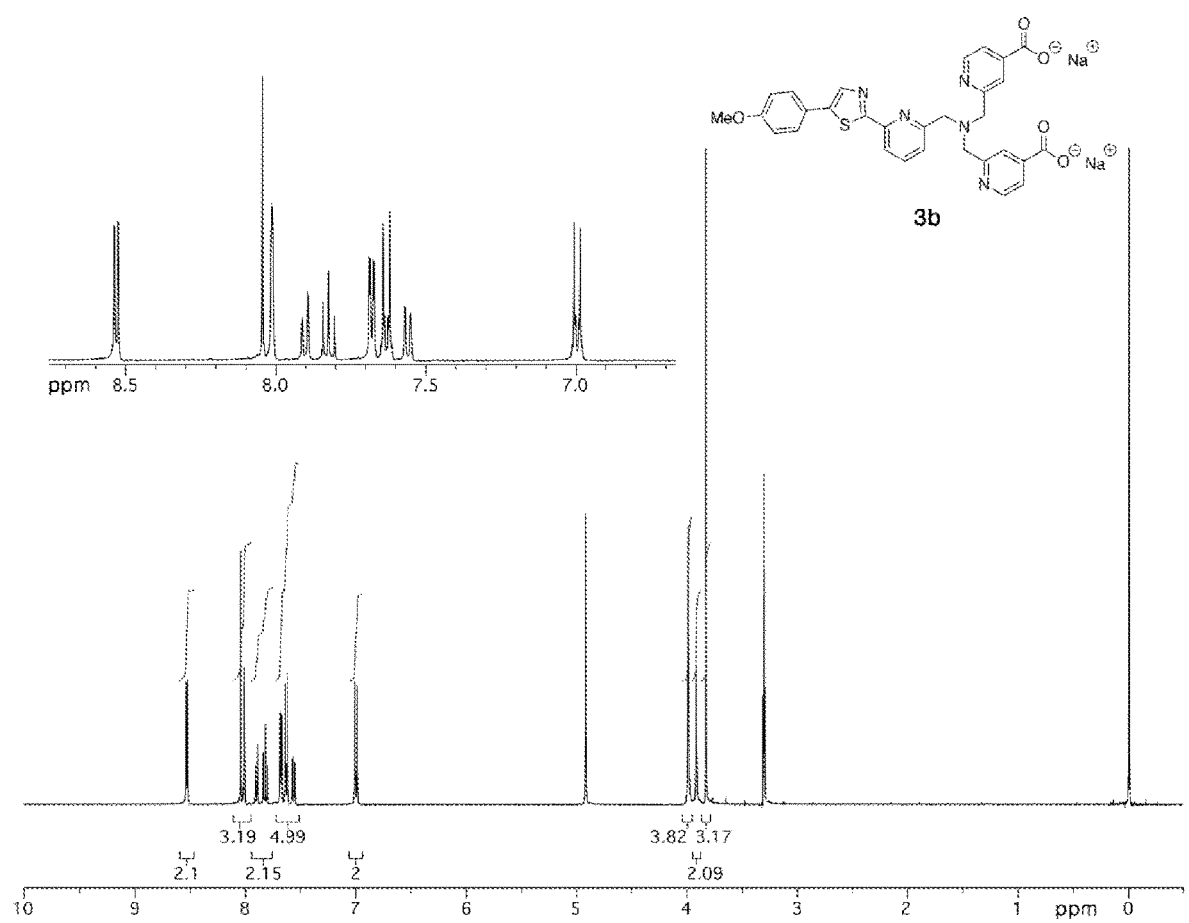
FIG. 8. NMR spectra of compound 3b, including $^1$H NMR (DMSO-d6, 400 MHz) and $^{13}$C NMR (DMSO-d6, 100 MHz).
Figure 8:
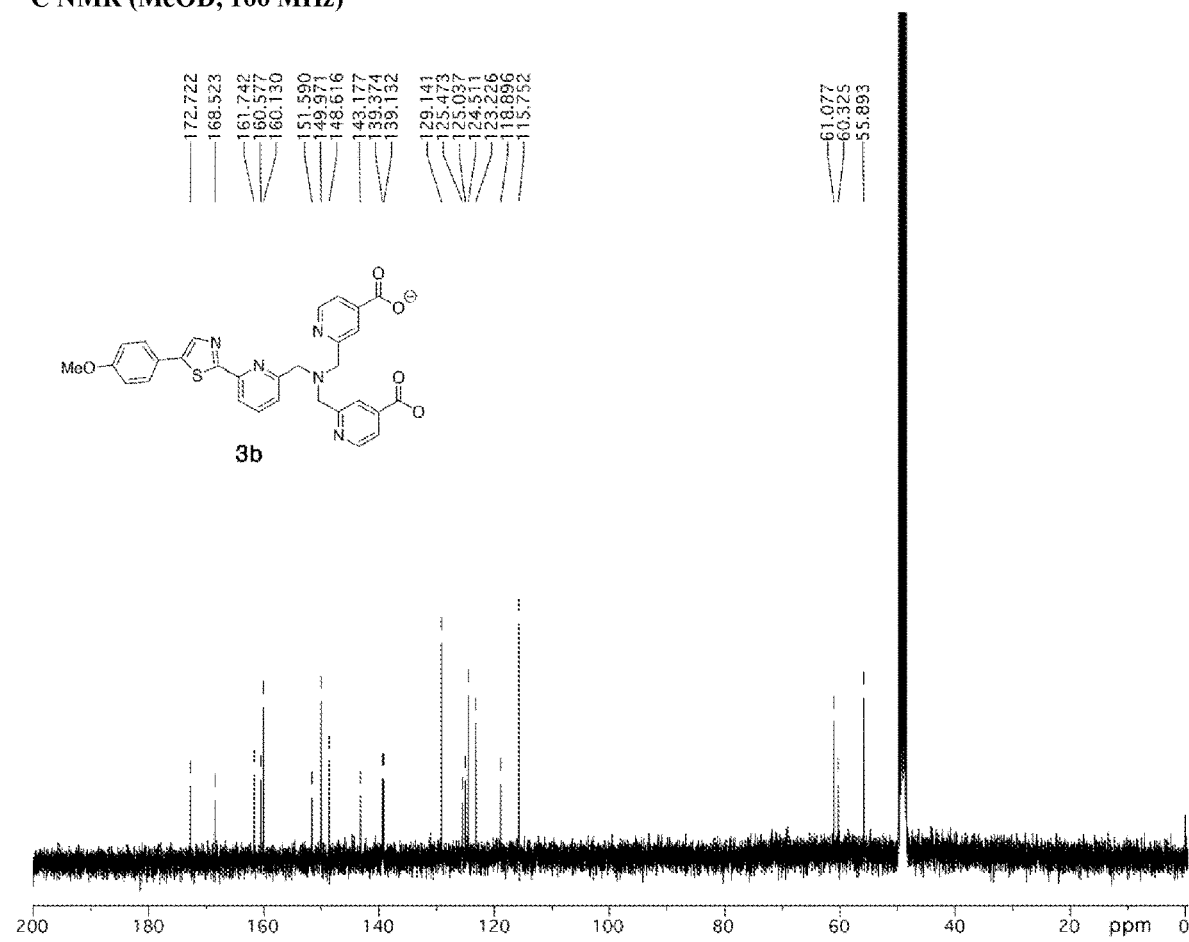

Suppression of excited-state protonation. Fluorimetric analysis of 3a (methyl ester) in liposomes displayed more balanced emission intensities of the free and metal-bound fluorophore compared to the corresponding dicarboxylate (3b), despite excitation at the isosbestic point to ensure that the emission intensities directly reflect the quantum yields of both species in solution (FIG. 8). The discrepancy between 3a (FIG. 7) and 3b (FIG. 8) can be attributed to a substituent effect between the para-methyl ester (Hammett parameter $\sigma_p$=0.45) and the anionic carboxylate (Hammett parameter $\sigma_p$=0.0), with the more strongly electron-withdrawing methyl ester rendering the pyridine nitrogen less basic and thus less likely to be protonated at physiological pH. This observation furnished momentum to explore potential chelator moieties to replace the bis(2-pyridylmethyl)amine that would still permit the selective binding of Zn(II).

The inventors' search for heteroaromatic groups whose pKa's were significantly lower than the pKa of pyridine led them to analyze the effect of substituting the pyridine rings with pyrimidine (pK$_a$=1.3). Despite the inherent correlation between binding affinity and proton basicity, the statistical effect that is associated with the likelihood of Zn(II) binding to either of the two pyrimidine nitrogens surprisingly provides an additional 0.6 log units (0.3 log units per pyrimidine ring) to the stability constant. Assembly of the 2-thiazolyl fluorophore containing the bis(2-pyrimidylmethyl)amine chelating group led to a 20% increase in the fluorescence quantum yield of the free form from 0.25 to 0.45. Deuterium-isotope studies of the ligand in identical D$_2$O and H$_2$O buffers showed no change in fluorescence intensity or profile. In addition, steady-state fluorescence studies of the free- and Zn(II)-bound forms revealed a nearly completely balanced emission response, corroborating the eradication of the ESPT phenomenon.

Figure 3A:
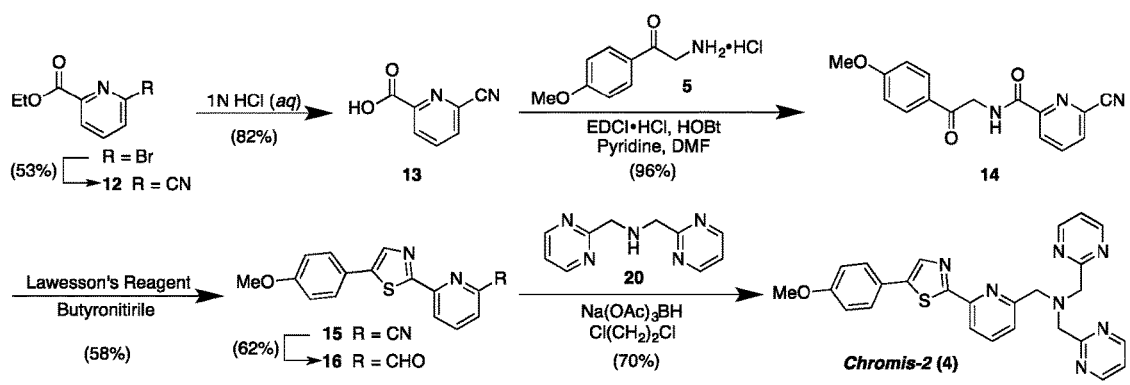
FIG. 3A-3B. Synthesis and crystallographic representation of chromis-2.
Figure 3B:
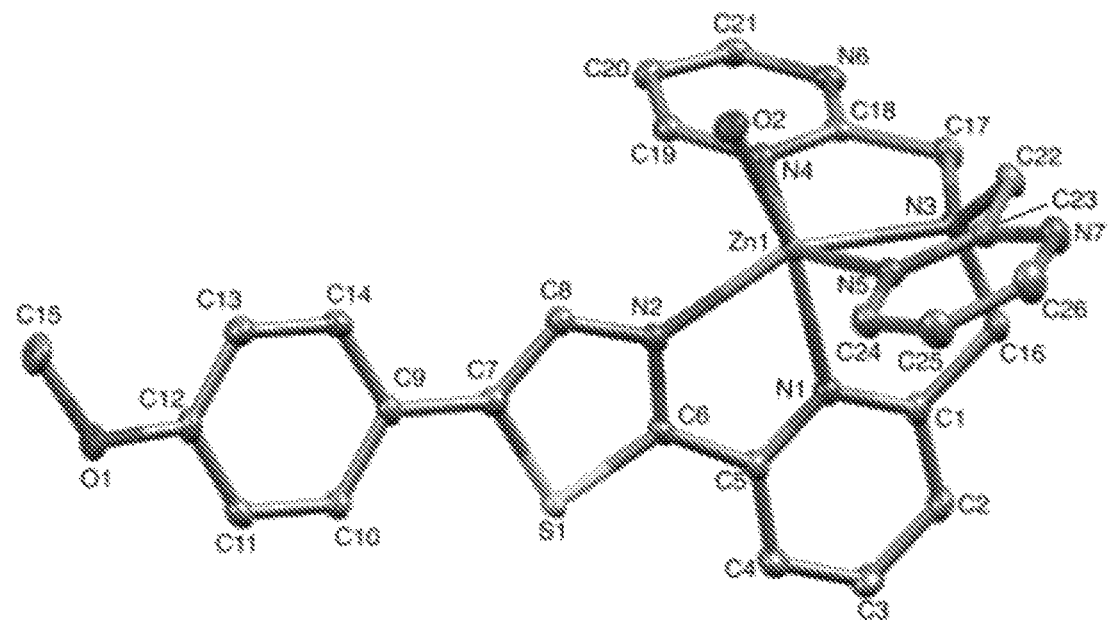

Synthesis and x-ray crystallography. Chromis-2 was synthesized in 7 steps from commercially available starting materials with an overall yield of 10% (See FIG. 3A and Example 2 for additional details). Beginning with ethyl 6-bromopicolinate, a Rosenmund-von Braun reaction with cuprous cyanide in pyridine substituted the bromine with a nitrile, followed by selective hydrolysis of the ethyl ester 12 in boiling 1 N HCl$_{(aq)}$ to afford the corresponding carboxylic acid 13. Condensation of the nitrile acid with 2-amino-4'-methoxyacetophenone hydrochloride yielded amide 14, which underwent a thionation-cyclization reaction to the corresponding thiazole nitrile 15 using Lawesson's reagent. The nucleophilic nature of Lawesson's reagent coupled with the electron-withdrawing capacity of the 2-cyanopyridine moiety created a time-dependent functional group interconversion of the expected thiazole nitrile product to a thioamide, which was converted back to the nitrile by reacting the crude isolated mixture with potassium permanganate in acetone. Upon recrystallization of the nearly pure nitrile, lithium diisobutyl-t-butoxyalumunium hydride (LDBBA) was used to selectively reduce the nitrile to the aldehyde 16 at room temperature. Although DIBAL is often used for reductions of nitriles to aldehydes, reaction with DIBAL afforded exclusively the doubly reduced amine, suggesting that the pyridine nitrogen could act as a Lewis base for coordinating the aluminum and augmenting its local reactivity. Synthesis of the bis(2-pyrimidinylmethyl)amine chelator was accomplished by a one-pot dimerization of 2-pyrimidinecarbonitrile in 1:1 dioxane:water, which proceeded through a Pd/C-catalyzed hydrogenation of the nitrile to the primary amine, followed by a reductive amination via catalytic hydrogenation with the 2-pyrimidinecarboxaldehyde that was generated from an in situ acid-catalyzed hydrolysis of the partially hydrogenated imine intermediate. Using the aldehyde as a versatile scaffold for attaching metal-binding ligands, reductive amination with bis(2-pyrimidylmethyl)amine afforded chromis-2 to be used directly for cell microscopy and solution chemistry.

Figure 9:
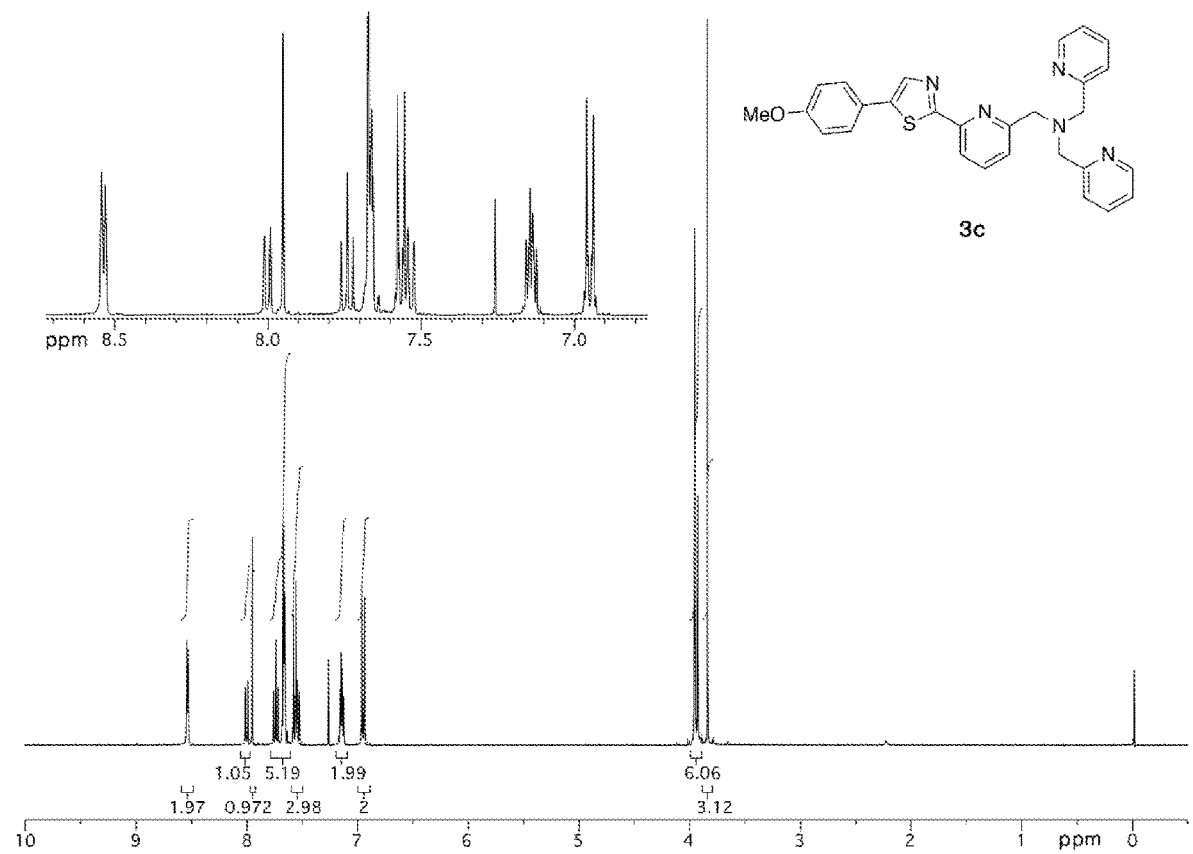
FIG. 9. NMR spectra of compound 3c, including $^1$H NMR (DMSO-d6, 400 MHz) and $^{13}$C NMR (DMSO-d6, 100 MHz).
Figure 9:
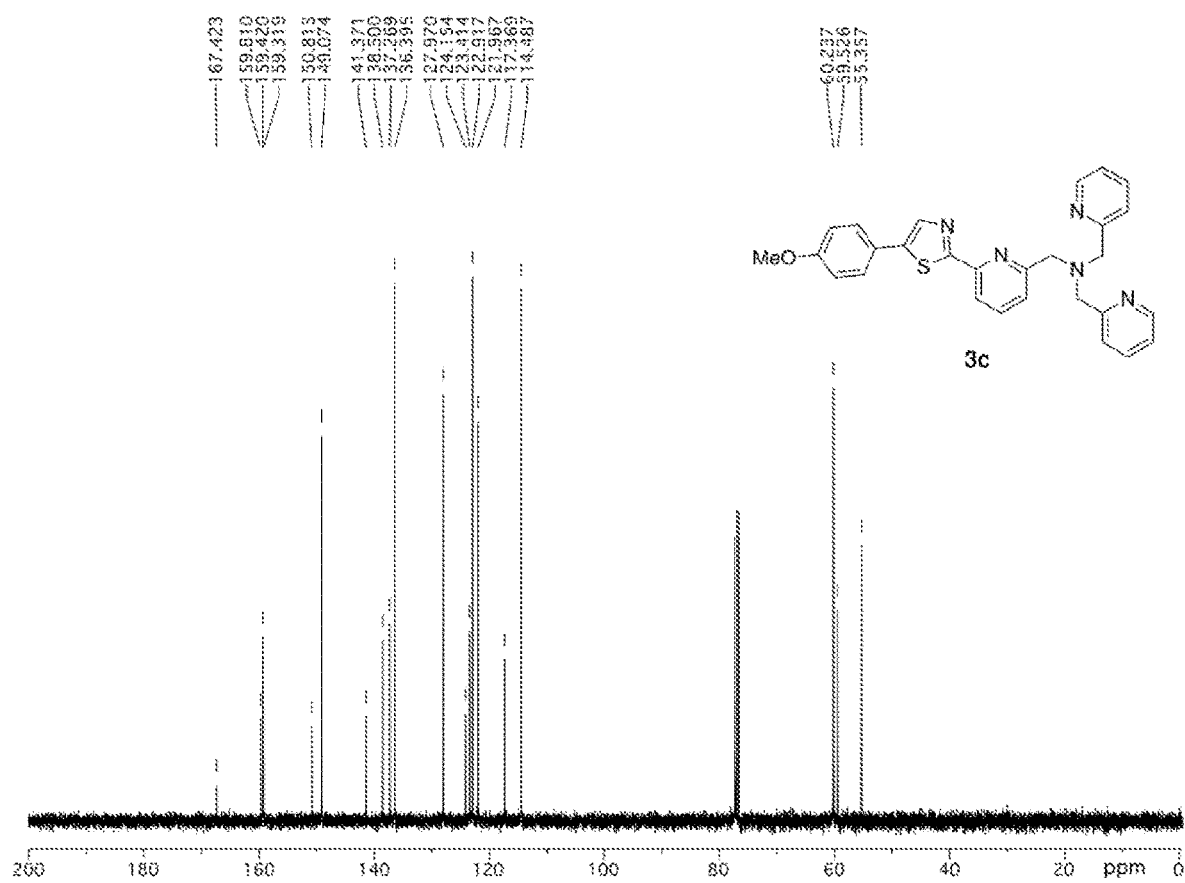
Figure 10:
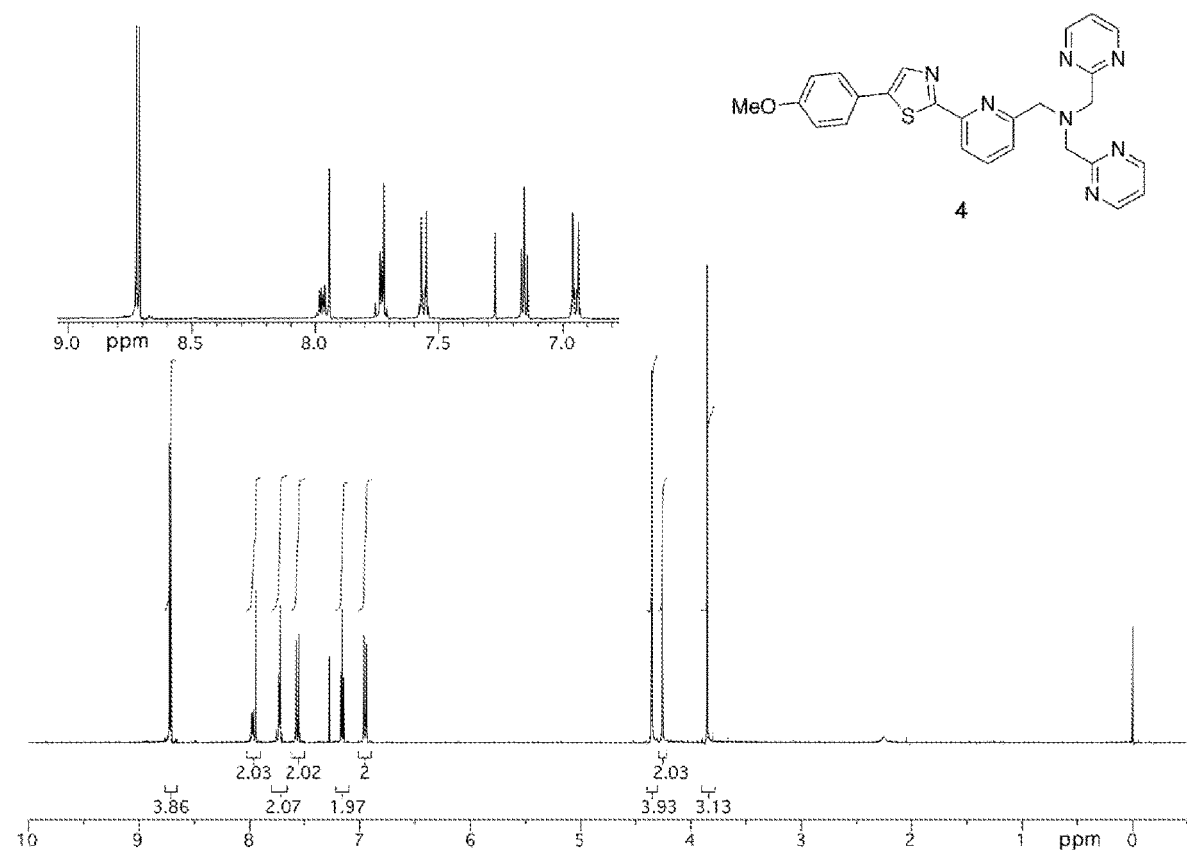
FIG. 10. NMR spectra of chromis-2 (compound 4), including $^1$H NMR (DMSO-d6, 400 MHz) and $^{13}$C NMR (DMSO-d6, 100 MHz).
Figure 10:
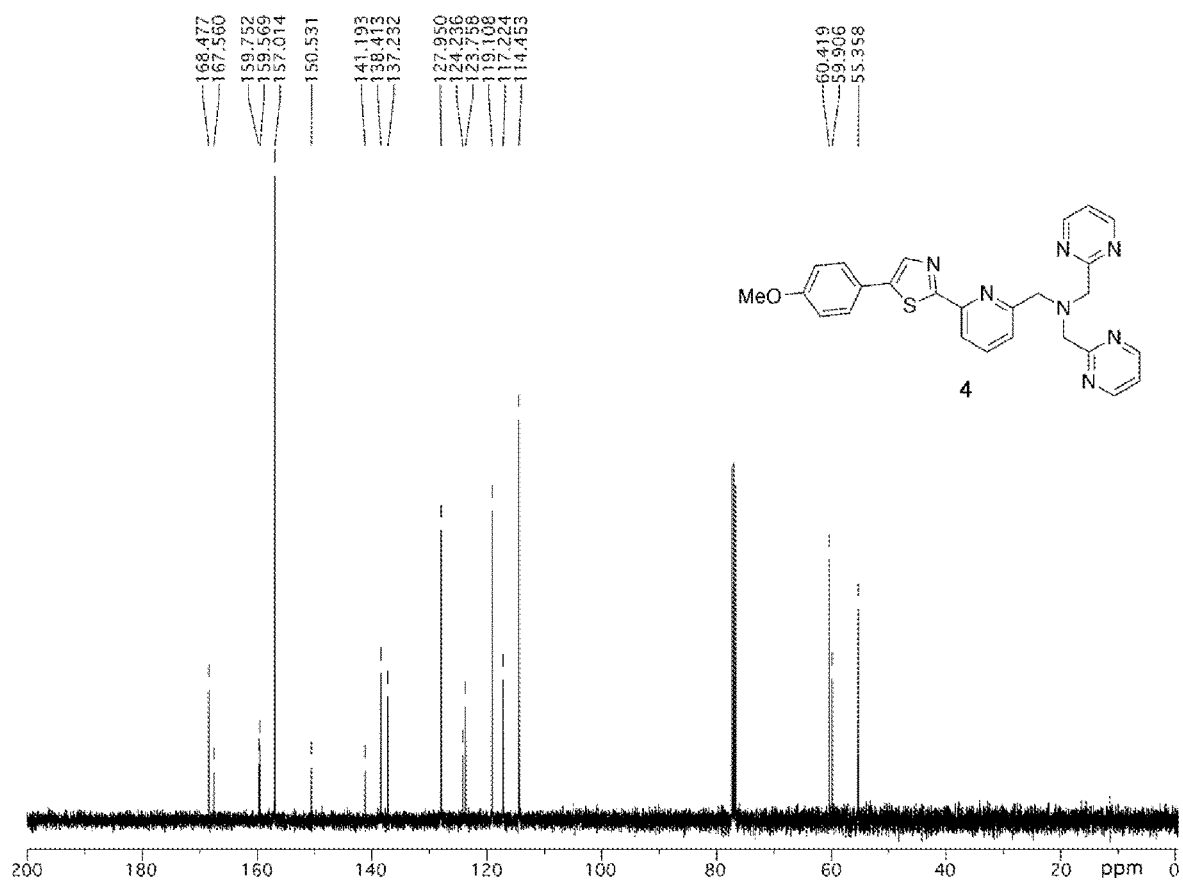
Figure 11:
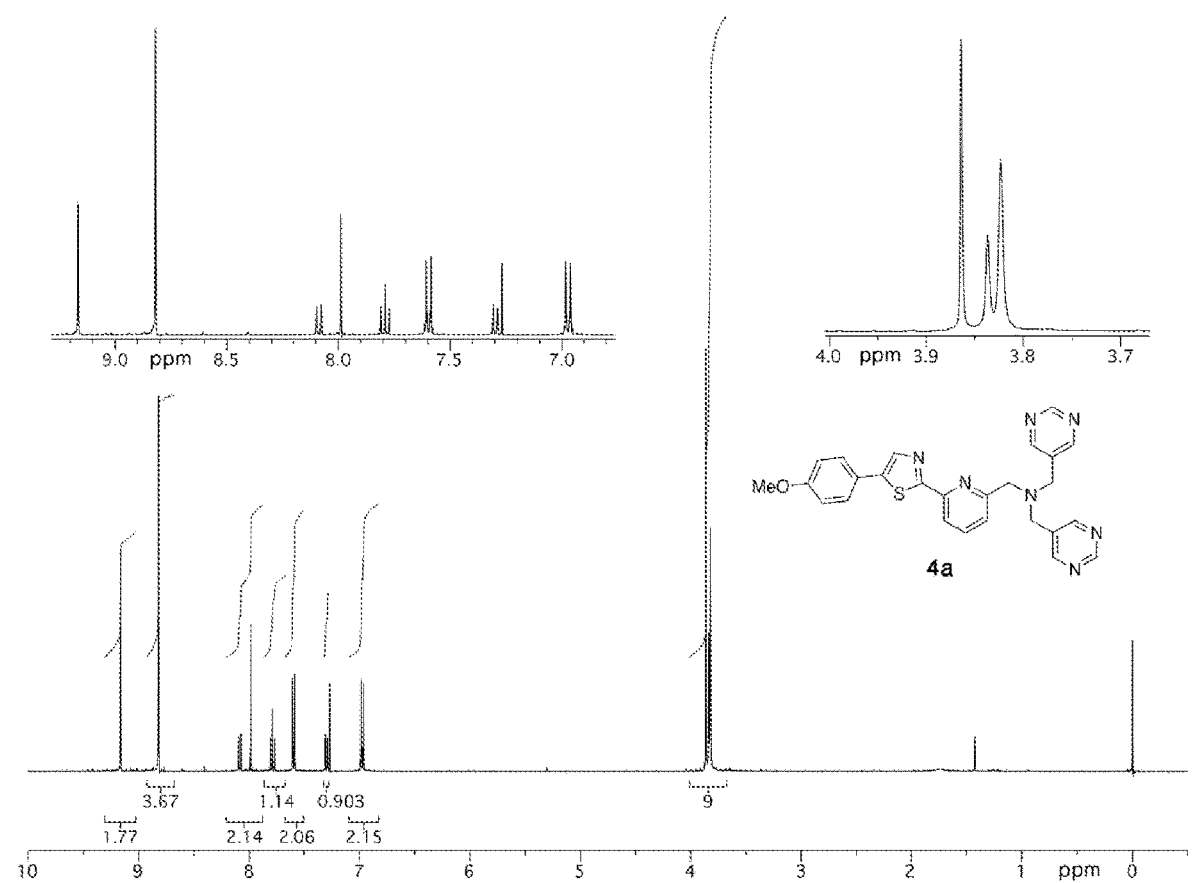
FIG. 11. NMR spectra of compound 4a, including $^1$H NMR (DMSO-d6, 400 MHz) and $^{13}$C NMR (DMSO-d6, 100 MHz).
Figure 11:
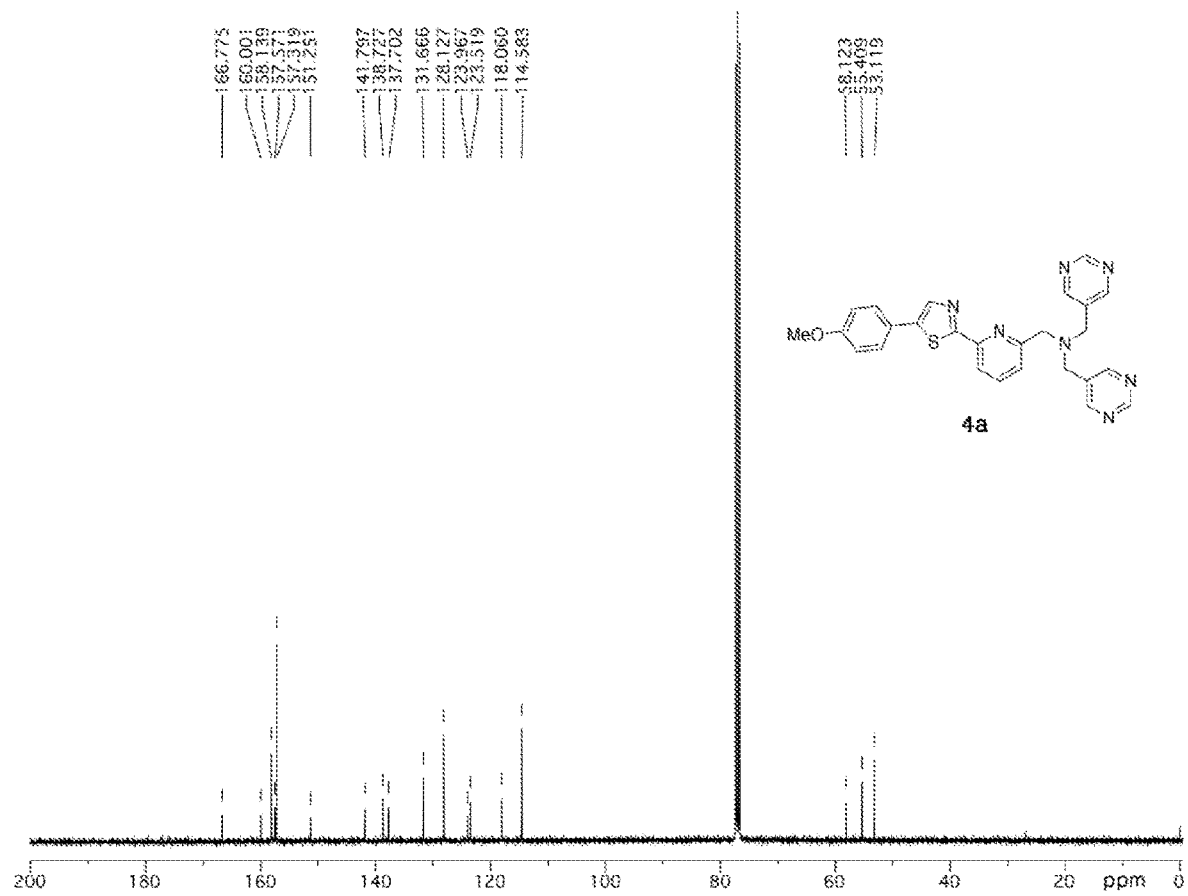

The isomerization of the pyridyl acceptor moiety to the 2-thiazolyl position engages the thiazole nitrogen in Zn(II) coordination to permit the formation of a binary pentavalent ligand-metal complex. However, when the inventors crystallized the chromis-2-Zn(II) complex, they observed the crystallization of a ternary complex, resulting in a hexacoordinate Zn(II) that adopts a slightly distorted octahedral geometry about the Zn(II) ion, with a water molecule coordinated to the Zn(II) in the axial position (FIG. 1B and Tables 1-4). When the inventors crystallized the Zn(II) complex of the unsubstituted bispicolylamine-containing fluorophore 3c (FIG. 9) to directly compare to chromis-2 (FIG. 10), they observed a binary ligand-metal complex with a pentavalent Zn(II), suggesting that the less basic pyrimidine nitrogens permit the formation of an metal complex with higher coordination numbers about the Zn(II) ion, as is the case with [Zn(OH$_2$)$_6$]$^{2+}$. The chromis-2-Zn(II) complex was crystallized in situ as the tetrafluoroborate adduct from a mixture of water and methanol to produce monoclinic crystals with the formula [(chromis-2).Zn(II)](BF$_4$)$_2$.2H$_2$O (Table 3).

TABLE 1

Crystal data and structure refinement for the Zn(II) complex of compound 3c [(compound 3c)Zn(II)](ClO$_4$)$_2$(H$_2$O).

| | |
|---|---|
| Empirical formula | C$_{28}$H$_{27}$Cl$_2$N$_5$O$_{10}$SZn |
| Formula weight | 761.87 |
| Temperature | 100(2) |
| Wavelength | MoKα (λ = 0.71073) |
| Crystal system | monoclinic |
| Space group | P2$_1$/c |
| Unit cell dimensions | a = 12.6948(4) Å, α = 90° |
| | b = 16.2339(5) Å, β = 91.625(3)° |
| | c = 15.1941(4) Å, γ = 90° |
| Volume | 3130.03(16) Å$^3$ |
| Z | 4 |
| Density (calculated) | 1.617 g/cm$^3$ |
| Absorption coefficient | 1.088 mm$^{-1}$ |
| F(000) | 1560.0 |
| Crystal size | 0.40 × 0.37 × 0.18 mm |
| Theta range for data collection | 2.414 to 30.508° |
| Index ranges | −18 ≤ h ≤ 18, −23 ≤ k ≤ 23, −21 ≤ l ≤ 21 |
| Reflections collected | 27117 |
| Independent reflections | 9537 [R$_{int}$ = 0.0367, R$_{sigma}$ = 0.1483] |
| Refinement method | Full-matrix least-squares on F$^2$ |
| Data/restraints/parameters | 9537/251/465 |
| Goodness-of-fit on F$^2$ | 1.035 |
| Final R indices [I > 2sigma(I)] | R$_1$ = 0.0523, wR$_2$ = 0.1271 |
| R indices (all data) | R$_1$ = 0.0717, wR$_2$ = 0.1368 |
| Largest diff. peak and hole | 1.238/−0.538 e.Å$^{-3}$ |

TABLE 2

Selected bond lengths and bond angles for the Zn(II) complex
of compound 3c [(compound 3c)Zn(II)](ClO$_4$)$_2$(H$_2$O)

| 3c | | 3c | |
|---|---|---|---|
| N1—Zn1 | 2.044(2) | N1—Zn1—N4 | 117.03(8) |
| N2—Zn1 | 2.1218(19) | N1—Zn1—N5 | 123.19(8) |
| N3—Zn1 | 2.246(2) | N4—Zn1—N5 | 109.57(8) |
| N4—Zn1 | 2.037(2) | N1—Zn1—N2 | 78.99(8) |
| N5—Zn1 | 2.039(2) | N2—Zn1—N4 | 112.37(8) |
| | | N2—Zn1—N5 | 111.70(8) |
| | | N1—Zn1—N3 | 76.83(8) |
| | | N3—Zn1—N4 | 81.01(8) |
| | | N3—Zn1—N5 | 80.33(8) |
| | | N2—Zn1—N3 | 155.72(8) |

TABLE 3

Crystal data and structure refinement for the Zn(II)
complex of ligand 4 [(chromis-2)Zn(II)](BF$_4$)$_2$(H$_2$O)$_2$

| | |
|---|---|
| Empirical formula | C$_{26}$H$_{27}$B$_2$F$_8$N$_7$O$_3$SZn |
| Formula weight | 756.59 |
| Temperature | 100(2) |
| Wavelength | CuKα (λ = 0.154184) |
| Crystal system | monoclinic |
| Space group | P2$_1$/c |
| Unit cell dimensions | a = 9.86710(10) Å    α = 90° |
| | b = 19.3141(2) Å    β = 100.6150(10)° |
| | c = 16.4920(2) Å    γ = 90° |
| Volume | 3089.16(6) Å$^3$ |
| Z | 4 |
| Density (calculated) | 1.627 g/cm$^3$ |
| Absorption coefficient | 2.564 mm$^{-1}$ |
| F(000) | 1536.0 |
| Crystal size | 0.265 × 0.246 × 0.206 mm |
| Theta range for data collection | 7.12 to 144.336° |
| Index ranges | −12 ≤ h ≤ 11, −23 ≤ k ≤ 23, −20 ≤ l ≤ 20 |
| Reflections collected | 19414 |
| Independent reflections | 5977 [R$_{int}$ = 0.0241, R$_{sigma}$ = 0.0223] |
| Refinement method | Full-matrix least-squares on F$^2$ |
| Data/restraints/parameters | 5977/6/450 |
| Goodness-of-fit on F$^2$ | 1.049 |
| Final R indices [I > 2sigma(I)] | R$_1$ = 0.0295, wR$_2$ = 0.0765 |
| R indices (all data) | R$_1$ = 0.0316, wR$_2$ = 0.0777 |
| Largest diff. peak and hole | 0.63/−0.66 e.Å$^{-3}$ |

TABLE 4

Selected bond lengths and bond angles for the Zn(II)
complex of compound 4 [(chromis-2)Zn(II)](BF$_4$)$_2$(H$_2$O)$_2$.

| Chromis-2 (compound 4) | | Chromis-2 (compound 4) | |
|---|---|---|---|
| N1—Zn1 | 2.1137(13) | N2—Zn1—N4 | 105.19(5) |
| N2—Zn1 | 2.1690(14) | N2—Zn1—N5 | 108.78(5) |
| N3—Zn1 | 2.3520(13) | N3—Zn1—N4 | 77.10(5) |
| N4—Zn1 | 2.1009(13) | N3—Zn1—N5 | 76.56(5) |
| N5—Zn1 | 2.0937(13) | N1—Zn1—N2 | 76.23(5) |
| O2—Zn1 | 2.1096(11) | N1—Zn1—N3 | 75.53(5) |
| | | N1—Zn1—N4 | 101.78(5) |
| | | N1—Zn1—N5 | 93.13(5) |
| | | N2—Zn1—O2 | 91.10(5) |
| | | N3—Zn1—O2 | 117.38(5) |
| | | N4—Zn1—O2 | 86.95(5) |
| | | N5—Zn1—O2 | 85.42(5) |
| | | N1—Zn1—O2 | 166.08(5) |
| | | N2—Zn1—N3 | 151.51(5) |
| | | N4—Zn1—N5 | 145.27(5) |

Figure 4A:
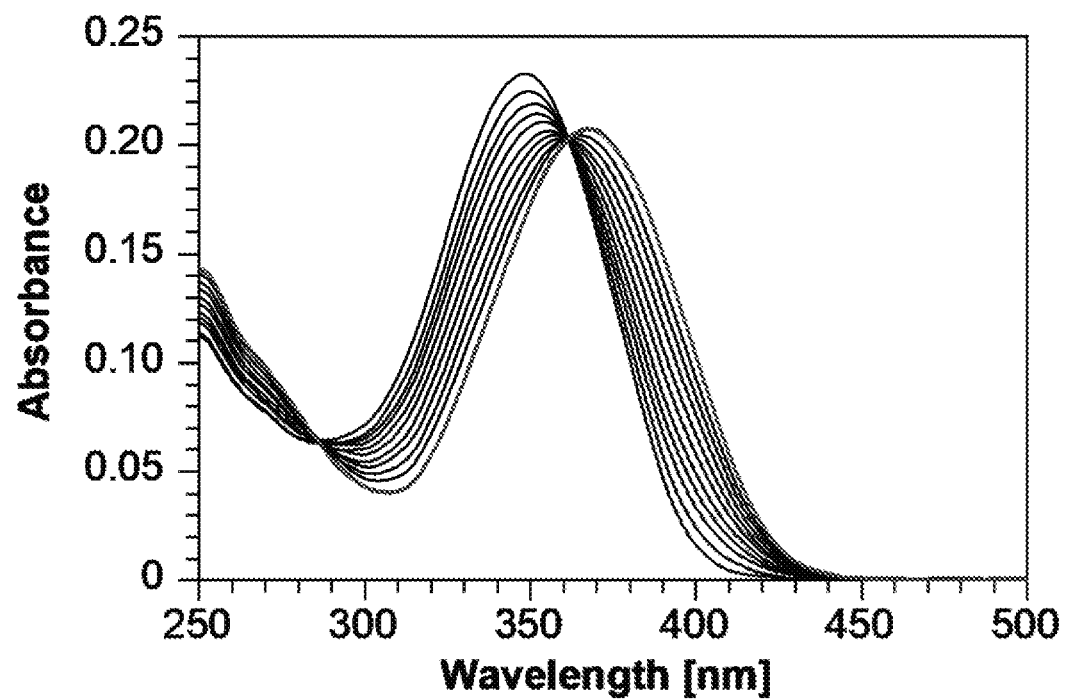
FIG. 4A-4C. Steady-state absorption and emission properties of chromis-2 (4).
Figure 4B:
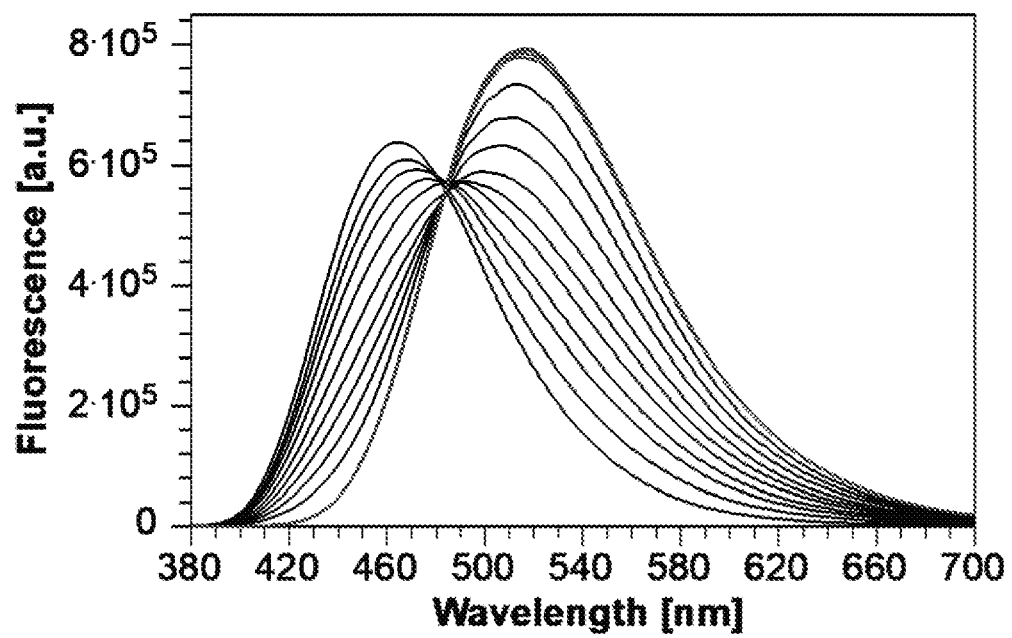

Spectral properties and solution chemistry. To avoid nuisances that can occur due to aggregation of these fluorophores, especially when concentrated stock solutions of the chromophores are diluted to micromolar concentrations into aqueous buffer, spectral overlap experiments of chromis-2 conducted under dilute and concentrated conditions confuted any potential aggregation in the concentration range used for the probe, despite the lack of water-solubilizing carboxylic acids found in chromis-1 and compound 3b. Chromis-2 exhibits a large bathochromic shift in both the absorption and emission upon binding of Zn(II), and titrations with Zn(II) producing a sharp saturation at equimolar concentrations of probe and metal demonstrate a 1:1 binding stoichiometry (FIGS. 4A and 4B). Upon binding of Zn(II) to chromis-2, the absorbance maximum at 348 nm for the free form (ε=23,400 M$^{-1}$.cm$^{-1}$) undergoes a 20-nm spectral shift to 368 nm as the absorbance maximum of the Zn(II)-bound form (ε=20,800 M$^{-1}$.cm$^{-1}$), consistent with an increase in intramolecular charge transfer of the molecule. In parallel with the absorption, the emission maximum of free chromis-2 undergoes a 50-nm shift from 465 nm to 515 nm for the Zn(II)-saturated form. Comparing the ratiometric emission shift to that of chromis-1, the free form of chromis-2 is blue-shifted by 19 nm, whereas the Zn(II)-saturated form is blue-shifted by only 5 nm. Isomerization of the pyridyl acceptor moiety from the 4-position (chromis-1) to the 2-position (3b) decreased the quantum yield from 0.32 to 0.25 for the free probe, whereas the Zn(II)-saturated probe's quantum yield decreased from 0.71 to 0.61. The decrease in the quantum yield can be attributed to the spectral differences in the absorbance profile, as the absorbance for chromis-1 increases upon saturation with Zn(II), whereas the absorbance for compound 3b decreases when bound to Zn(II) relative to the free form. Substitution of the bis(2-pyridylmethyl)amine chelator for the bis(2-pyrimidylmethyl)amine nearly doubled the quantum yield of the free form from 0.25 to 0.45, yet the Zn(II)-saturated form increased only 8% from 0.61 to 0.69. The 20% increase in the quantum yield of the free form can be accredited to the suppression of ESPT-mediated quenching.

Figure 4C:
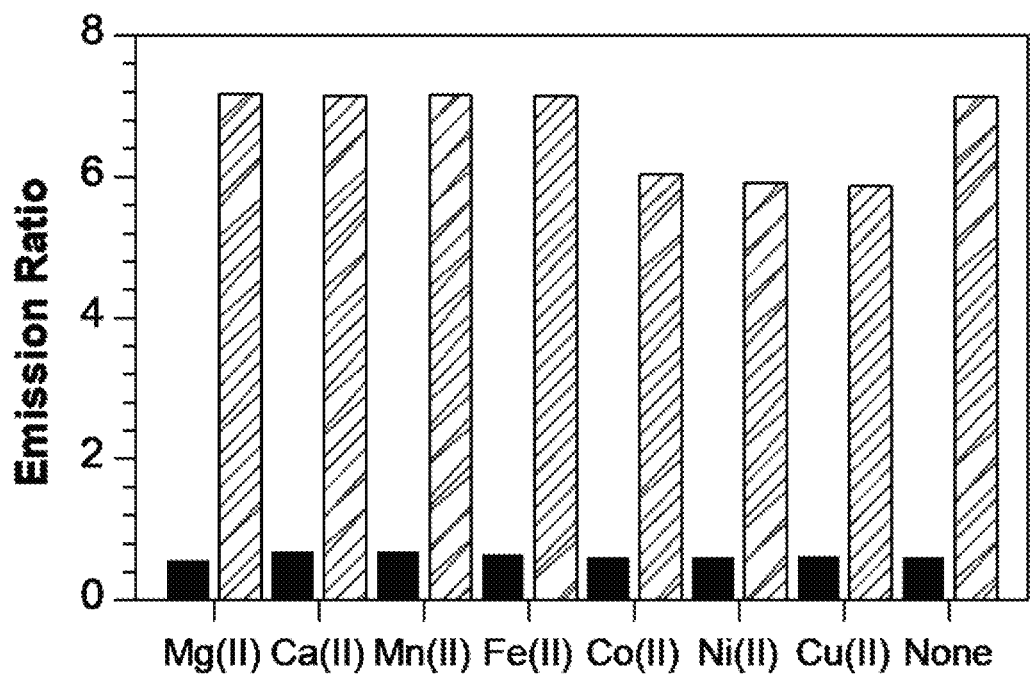

As illustrated in FIG. 4c, supplementation of chromis-2 with biologically relevant divalent transition metal ions, except Zn(II) and Mn(II), lead to a quantitative quenching of the probe but did not elicit a change in the ratiometric response. Despite the additional nitrogen donor from the thiazole, however, the lower affinity manifested by the less basic pyrimidines of chromis-2 also resulted in partial fluorescence quenching with Mn(II), which was readily outcompeted by supplementation of 1 molar equivalent of Zn(II). Titration of chromis-2 with Mn(II) yielded a stability constant of log K$_{Mn(II)L}$=5.87±0.01, corresponding to an apparent dissociation constant of 1.36 μM. Addition of millimolar concentrations of Mg(II) to chromis-2 did not elicit a change in fluorescence, whereas addition of millimolar Ca(II) lead only to a slight increase of the fluorescence response chromis-2. To evaluate the selectivity chromis-2, the inventors measured the change in fluorescence at 80% fractional saturation of the probe, and the remaining 20% of the probe was saturated with Zn(II) to elicit a ratiometric response that corresponds to the ratio response of the Zn(II)-saturated fluorophore in the molar ratio titration, a technique that the inventors introduced with chromis-1.

TABLE 5

One and two-photon photophysical properties of chromis-2 (compound 4) in aqueous buffer at pH 7.0.[a]

| | chromis-2 (compound 4) | [chromis-2-Zn(II)] |
|---|---|---|
| Abs $\lambda_{max}$ (nm)[b] | 348 | 368 |
| $\varepsilon (10^4\ M^{-1}cm^{-1})$[c] | 2.34 | 2.08 |
| $\delta_{max}$ (GM)[d] | # | # |
| Em $\lambda_{max}$ (nm)[e] | 465 | 515 |
| $\Phi_F$[f] | 0.45 | 0.69 |

[a]10 mM PIPES, 0.1M KCl, 25° C.

[b]lowest-energy band of the one-photon absorption spectrum.

[c]molar extinction coefficient at $_{max}$.

[d]two-photon absorption cross section.

[e]maximum fluorescence emission.

[f]fluorescence quantum yield, referenced to quinine sulfate ($\Phi_F$ = 0.546).

Despite the thiazole's propensity to engage in coordination to Zn(II), as well as the statistical effect associated with Zn(II) binding to either of the two pyrimidine nitrogens, the significantly reduced basicity of chromis-2's pyrimidine rings results in an affinity that is comparable to chromis-1 ester but significantly lower than chromis-1 acid. To reliably determine the binding affinity of chromis-2, the inventors performed spectrophotometric and fluorimetric titrations in the presence of EGTA as a competing ligand (log $K_{EGTA.Zn(II)}$=9.20 at pH 7.0, ρ=0.1 M, 25° C.). Non-linear least-squares fitting of either the spectrophotometric or fluorimetric data provided an apparent stability constant of 8.80±0.02, corresponding to an apparent dissociation constant of 1.59 nM.

Example 2. Synthesis of Chromis-2

Materials and Reagents.

2-amino-4'-methoxyacetophenone (5) and 2-cyanoisonicotinic acid (17) were synthesized according to previously published literature procedures. Picolinic acid (Chem-Impex Int'l Inc.), isonicotinic acid (Eastman), ethyl 6-bromo-picolinate (Combi-Blocks, Inc.), 2-pyrimidinecarbonitrile (Oxchem Corp.) and 5-pyridinecarbaldehyde (Ark Pharm, Inc.) were purchased commercially and used without further purification. Flash chromatography purification was performed on general purpose silica gel (60 Å pore size, 250 mesh, Sorbent Technologies). NMR: 1H NMR spectra were recorded at 400 MHz at ambient temperature (20-23° C.), unless stated otherwise, and referenced to an internal TMS standard (0 ppm) for all solvents except $D_2O$, which was referenced to externally added sodium 3-trimethylsilylpropionate-2,2,3,3-$d_6$ (0 ppm). 13C spectra were acquired at 100 MHz and referenced to the known chemical shift of the solvent peak ($CDCl_3$: 77.0 ppm; DMSO-$d_6$: 39.5 ppm; $CD_3OD$: 49.0 ppm; Acetone-$d_6$: 206.3, 29.8 ppm), excluding $D_2O$, which was referenced to sodium 3-trimethylsilyl-propionate-2,2,3,3-$d_6$ (0 ppm). Mass spectra were recorded by the Georgia Tech Mass Spectrometry Facility.

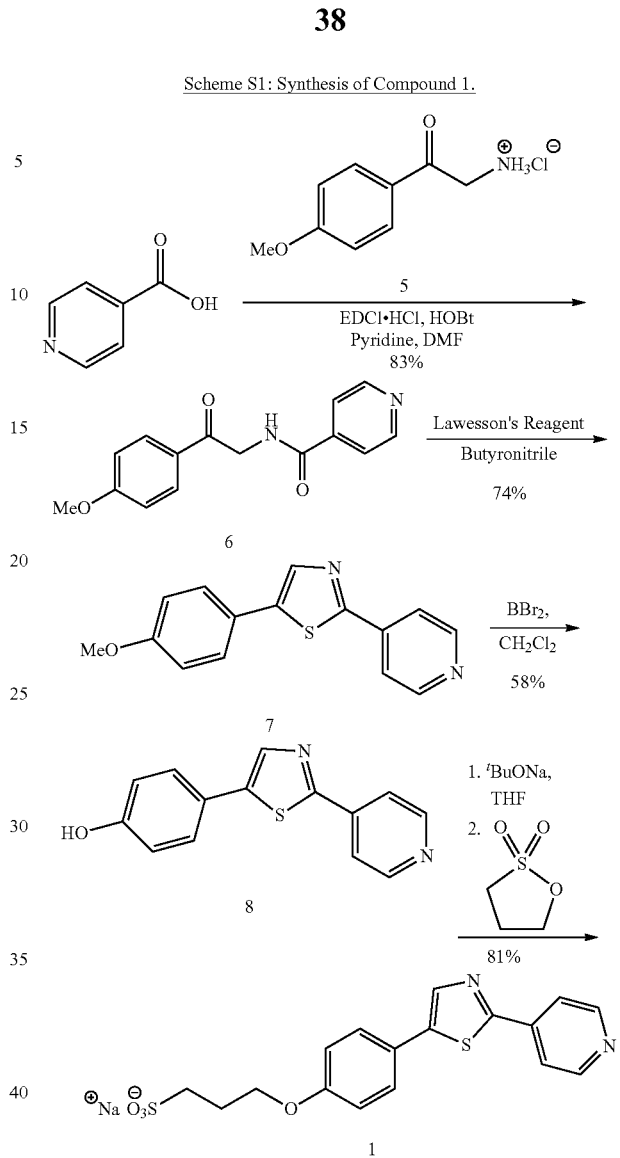

Scheme S1: Synthesis of Compound 1.

N-(2-(4-methoxyphenyl)-2-oxoethyl)isonicotinamide (compound 6). A 250 mL round bottom flask equipped with a stir bar was charged with 2-amino-4'-methoxyacetophenone hydrochloride (1.1 eq., 4.96 mmol, 1.00 g), picolinic acid (1 eq., 4.51 mmol, 555 mg), EDCI.HCl (1.5 eq., 6.77 mmol, 1.30 g), and HOBt (0.5 eq., 2.26 mmol, 305 mg). The contents were dissolved in DMF (15 mL), pyridine (1 eq., 4.51 mmol, 0.363 mL) was added to the reaction solution via a syringe, and the solution was allowed to stir magnetically overnight. The product was crystallized from the solution by the slow addition of 60 mL of di$H_2O$, after which the contents of the flask were filtered through a glass frit, washed with cold di$H_2O$, and dried over vacuum to afford pure 6 as a white crystalline solid. Yield: 1.01 g (3.75 mmol, 83%). ¹H NMR ($CDCl_3$, 400 MHz) δ 3.91 (s, 3H), 4.90 (d, J=4.2 Hz, 2H), 7.01 (d, J=9.0 Hz, 7.49 (s, 1H), 7.73 (dd, J=4.5, 1.5 Hz, 2H), 8.01 (d, J=9.0 Hz, 2H), 8.79 (d, J=4.9 Hz, 2H). ¹³C NMR ($CDCl_3$, 100 MHz) δ 46.3, 55.5, 114.1, 121.0, 127.0, 130.3, 141.0, 150.5, 163.4, 165.3, 192.0. EI-MS m/z 270 ([M]⁺, 5%), 241 (45%), 135 (100%), 77 (20%). EI-HRMS m/z calc'd for $C_{15}H_{14}N_2O_3$ 270.1006, found 270.1004.

5-(4-methoxyphenyl)-2-(pyridin-4-yl)thiazole (7). To an oven-dried 2-neck 100 mL round bottom flask equipped with a stir bar was added isonicotinamide 6 (1 eq., 3.36 mmol, 908 mg) and Lawesson's Reagent (1.3 eq., 4.37 mmol, 1.77 g). The flask was connected to a reflux apparatus, and using a glass frit connected to the top of the reflux condenser, the system was flushed with argon for several minutes to remove moisture. Using an argon-filled syringe, butryonitrile (15 mL, dried over 0.4 Å molecular sieves and filtered) was added through the top of the reflux condenser. The flask was lowered into an oil bath at 140° C. and allowed to magnetically stir under reflux for 30 min. After cooling to room temperature, saturated NaHCO$_3$(aq) solution (2 mL) was added to the deep red solution under stirring, and the mixture was diluted with ethyl acetate (40 mL), transferred to a separatory funnel, and washed with additional 5% (w/v) NaOH (aq) and brine. The organic layer was dried over MgSO$_4$, filtered, and concentrated under reduced pressure to afford a yellow solid residue. The crude solid was recrystallized from a 1:1 mixture of 2,2,4-trimethylpentane:toluene, collected by suction filtration, washed with hexanes, and dried under vacuum to afford 7 as an pale-yellow solid. Yield: 670 mg (2.50 mmol, 74%). $^1$H NMR (CDCl$_3$, 400 MHz) δ 3.83 (s, 3H), 6.94 (d, J=8.8 Hz, 2H), 7.54 (d, J=8.8 Hz, 2H) 7.77 (dd, J=4.6, 1.6, 2H), 7.97 (s, 1H), 8.69 (dd, J=4.6, 1.6 Hz, 2H). $^{13}$C NMR (CDCl$_3$, 100 MHz) δ 55.3, 114.6, 119.8, 123.2, 128.1, 138.8, 140.3, 141.3, 150.5, 160.1, 162.7. EI-MS m/z 268 ([M]$^+$, 100%), 253 (40%), 164 (23%), 149 (43%), 121 (33%), 77 (25%). EI-HRMS m/z calc'd for C$_{15}$H$_{12}$N$_2$OS 268.0670, found 268.0670.

4-(2-(pyridin-4-yl)thiazol-5-yl)phenol (8). Thiazole 7 (1 eq., 0.373 mmol, 100 mg) was added to a 10 mL round bottom flask equipped with a stir bar. The flask was sealed with a rubber septum, evacuated under high vacuum, and backfilled with argon. Via an argon-filled syringe, anhydrous dichloromethane (2 mL) was transferred to the flask to dissolve the starting material. The flask was then lowered into an ice bath at 0° C., and upon thermal equilibration (~10 minutes), boron tribromide (3 eq., 1.12 mmol, 1.12 mL of a 1 M solution in dichloromethane) was added drop-wise to the stirred solution. After stirring at 0° C. for 6 hours, the mixture was diluted with ethyl acetate (10 mL), quenched with diH$_2$O (10 mL), and the pH was adjusted to ~7 to neutralize the excess HBr using saturated aqueous NaHCO$_3$. The aqueous layer was then extracted with ethyl acetate (2×10 mL) and the combined organic layers were dried over MgSO$_4$, filtered, and concentrated to a blood orange solid. The crude solid was recrystallized from boiling methanol afford 8 as a burnt orange solid. Yield: 55 mg (0.216 mmol, 58%).%). $^1$H NMR (DMSO-d6, 400 MHz) δ 6.88 (d, J=8.6 Hz, 2H), 7.58 (d, J=8.6 Hz, 2H), 7.86 (dd, J=4.6, 1.5 Hz, 2H), 8.27 (s, 1H), 8.71 (dd, J=4.6, 1.5 Hz, 2H). 9.92 (s, 1H). $^{13}$C NMR (DMSO-d6, 100 MHz) δ 116.1, 119.6, 121.1, 128.2, 138.9, 139.6, 141.5, 150.7, 158.4, 161.4. EI-MS m/z 254 ([M]$^+$, 100%), 150 (73%), 121 (28%). EI-HRMS m/z calc'd for C$_{14}$H$_{10}$N$_2$OS 254.0514, found 254.0511.

3-(4-(2-(pyridin-4-yl)thiazol-5-yl)phenoxy)propane-1-sulfonate sodium salt (1). In a 10 mL round bottom flask equipped with stir bar, phenol 8 (1 eq., 0.236 mmol, 60 mg) was suspended in anhydrous THF (5 mL) under argon. Sodium tert-butoxide (NaO$^t$Bu, 1.0 eq., 0.236 mmol, 22.7 mg) was added to a separate, 4-mL vial sealed with a septum, and the vial was evacuated and backfilled with argon to remove potential moisture. The NaO$^t$Bu was suspended in anhydrous THF (2 mL), transferred to an argon-flushed syringe body, and the suspension was added drop-wise to the stirred solution containing phenol 8, which immediately precipitated the phenolate anion intermediate. After 30 minutes of stirring, 1,3-propanesultone (1.1 eq., 0.260 mmol, 32 mg) was added, and the solution stirred vigorously overnight. The THF was removed under reduced pressure to yield a crude yellow solid, which was purified by column chromatography (silica gel, 4:1 dichloromethane: methanol) to afford sulfonate 1 as a yellow crystalline solid. Yield: 76 mg (0.201 mmol, 81%). $^1$H NMR (DMSO-d6, 500 MHz) δ 2.02-2.1 (m, 2H), 2.61 (t, J=7.3 Hz, 2H), 4.17 (t, J=6.6 Hz, 2H), 7.09 (d, J=8.8 Hz, 2H), 7.73 (d, J=8.8 Hz, 2H), 7.93 (dd, J=4.5, 1.7 Hz, 2H), 8.38 (s, 1H), 8.75 (dd, J=4.5, 1.6 Hz, 2H). $^{13}$C NMR (DMSO-d6, 100 MHz) δ 25.2, 47.8, 66.9, 115.3, 119.7(2), 119.7(3), 128.1, 139.4(9), 139.5 (6), 141.0, 150.7, 159.3, 161.8. ESI-HRMS m/z calc'd for C$_{17}$H$_{15}$N$_2$O$_4$S$_2$ 375.0479, found 375.0478.

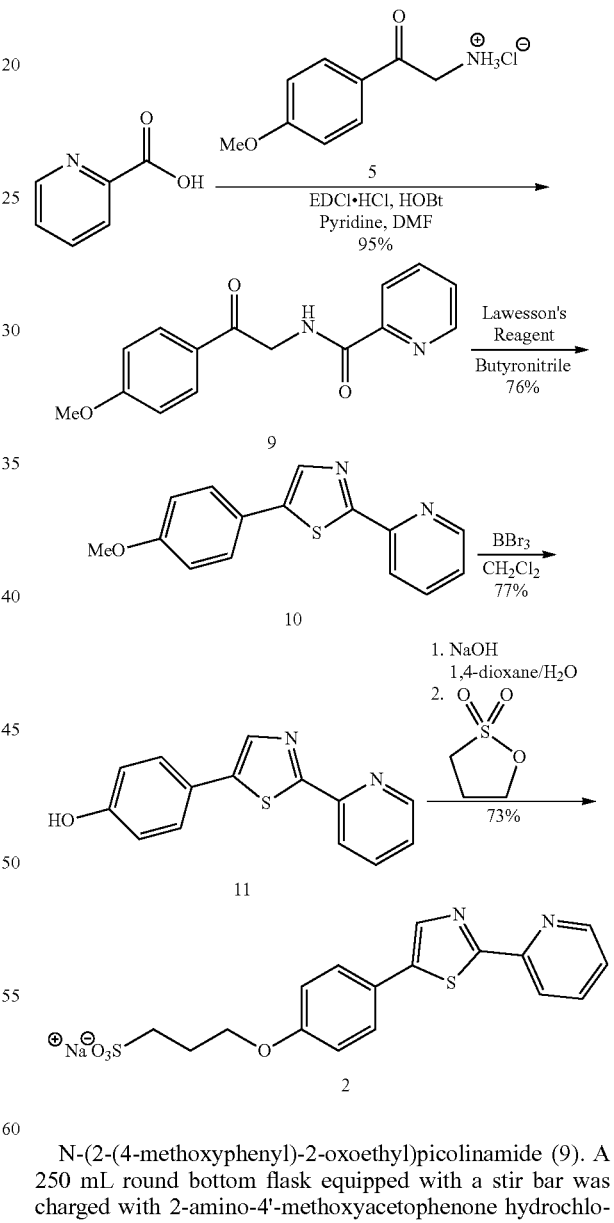

Scheme 2
Synthesis of compound 2.

N-(2-(4-methoxyphenyl)-2-oxoethyl)picolinamide (9). A 250 mL round bottom flask equipped with a stir bar was charged with 2-amino-4'-methoxyacetophenone hydrochloride (1.1 eq., 14.9 mmol, 3.00 g), picolinic acid (1 eq., 13.5 mmol, 1.66 g), EDCl.HCl (1.5 eq., 20.3 mmol, 3.89 g), and HOBt (0.5 eq., 6.76 mmol, 913 mg). After dissolving the contents in 40 mL of DMF, pyridine (1 eq., 13.5 mmol, 1.09 mL) was added to the reaction solution via a syringe, and the solution was allowed to stir magnetically overnight. The product was crystallized out of solution by the slow addition of 100 mL of diH$_2$O, after which it was filtered by suction filtration, washed with cold diH$_2$O, and dried over vacuum to afford 9 as a white crystalline solid. Yield: 3.48 g (12.9 mmol, 95%). $^1$H NMR (CDCl$_3$, 400 MHz) δ 3.88 (s, 3H), 4.92 (d, J=4.76 Hz, 2H), 6.98 (d, J=8.8 Hz, 2H), 7.45 (ddd, J=7.6, 4.8, 1.2 Hz, 1H), 7.85 (td, J=7.7, 1.0 Hz, 1H), 8.02 (d, J=8.8 Hz, 1H), 8.20 (dt, J=7.8, 1.0 Hz, 1H), 8.63 (ddd, J=4.8, 1.7, 0.9 Hz, 1H), 8.97 (s, 1H). $^{13}$C NMR (CDCl$_3$, 100 MHz) δ 45.9, 55.5, 114.0, 112.1, 126.2, 127.6, 130.2, 137.1, 148.3, 149.6, 164.1, 164.5, 192.1. EI-MS m/z 270 ([M]$^+$, 5%), 135 (100%), 78 (23%). EI-HRMS m/z calc'd for C$_{15}$H$_{14}$N$_2$O$_3$ 270.1004, found 270.1002.

5-(4-methoxyphenyl)-2-(pyridin-2-yl)thiazole (10). To an oven-dried 2-neck 100 mL round bottom flask equipped with a stir bar was added picolinamide 9 (1 eq., 6.66 mmol, 1.80 g) and Lawesson's Reagent (1.3 eq., 8.65 mmol, 3.50 g). The flask was connected to a reflux apparatus, and using a glass frit connected to the top of the reflux condenser, the system was flushed with argon for several minutes to remove moisture. Using an argon-filled syringe, butryonitrile (40 mL, dried over 0.4 Å molecular sieves and filtered) was added through the top of the reflux condenser. The flask was lowered into an oil bath at 140° C. and allowed to magnetically stir under reflux for 20 min. After cooling to room temperature, saturated NaHCO$_3$ (aq) solution (2 mL) was added to the deep red solution under stirring, and the mixture was diluted with ethyl acetate (40 mL), transferred to a separatory funnel, and washed with additional saturated NaHCO$_3$ and brine. The organic layer was dried over MgSO$_4$, filtered, and concentrated under reduced pressure to afford a yellow solid. The crude solid was purified via column chromatography (silica gel) using 7:2:1 hexanes:dichloromethane:MTBE as the elution solvent to afford pure 10 as a yellow solid. Yield: 1.36 g (5.07 mmol, 76%). $^1$H NMR (CDCl$_3$, 400 MHz) δ 3.83 (s, 3H), 6.94 (d, J=8.8 Hz, 2H), 7.29 (ddd, J=7.7, 5.0, 1.3 Hz, 1H), 7.56 (d, J=8.9 Hz, 2H), 7.78 (td, J=7.8, 1.7 Hz, 1H), 7.97 (s, 1H), 8.16 (dt, J=8.0, 1.0, 1H), 8.61 (ddd, J=4.9, 1.6, 0.9, 1H). $^{13}$C NMR (CDCl$_3$, 100 MHz) δ 55.3, 114.5, 119.2, 124.0, 124.1, 127.9, 136.9, 138.5, 141.5, 149.4, 151.5, 159.8, 166.9. EI-MS m/z 268 (100%, [M]$^+$), 253 (40%), 149 (25%), 121 (20%). EI-HRMS m/z calc'd for C$_{15}$H$_{12}$N$_2$OS 268.0670, found 268.0668.

4-(2-(pyridin-2-yl)thiazol-5-yl)phenol (11). Thiazole 10 (1 eq., 0.373 mmol, 100 mg) was added to a 10 mL round bottom flask equipped with a stir bar. The flask was sealed with a rubber septum, evacuated under high vacuum, and backfilled with argon. Via an argon-filled syringe, anhydrous dichloromethane (2 mL) was transferred to the flask to dissolve the starting material. The flask was then lowered into a dry ice/acetone bath at −78° C., and upon thermal equilibration (~20 minutes), boron tribromide (3 eq., 1.12 mmol, 1.12 mL of a 1 M solution in dichloromethane) was added drop-wise to the stirred solution. The mixture was allowed to stir at −78° C. for 5 minutes followed by 2.5 hours at room temperature. The mixture was diluted with ethyl acetate (10 mL), washed with diH$_2$O (10 mL), and the pH was adjusted to 7 to neutralize the excess BBr$_3$ using saturated NaHCO$_3$. The aqueous layer was then extracted with ethyl acetate 2× more (10 mL each), and the combined organic layers were dried over MgSO$_4$, filtered, and concentrated to an orange-yellow crude solid. The crude solid was then purified via column chromatography (silica gel) using 1:1 ethyl acetate:hexanes, followed by recrystallization from 1:1 toluene:cyclohexane to afford 11 as a yellow crystalline solid. Yield: 73 mg (0.287 mmol, 77%). $^1$H NMR (MeOD, 400 MHz) δ 6.86 (d, J=8.8, 2H), 7.41 (ddd, J=7.5, 4.9, 1.2 Hz, 1H), 7.53 (d, J=8.9, 2H), 7.90 (ddd, J=7.9, 7.6, 1.7 Hz, 1H), 8.00 (s, 1H), 8.13 (dt, J=8.0, 1.1 Hz, 1H), 8.56 (ddd, J=4.9, 1.7, 1.0 Hz, 1H). $^{13}$C NMR (MeOD, 100 MHz) δ 117.0, 120.3, 123.7, 125.7, 129.1, 138.6, 139.0, 143.7, 150.5, 152.4, 159.5, 167.7. EI-MS m/z 254 (100%, [M]$^+$), 150 (45%), 121 (20%). EI-HRMS m/z calc'd for C$_{14}$H$_{10}$N$_2$OS 254.0514, found 254.0513.

3-(4-(2-(pyridin-2-yl)thiazol-5-yl)phenoxy)propane-1-sulfonate sodium salt (2). To a 10 mL round bottom flask equipped with a stir bar was added phenol 11 (1 eq., 0.248 mmol, 63 mg) and 1,4-dioxane (2 mL). Under magnetic stirring, NaOH (75 µL of a 20% (w/v) aqueous solution) was added to the solution, precipitating the phenolate anion intermediate. The precipitate was redissolved by adding a few drops of water to the stirred mixture. After 15 minutes, 1,3-propanesultone (1 eq., 0.248 mmol, 30.3 mg) was added, and the solution was allowed to stir vigorously for 4 hours. The 1,4-dioxane/water mixture was removed by gentle evaporation, and the product was crystallized from a 3:1 isopropanol:methanol mixture to afford 2 as a yellow crystalline solid. Yield: 72 mg (0.181 mmol, 73%). $^1$H NMR (DMSO-d6, 400 MHz) δ 2.00-2.06 (m, 2H), 2.58 (t, J=7.4 Hz, 2H), 4.13 (t, J=6.6 Hz, 2H), 7.03 (d, J=8.8 Hz, 2H), 7.49 (ddd, J=7.5, 4.8, 1.2 Hz, 1H), 7.69 (d, J=8.8 Hz, 2H), 7.97 (td, J=7.7, 1.7 Hz, 1H), 8.13 (dt, J=7.9, 1.0 Hz, 1H), 8.27 (s, 1H), 8.64 (ddd, J=4.8, 1.6, 1.0 Hz, 1H). $^{13}$C NMR (DMSO-d6, 100 MHz) δ 25.2, 47.8, 66.9, 115.2, 118.8, 123.1, 124.9, 127.9, 137.7, 139.2, 140.9, 149.7, 150.6, 159.1, 166.0. ESI-HRMS m/z calc'd for C$_{17}$H$_{15}$N$_2$O$_4$S$_2$ ([M+H]$^+$) 375.0479, found 375.0476.

Scheme 3. Synthesis of ZN(II)-responsive fluorophore 3a and 3b.

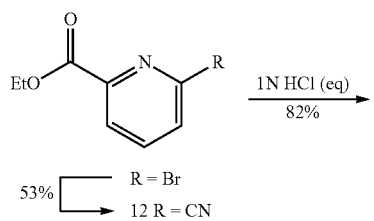

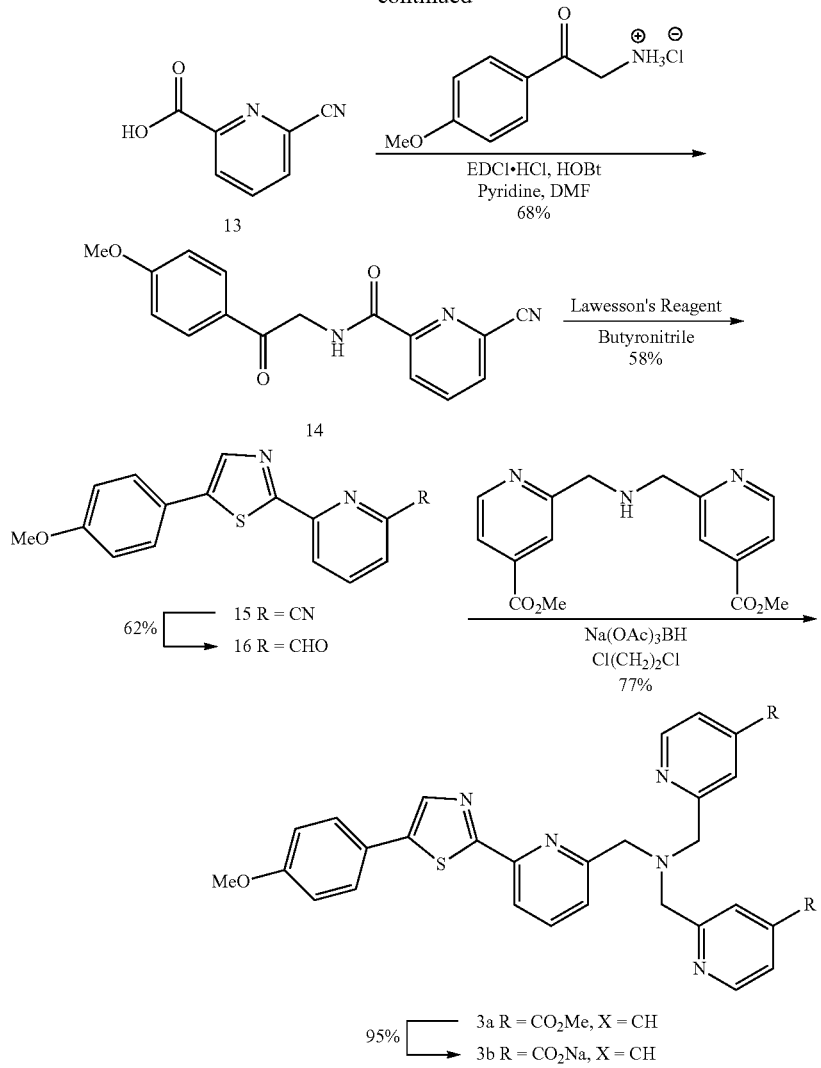

6-cyanopicolinic acid ethyl ester (12). Solid ethyl 6-bromopicolinate (1 eq., 65.2 mmol, 15.0 g) and cuprous cyanide (2 eq., 130.4 mmol, 11.68 g) were added to a 250-mL round bottomed flask equipped with a stir bar. To the round bottomed flask was added anhydrous pyridine (60 mL). Under rapid stirring, the mixture was refluxed under argon for 6 hours. The flask was removed from the hot oil bath, and the black tarry mixture that remained in the flask was diluted with hot toluene (100 mL). To the diluted mixture was added celite powder (~20 g), and the mixture was allowed to stir for ~20 minutes to allow the toluene to penetrate the tarry residue, then the celite/tar was filtered through a bed of celite and washed with hot toluene (50 mL). The filtrate was decanted into a 500-mL round bottom flask, and the solvents were removed under reduced pressure to yield a thick, black residue. The residue was redissolved in ethyl acetate (400 mL), and the solution was transferred to a separatory funnel, diluted with 1 M citric acid (300 mL), and the aqueous layer was extracted with ethyl acetate (2×200 mL). The combined organic layers were dried over MgSO$_4$ and filtered, and concentrated under reduced pressure to yield an orange solid, which was recrystallized from boiling hexanes to yield a white crystalline solid. The white solid was collected by suction filtration, washed with cold hexanes, and dried under high vacuum to give. Yield: 8.23 g (46.7 mmol, 72%). $^1$H NMR (CDCl$_3$, 400 MHz) δ 1.46 (t, J=7.1 Hz, 3H), 4.52 (q, J=7.1 Hz, 2H), 7.90 (dd, J=7.8, 1.1 Hz, 1H), 8.06 (t, J=7.9 Hz, 1H), 8.34 (dd, J=8.0, 1.1 Hz, 1H). $^{13}$C NMR (CDCl$_3$, 100 MHz) δ 14.2, 62.6, 116.3, 127.9, 131.1, 133.9, 138.4, 149.7, 163.5. ESI-MS m/z 177 ([M+H]$^+$, 46%), 149 (90%). ESI-HRMS m/z 177 calc'd for C$_9$H$_9$O$_2$N$_2$ ([M+H]$^+$) 177.0659, found 177.0656.

6-cyanopicolinic acid (13). To a 100-mL round bottom flask was added 40 mL of 1N HCl (aq). The flask was lowered into a 100° C. oil bath until the aqueous solution began to boil. While rapidly stirring, solid 6-cyanopicolinic acid ethyl ester (28.95 mmol, 5.10 g) was added to the boiling solution, and a vacuum adapter equipped with a glass frit was inserted into the top joint to limit the rate of water evaporation but allow for the removal of ethanol as the starting material was hydrolyzed. Because of the low melting point of the starting material, the reaction mixture was initially biphasic, but the biphasic mixture was slowly converted to a homogeneous solution as the starting material was consumed. The solution was stirred for one hour, and then the flask was removed from the oil bath and allowed to cool to room temperature under medium stirring to permit crystallization of the product. To complete crystallization, the mixture was stirred at 0° C. for another hour. The white precipitate was collected by suction filtration, washed with ice cold water (30 mL), followed by one portion (30 mL) of hot hexanes and one portion (30 mL) of 1:1 hexanes: dichloromethane. The white solid was then recrystallized from boiling toluene, collected by vacuum filtration, and washed with additional toluene. Yield: 3.50 g (23.63 mmol, 82%). $^1$H NMR (Acetone-d6, 400 MHz) δ 8.22 (dd, J=7.7, 1.2 Hz, 1H), 8.34 (t, J=7.8 Hz, 1H), 8.42 (dd, J=8.0, 1.2 Hz, 1H), 11.96 (s, br, 1H). $^{13}$C NMR (Acetone-d6, 100 MHz) δ 117.4, 128.7, 132.6, 133.9, 140.5, 150.2, 164.6. ESI-HRMS m/z 149 calc'd for $C_7H_5O_2N_2$ ([M+H]$^+$) 149.0346, found 149.0342.

6-cyano-N-(2-(4-methoxyphenyl)-2-oxyethyl)picolinamide (14). To a clean, dry 100-mL round bottom flask was added 6-cyanopicolinic acid 2 (1 eq., 19.93 mmol, 2.95 g), 2-amino-4'-methoxyacetophenone hydrochloride #[1] (1.1 eq., 21.92 mmol, 4.42 g), 1-ethyl-3-(3-dimethylaminopropyl) carbodiimide hydrochloride (EDCI.HCl, 1.5 eq., 29.9 mmol, 5.73 g), and 1-hydroxybenzotriazole (HOBt, 0.5 eq., 9.97 mmol, 1.35 g) with a stir bar. The starting materials and reagents were dissolved in N,N-dimethylformamide (DMF, 60 mL), and upon dissolution (~5 min), pyridine (1 eq., 19.93 mmol, 1.61 mL) was added drop-wise to the stirring solution, and the solution was allowed to stir for 6 hours. The solution was then decanted into a 250-mL round bottom flask, diluted with 100 mL of deionized water to precipitate the product. The product was then collected by suction filtration, washed with cold deionized water and allowed to dry under vacuum. Yield: 6.47 (21.91 mmol, 68%). $^1$H NMR (CDCl$_3$, 400 MHz) δ 3.90 (s, 3H), 4.93 (d, J=4.8 Hz, 2H), 7.00 (d, J=8.9 Hz, 2H), 7.87 (dd, J=7.7, 1.1 Hz, 1H), 8.02 (d, J=8.9 Hz, 2H), 8.06 (t, J=7.8 Hz, 1H), 8.44 (dd, J=8.0, 1.1 Hz, 1H), 8.75 (t, J=4.6 Hz, 1H). $^{13}$C NMR (CDCl$_3$, 100 MHz) δ 46.0, 55.6, 114.1, 116.5, 125.5, 127.3, 130.3, 130.6, 132.4, 138.7, 151.0, 162.5, 164.2, 191.6. EI-MS m/z 295 ([M]$^+$, 1%), 135 (100%). EI-HRMS m/z calc'd for $C_{16}H_{13}N_3O_3$ 295.0957, found 295.0954.

6-(5-(4-methoxyphenyl)thiazol-2-yl)picolinonitrile (15). To a round-bottomed flask containing vacuum-dried picolinamide 3 (1 eq., 14.97 mmol, 4.42 g) and Lawesson's Reagent (1.3 eq., 19.46 mmol, 7.87 g) was added to an oven-dried 100-mL round bottom flask equipped with a stir bar. The flask was connected to a reflux condenser, and the system was flushed with argon for several minutes to remove moisture. Through the top of the reflux condenser was added butyronitrile (60 mL) that had been previously dried over 0.4 Å molecular sieves and filtered. The apparatus was flushed further with argon and then capped with a glass frit. The flask was lowered into an oil bath at 130° C., and the mixture was refluxed for 30 minutes. The solution was then removed from the oil bath, allowed to cool to room temperature, and the butyronitrile was removed under reduced pressure to yield a dark orange solid residue. The residue was transferred to a 500-mL flask and dissolved in reagent-grade acetone (400 mL). In a 2-L round bottom flask was dissolved 23.7 g of potassium permanganate in acetone (600 mL). The crude residue solution was decanted into a 1-L flask, and the dark purple solution was allowed to stir vigorously for 10 minutes to convert the thioamide byproduct back to the desired nitrile. The reaction was quenched by the addition of 1 M citric acid (aq) (500 mL). The teal-colored solution was filtered through a pad of celite, and the filtrete was concentrated under reduced pressure. The resulting solution was neutralized with saturated aqueous NaHCO$_3$ and extracted with dichloromethane (3×300 mL). The combined organic layers were dried over MgSO$_4$, filtered, and concentrated under reduced pressure to yield a yellow solid. The solid was then redissolved in a minimal amount of dichloromethane, loaded onto a 5-cm bed of silica gel, and purified over silica gel using dichloromethane as the eluent. The column product was recrystallized from boiling n-dibutyl ether (purified by stirring with crushed KOH pellets to remove any potential peroxide contamination, followed by filtration through a glass frit), collecting the pure yellow crystals by suction filtration and washing with addition n-dibutyl ether. Yield: 2.55 g (8.68 mmol, 58%). $^1$H NMR (CDCl$_3$, 400 MHz) δ 3.87 (s, 3H), 6.98 (d, J=8.9 Hz, 2H), 7.59 (d, J=8.9 Hz, 2H), 7.69 (dd, J=7.6, 1.1 Hz, 1H), 7.93 (t, J=8.1 Hz, 1H), 8.00 (s, 1H), 8.38 (dd, J=8.1 Hz, 1.1 Hz, 1H). $^{13}$C NMR (CDCl$_3$, 100 MHz) δ 55.4, 114.7, 116.8, 122.5, 123.6, 128.2, 128.3, 133.4, 138.0, 138.9, 143.3, 153.2, 160.2, 164.2. EI-MS m/z 293 ([M]$^+$, 100%), 278 (30%), 250 (10%), 149 (15%), 121 (16%), 77 (12%). EI-HRMS m/z calc'd for $C_{16}H_{11}N_3OS$ 293.0623, found 293.0623.

6-(5-(4-methoxyphenyl)thiazol-2-yl)picolinaldehyde (16). Solid picolinonitrile 4 (1 eq., 8.37 mmol, 2.46 g) was added to a 250-mL round bottom flask equipped with a stir bar. Via a rubber septum, the flask was evacuated and backfilled with argon several times to ensure exclusion of moisture. Once the starting material was nearly completely dissolved in anhydrous THF (80 mL), a 0.5 M solution of lithium diisobutyl tert-butoxyaluminum hydride (LDBBA, 1.5 eq., 12.56 mmol, 25.12 mL), that was prepared according to a published literature procedure, was added dropwise to the rapidly stirred suspension. The deep blue solution that emerged after complete addition of the LDBBA reagent was stirred for 1 hour at room temperature. The reaction was quenched with the addition of 30 mL of 1 M citric acid and stirred for 20 minutes. The turbid mixture was extracted with EtOAc (3×50 mL), and the combined organic layers were dried over MgSO$_4$, filtered, and concentrated to afford a yellow-orange solid. The solid residue was purified by column chromatography (silica gel) using 1:1 EtOAc: hexanes as the eluent. The yellow column product was then recrystallized from boiling cyclohexane, and the pale yellow crystals were collected by suction filtration, washed with cold cyclohexane and dried over vacuum. Yield: 1.54 g (5.20 mmol, 62%). $^1$H NMR (CDCl$_3$, 400 MHz) δ 3.87 (s, 1H), 6.98 (d, J=8.9 Hz, 2H), 7.60 (d, J=8.9 Hz, 1H), 7.95-8.01 (m, 2H), 8.02 (s, 1H), 8.39 (dd, J=6.7, 2.3 Hz, 1H), 10.14 (s, 1H). $^{13}$C NMR (CDCl$_3$, 100 MHz) δ 55.4, 114.6, 121.6, 123.3, 123.8, 128.1, 138.0, 138.8, 142.5, 152.2, 152.4, 160.1, 165.4, 193.0. EI-MS m/z 296 ([M]$^+$100%), 281 (33%), 149 (27%), 121 (26%). EI-HRMS m/z calc'd for $C_{16}H_{12}N_2O_2S$ 296.0619, found 296.0624.

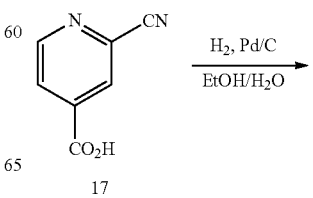

17

-continued

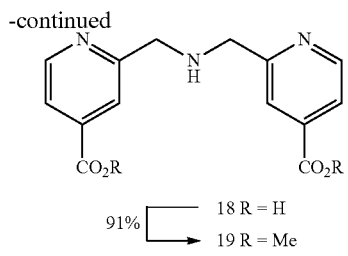

91% {
18 R = H
19 R = Me
}

2,2'-[iminobis(methylene)]diisonicotinic acid (18). 2-cyanoisonicotinic acid (21.7 mmol, 3.21 g) and 50% water wet 10% Palladium on activated carbon (1 mol %, 0.217 mmol, 461 mg) were stirred together in water (10 mL) in a 100 mL round-bottom flask. Methanol (20 mL) was added, followed by trimethylamine (1.2 eq., 26.0 mmol, 3.62 mL), and the flask was connected to a 3-way stopcock adapter, evacuated, and quickly back-filled with hydrogen gas from a 1-L gas burette. The burette was refilled to 1000 mL, and the mixture was vigorously stirred. After 250 mL of $H_2(g)$ had been consumed, a further 50 mL of hydrogen was added to the burette to provide the full theoretical amount required (1040 mL at 22° C. and 1 atm). $H_2(g)$ consumption proceeded steadily for approximately 3 hours, then abruptly stopped with 35 mL remaining in the burette, corresponding to consumption of 98% of the theoretical amount. The flask was purged with argon, the mixture was filtered through celite, and the filter cake was washed with ethanol. The combined filtrate was concentrated to a viscous residue, which was taken up in ethanol (100 mL), diluted with toluene (50 mL), and concentrated again. The resulting partially solidified material was taken up in ethanol, filtered through a glass frit to remove the precipitated primary amine byproduct, and concentrated to dryness. The residue from the filtration was taken up in water (25 mL) and the product was precipitated by addition of 90% formic acid, collected by filtration, washed with ice water, and dried by suction overnight. Yield: 1.44 mg (5.01 mmol, 44%). Note: to dissolve in MeOD, two drops of potassium deuteroxide (KOD, 40% w/v in $D_2O$) were added, the solution was blown dry under a stream of argon to remove the $D_2O$, and the compound was redissolved in MeOD. $^1$H NMR (MeOD, 400 MHz) δ 3.98 (s, 4H), 7.72 (dd, J=5.1, 1.4 Hz, 2H), 7.90 (s, 2H), 8.54 (d, J=5.5 Hz, 2H). $^{13}$C NMR (MeOD, 100 MHz) δ 54.9, 123.2, 123.5, 148.4, 150.0, 160.5, 172.7. ESI-HRMS m/z 288 calc'd for $C_{14}H_{14}O_4N_3$ ([M+H]$^+$) 288.0979, found 288.0980.

2,2'-[iminobis(methylene)]diisonicotinic acid dimethyl ester (19). To a 25 mL round bottom flask equipped with a magnetic stir bar was added the starting dicarboxylic acid 18 (1 eq., 2.78 mmol, 800 mg) and methanol (12 mL). While stirring under a gentle stream of argon, trimethylsilyl chloride (TMSCl, 3 eq., 8.35 mmol, 1.06 mL) was added drop-wise into the mixture at room temperature, followed by vigorous stirring under reflux overnight. The following day, the methanol was removed under reduced pressure, the residue was reconstituted in dichloromethane (25 mL), washed with saturated $NaHCO_3$ (25 mL), and the organic layer was dried over $MgSO_4$, filtered, and concentrated to an amber-colored oil. The pure oil was crystallized by the addition of cyclohexane and subsequently recrystallized from boiling cyclohexane to afford 5 as yellow solid. Note: the crystallization was relatively insufficient, so the remainder of the pure compound was kept as an oil. Yield: 800 mg (2.54 mmol, 91%). $^1$H NMR (CDCl$_3$, 400 MHz) δ 3.96 (s, 6H), 4.06 (s, 4H), 7.23 (dd, J=5.1, 1.6 Hz, 2H), 7.91 (s, 1H), 8.72 (d, J=5.1 Hz, 2H). $^{13}$C NMR (CDCl$_3$, 100 MHz) δ 52.5, 54.1, 121.1, 121.3, 137.6, 149.9, 160.4, 165.4. EI-MS m/z 165 (53%), 151 (100%), 137 (12%), 92 (10%). EI-HRMS m/z calc'd for $C_{16}H_{17}N_3O_4$ 315.1219, found 315.1208.

Fluorophore dimethyl ester (3a). To an oven-dried 10-mL round bottom flask equipped with a stir bar was added aldehyde 5 (1 eq., 0.506 mmol, 150 mg), bispicolylamine dimethyl ester (1.07 eq., 0.542 mmol, 171 mg), and Na(OAc)$_3$BH (1.5 eq., 0.759 mmol, 161 mg). Via a rubber septum, the flask was evacuated for several minutes and backfilled with argon to exclude moisture, and through an argon-filled needle was added 2 mL of anhydrous 1,2-dichloroethane to dissolve the reagents. The reaction was allowed to stir at room temperature for 24 hours. The reaction was quenched by the addition of 2 mL of di$H_2$O and allowed to stir for ~20 minutes. The organic layer was removed, dried over MgSO$_4$, filtered, and concentrated under reduced pressure to afford a yellow oily residue. The residue was purified by column chromatography (neutral alumina) using 9:1 dichloromethane:methanol to afford 6 as a glassy yellow solid. Yield: 232 mg (0.39 mmol, 77%). $^1$H NMR (CDCl$_3$, 400 MHz) δ 3.86 (s, 3H), 3.92 (s, 6H), 3.98 (s, 2H), 4.07 (s, 4H), 6.96 (d, J=8.8 Hz, 2H), 7.51 (d, J=7.7 Hz, 1H), 7.60 (d, J=8.7 Hz, 2H), 7.70 (dd, J=5.0, 1.5 Hz, 2H), 7.76 (t, J=7.8 Hz, 1H), 7.97 (s, 1H), 8.01 (d, J=7.7 Hz, 2H), 8.18 (s, 2H), 8.69 (d, J=5.0 Hz, 2H). $^{13}$C NMR (CDCl$_3$, 100 MHz) δ 52.6, 55.4, 59.7, 60.1, 114.5, 117.5, 121.2, 122.2, 123.7, 124.1, 128.0, 137.7, 137.8, 138.5, 141.5, 149.9, 150.8, 158.7, 159.8, 160.5, 165.7, 167.4. ESI-HRMS m/z calc'd for $C_{32}H_{30}O_5N_5S$ ([M+H]$^+$) 596.1956, found 596.1962.

Fluorophore dicarboxylate (3b). Fluorophore dimethyl ester 6a (1 eq., 0.167 mmol, 100 mg) was added to a 10 mL round bottom flask and dissolved in methanol (3 mL). While stirring, NaOH (2.8 eq., 0.468 mmol, 62 μL of a 30% (w/v) solution in $H_2O$) was pipetted into the solution, and the mixture was refluxed for 1 hour. The solution was cooled to room temperature, and the methanol was removed under a gentle stream of argon. Absolute ethanol (6 mL) was added to the flask, the mixture was heated until concentrated enough to allow for crystallization of the product. The crystals were collected by vacuum filtration, washed with ethanol, and dried over vacuum to afford dicarboxylate 6b as a yellow solid. Yield: 97.3 mg (0.159 mmol, 95%). $^1$H NMR (MeOD, 400 MHz) δ 3.83 (s, 3H), 3.92 (s, 2H), 3.99 (s, 4H), 7.00 (d, J=8.9 Hz, 2H), 7.56 (dd, J=7.7, 0.9 Hz, 1H), 7.63 (d, J=8.9 Hz, 2H), 7.68 (dd, J=5.1, 1.5 Hz, 2H), 7.82 (t, J=7.7 Hz, 1H), 7.90 (dd, J=7.8, 0.9 Hz, 1H), 8.01 (s, 2H), 8.05 (s, 1H), 8.53 (dd, J=5.1, 0.7 Hz, 2H). $^{13}$C NMR (MeOD, 100 MHz) δ 55.9, 60.3, 61.7, 115.8, 118.9, 123.2, 124.5, 125.0, 125.5, 129.1, 139.1, 139.4, 143.1, 148.6, 150.0, 151.6, 160.1, 160.6, 161.7, 168.5, 172.7. ESI-HRMS m/z calc'd for $C_{30}H_{24}N_5O_5S$ ([M+H]$^+$) 566.1504, found 566.1506.

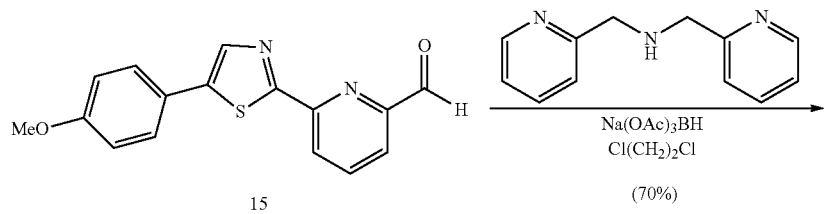

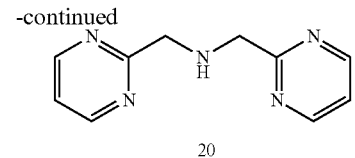

Fluorophore 3c. A 10-mL round-bottom flask containing aldehyde 15 (1 eq., 0.675 mmol, 200 mg) and a stir bar was charged with Na(OAc)₃BH (1.5 eq., 1.01 mmol, 215 mg) and bispicolylamine (1.2 eq., 0.81 mmol, 161 mg). After sealing with a rubber septum, the flask was evacuated under high vacuum and backfilled with argon. The contents of the flask were dissolved in anhydrous 1,2-dichloroethane (2 mL), and the reaction mixture was vigorously stirred overnight at room temperature. The following day, the reaction mixture was quenched with 1 M citric acid (1 mL) for ~10 minutes, the aqueous phase as made basic by the addition of saturated NaHCO₃(aq), and the product was extracted with dichloromethane (2×10 mL). The combined organic layers were dried over Na₂SO₄, filtered, and concentrated to a light brown solid residue. The product was dissolved in dichloromethane and purified by column chromatography (silica gel) using 3:10 acetone:DCM as the eluent, affording an pure oil which was crystallized and subsequently recrystallized from MTBE to yield off-white, fibrous crystals. Yield: 226 mg (0.471 mmol, 70%). $^1$H NMR (CDCl₃, 400 MHz) δ 3.84 (s, 3H), 3.93 (s, 2H), 3.95 (s, 4H), 6.95 (d, J=8.8 Hz, 2H), 7.12-7.16 (m, 2H), 7.53 (d, J=7.6 Hz, 1H), 7.57 (d, J=8.9 Hz, 2H), 7.64-7.68 (m, 4H), 7.40 (t, J=7.8 Hz, 1H), 7.95 (s, 1H), 8.00 (d, J=7.8 Hz, 1H), 8.54 (d, J=4.8 Hz, 2H). $^{13}$C NMR (CDCl₃, 100 MHz) δ 55.4, 59.5, 60.2, 114.5, 117.4, 122.0, 122.9, 123.4, 124.2, 128.0, 136.4, 137.3, 138.5, 141.4, 149.1, 150.8, 159.3, 159.4, 159.8, 167.4. ESI-HRMS m/z calc'd for $C_{28}H_{26}N_5OS$ ([M+H]⁺) 480.1844, found 480.1853.

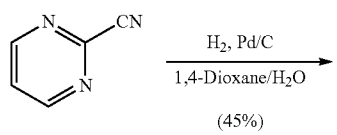

Bis(2-pyrimidylmethyl)amine (20). In a 250 mL round-bottom flask, 2-cyanopyrimidine (1 eq., 57.1 mmol, 6.00 g) was dissolved in a 1,4-dioxane:diH₂O (3:1) mixture, and to the solution was added palladium (10%) on activated carbon (50% wet by H₂O, 2 mol %, 2.43 g). The flask was equipped with a 3-way stopcock adapter connected to an H₂ burette, which was filled with 1000 mL of H₂ (g). After repeated evacuation and back-filling with H₂ from the gas burette, the mixture was rapidly stirred while H₂ (2 eq., 114.2 mmol, 2.762 L) consumption from the gas burette proceeded steadily over the course of 48 hours. After complete consumption of the 2.8 L of H₂, the hydrogen-filled flask was carefully purged with argon, the palladium was filtered through a celite filter cake, washed with additional 1,4-dioxane, and the 1,4-dioxane/H₂O was removed under reduced pressure to leave an amber-colored oil residue. The residue was purified by column chromatography (silica gel, 1:4 EtOH:DCM) to afford 20 as an amber-colored oil. Yield: 2.58 g (12.83 mmol, 45%). Note: For $^1$H/$^{13}$C NMR characterization, the oxalate salt of 20 was crystallized from MeOH/EtOH by the addition of 2.0 eq. of oxalic acid, followed by subsequent recrystallization from the boiling mixture. The product was filtered, dried under argon, and then redissolved in D₂O for NMR characterization. $^1$H (D₂O, 400 MHz) δ 3.98 (s, 4H), 7.72 (dd, J=5.1, 1.5 Hz, 2H), 7.90 (s, 2H), 8.54 (dd, J=5.1, 0.7 Hz, 2H). $^{13}$C NMR (D₂O, 100 MHz) δ 54.9, 123.2, 123.5, 148.4, 150.0, 160.5, 172.7. EI-MS m/z 201 (10%, [M]⁺), 122 (23%), 108 (100%), 94 (98%). EI-HRMS m/z calc'd for $C_{10}H_{11}N_5$ 201.1014, found 201.1004.

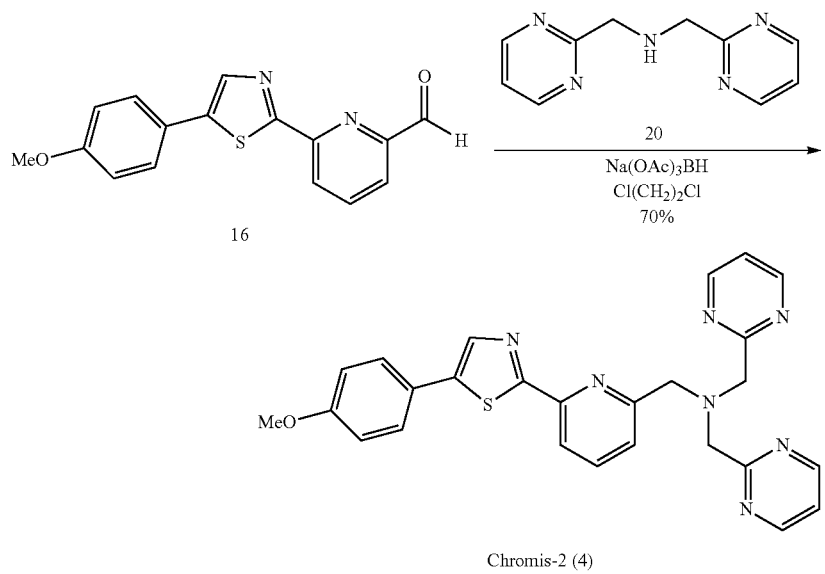

Chromis-2 (4)

Chromis-2 (4). To a 10-mL round-bottom flask containing bis(2-pyrimidylmethyl)amine (20, 1.2 eq., 0.956 mmol, 193 mg) was added aldehyde 16 (1 eq., 0.797 mmol, 236 mg), Na(OAc)$_3$BH (1.5 eq., 1.20 mmol, 253 mg) and a stir bar. The flask was sealed with a rubber septum, evacuated under high vacuum, and backfilled with argon. The contents were dissolved in anhydrous 1,2-dichloroethane (5 mL), and the reaction was stirred vigorously at room temperature for 24 hours. The reaction mixture was quenched with 1 M disodium citrate (2 mL), followed by extraction with dichloromethane (2×10 mL). The combined organic layers were dried over Na2SO4, filtered, and concentrated to an amber color oil residue, which was purified by column chromatography (silica gel) using 1:1 acetone:DCM as the eluent. The pure column product (pale yellow oil) was crystallized by the addition of MTBE, followed by recrystallization from boiling MTBE:cyclohexane to afford 4 as an off-white solid. Yield: 270 mg (0.561 mmol, 70%). $^1$H NMR (CDCl$_3$, 400 MHz) δ 3.85 (s, 3H), 4.26 (s, 2H), 4.35 (s, 4H), 6.95 (d, J=8.8 Hz, 2H), 7.16 (t, J=4.9 Hz, 2H), 7.56 (d, J=8.7 Hz, 2H), 7.71-7.76 (m, 2H), 7.94 (s, 1H), 7.97 (dd, J=5.9, 3.0 Hz, 1H), 8.72 (d, J=4.9 Hz, 4H). $^{13}$C NMR (CDCl$_3$, 100 MHz) δ 55.4, 59.9, 60.4, 114.5, 117.2, 119.1, 123.8, 124.2, 128.0, 137.2, 138.4, 141.2, 150.5, 157.0, 159.6, 159.8, 167.6, 168.5. EI-MS m/z 481 ([M]$^+$, 6%), 388 (40%), 282 (100%), 200 (73%). EI-HRMS m/z calc'd for C$_{26}$H$_{23}$N$_7$OS 481.1685, found 481.1699.

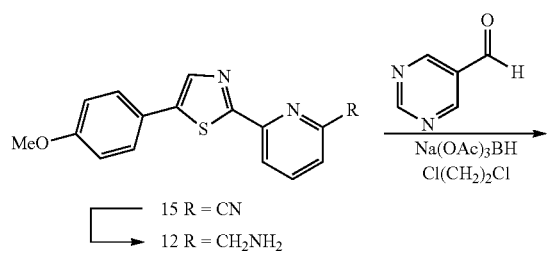

15 R = CN
12 R = CH$_2$NH$_2$

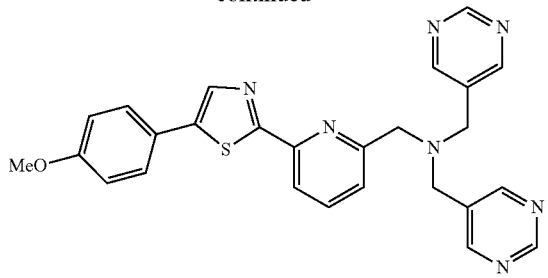

Chromis-2-ctrl (4a)

Primary amine 21. A 25-mL round-bottom flask containing nitrile 15 (1 eq., 1.1 mmol, 327 mg) and a magnetic stir bar was sealed with a rubber septum and evacuated under high vacuum to remove any residual moisture. After backfilling with argon, anhydrous THF (10 mL) was added to the flask through an argon-flushed syringe and needle. The flask was lowered into an ice bath and left to thermally equilibrate to 0° C., after which DIBAL-H (2.1 eq., 2.12 mmol, 1.77 mL of a 1.2 M solution in toluene) was added dropwise into the rapidly stirred mixture. After complete addition, the resulting dark amber-colored solution was stirred for 3 hours at 0° C. until TLC analysis (9:1 CH$_2$Cl$_2$:MeOH) confirmed the complete consumption of the starting nitrile. The reaction was quenched by the addition of 1M citric acid, and after stirring for 20 minutes, the citric acid was neutralized by the addition of saturated Na$_2$CO$_3$ (aq) until the pH was above 8. The mixture was diluted with diH$_2$O and extracted with DCM (3×50 mL), and the combined organic layers were dried over Na2SO4, filtered, and concentrated to an amber-colored solid. The crude product was used in the next synthetic step without further purification. Yield: 284 mg (0.834 mmol). ESI-HRMS m/z calc'd for C$_{28}$H$_{26}$N$_5$OS ([M+H]$^+$) 480.1844, found 480.1853.

Chromis-2-ctrl (4a). To a 10-mL round-bottom flask containing crude amine 21 (1 eq., 0.834 mmol, 248 mg) was added 5-formylpyrimidine (2.1 eq., 1.75 mmol, 189 mg), Na(OAc)$_3$BH (2.5 eq., 2.09 mmol, 442 mg) and a stir bar. The flask was sealed with a rubber septum, evacuated under high vacuum, and backfilled with argon. The contents were suspended in anhydrous 1,2-dichloroethane (5 mL), and the reaction was stirred vigorously at room temperature overnight. The reaction mixture was quenched with 1 M disodium citrate (1 mL) for ~15 minutes, followed by extraction with dichloromethane (3×10 mL). The combined organic layers were dried over $Na_2SO_4$, filtered, and concentrated to an amber-colored oil. The oily residue was purified by column chromatography (silica gel) using 7:3 acetone:DCM as the eluent. The pure column product (pale yellow oil) was crystallized by the addition of MTBE, followed by recrystallization from boiling MTBE:cyclohexane to afford 4a as an off-white solid. Yield: 54 mg (0.112 mmol, 13%). $^1H$ NMR ($CDCl_3$, 400 MHz) δ 3.82 (s, 4H), 3.84 (s, 2H), 3.86 (s, 3H), 6.97 (d, J=8.8 Hz, 2H), 7.30 (dd, J=7.7, 0.8 Hz, 1H), 7.60 (d, J=8.8 Hz, 2H), 7.79 (t, J=7.8 Hz, 1H), 7.99 (s, 1H), 8.09 (dd, J=7.8, 0.8 Hz, 1H), 8.82 (s, 4H), 9.17 (s, 2H). $^{13}C$ NMR ($CDCl_3$, 100 MHz) δ 53.1, 55.4, 58.1, 114.6, 118.1, 123.5, 124.0, 128.1, 131.7, 137.7, 138.7, 141.8, 151.3, 157.6, 158.1, 160.0, 166.8. EI-MS m/z 481 ([M]$^+$, 3%), 282 (100%). EI-HRMS m/z calc'd for $C_{26}H_{23}N_7OS$ 481.1685, found 481.1676.

Example 3. Determination of Protonation Constants

A. Glass Electrode Calibration.

Protonation constants were determined as concentration constants (log $K_H$) based on potentiometric titrations using a combination double junction glass electrode. The glass electrode was calibrated at 25° C. under argon by titration of a strong acid (5 mM HCl, prepared by dilution of a 0.1 M standardized solution, Sigma-Aldrich) with a strong base (0.1 M KOH, standardized solution, Sigma-Aldrich) in the presence of 0.1 M KCl as an ionic background using a water-jacketed, temperature-controlled titration vessel (Metrohm). From the experimental emf data, the endpoint, electrode potential, and slope were determined using Gran's Method as implemented in the GLEE software package ($pK_w$=13.78, μ=0.1 M KCl).[1] The calibration procedure was performed prior to each potentiometric titration, and the experimental electrode potential and slope that were used to calculate the experimental p[H] were derived as the average of the emf data from three independent titrations. Calibrations of the glass electrode were conducted on the same day as the determination of protonation constants.

B. Determination of the Protonation Constant of Compound 1.

Figure 12:
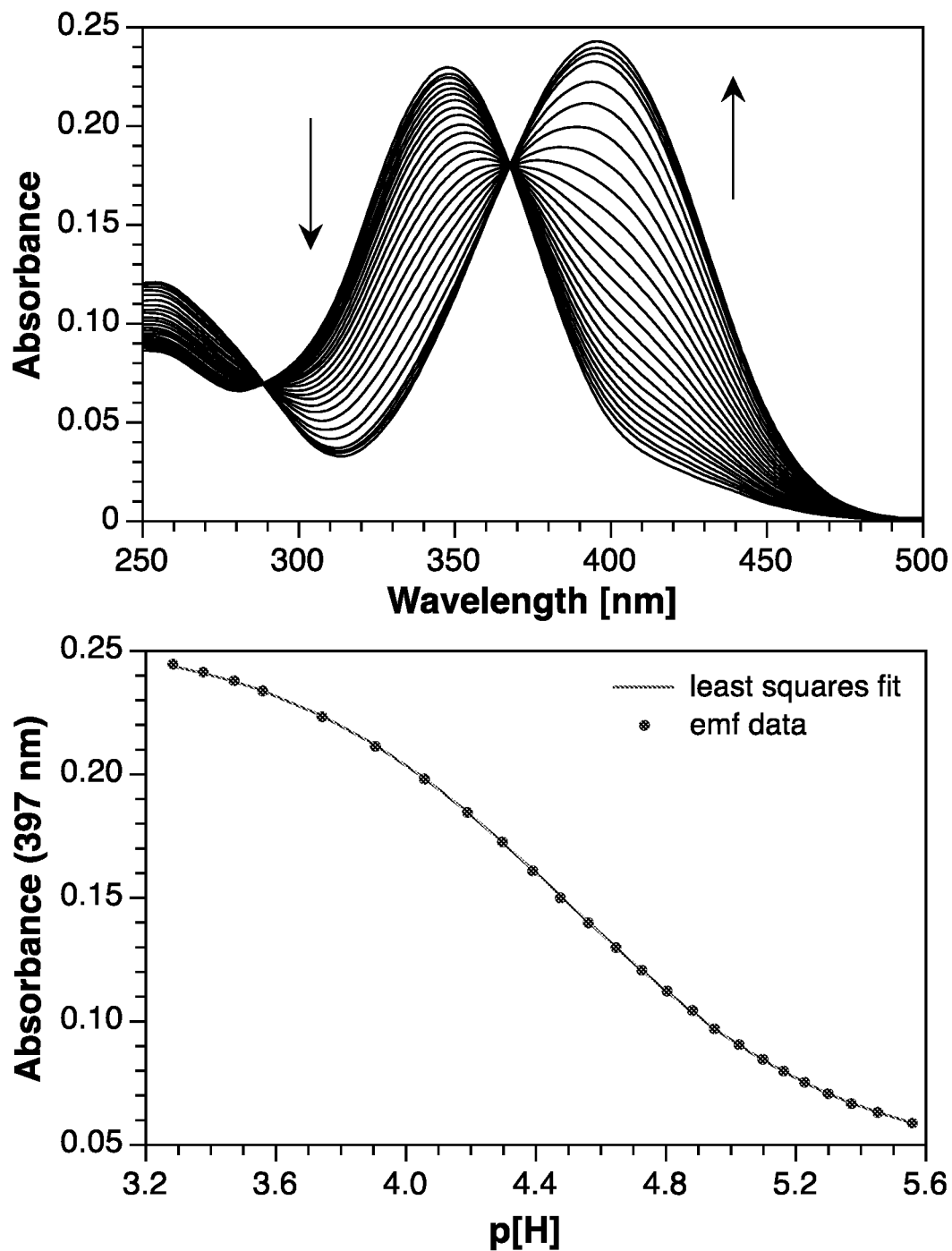
FIG. 12. Spectrophotometric pH titration of compound 1 at 25° C. in aqueous buffer (5 mM PIPBS, 0.1 M KCl, 5 mM KOH, pH 5.6). Black arrows indicate the change in absorbance after each aliquot of HCl was added. The absorbance from 250-500 nm was recorded as a function of $pH_e$ ($-\log[H_3O^+]$), and the data were analyzed by non-linear least squares fitting to a single protonation to yield an average $pK_{H1}$=4.49±0.002 (n=3).

A 10 μM solution of compound 1 (diluted from a 3 mM stock solution in $diH_2O$) was prepared in 3.0 mL of aqueous buffer (5 mM PIPBS, 0.1 M KCl, 5 mM KOH, 25° C., pH 5.6) in a quartz cuvette with a 1-cm pathlength. A combined potentiometric and spectrophotometric titration was carried out the cuvette by the addition of HCl using various aliquot sizes and concentrations to adjust the pH between 5.6 and 3.8 (thermostat accessory set to 25° C.). After the addition of each aliquot of acid, the solution was equilibrated via magnetic stirring until the pH electrode stabilized, the potential was recorded (in mV), and an absorbance spectrum was acquired over the spectral window of 250-500 nm. After correcting for dilution, the absorbance data were analyzed by non-linear least-squares fitting to a single protonation (FIG. 12).

C. Determination of the Protonation Constant of Compound 2.

Figure 13:
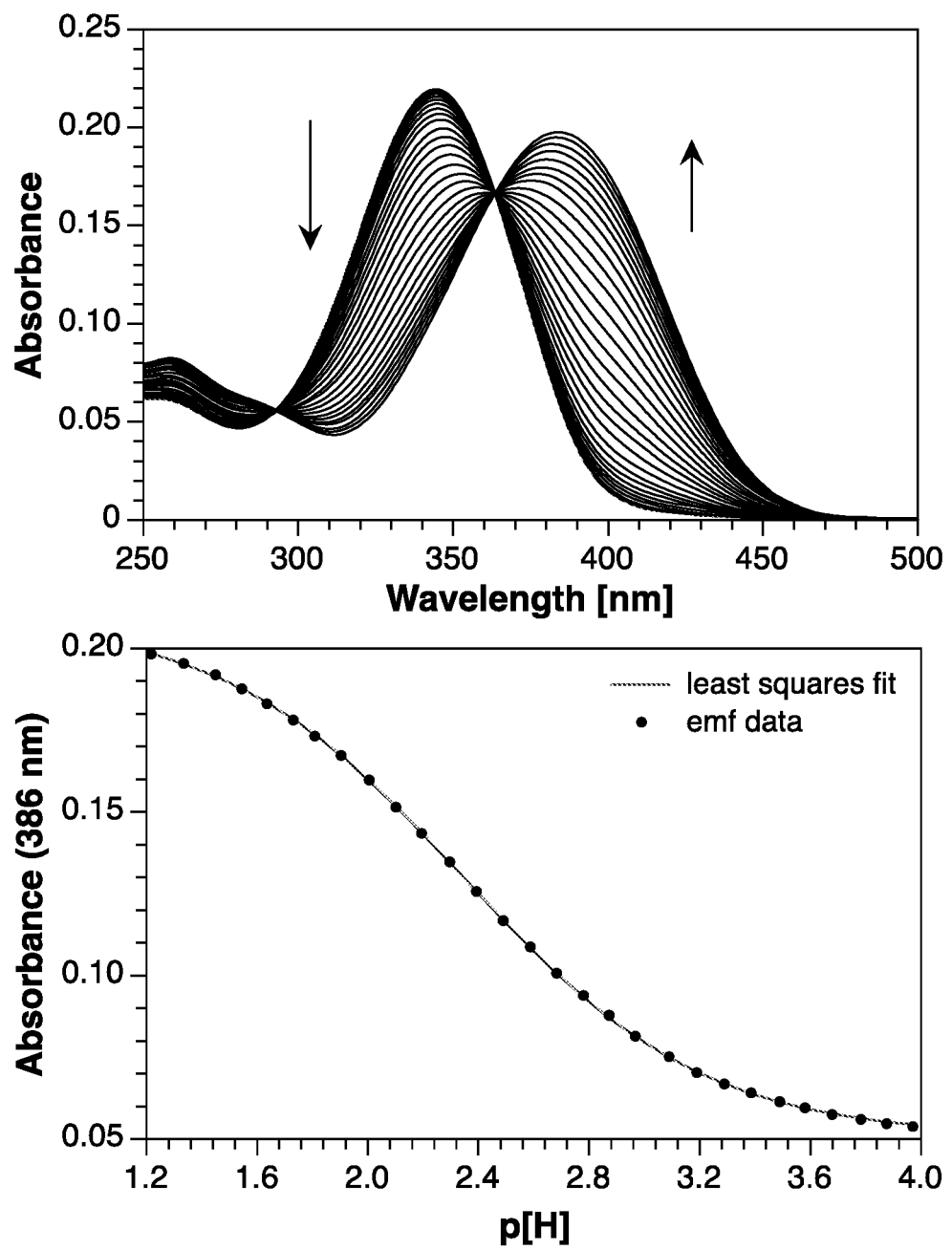
FIG. 13. Spectrophotometric pH titration of compound 2 at 25° C. in 0.1 M KCl. Black arrows indicate the change in absorbance after each aliquot of HCl was added. The absorbance (250-500 nm) was recorded as a function of $pH_c$ ($-\log[H_3O^+]$), and the data were analyzed by non-linear least squares fitting to a single protonation to yield an average $pK_{H1}$=2.34±0.002 (n=3).

A 10 μM solution of compound 2 (diluted from a 3 mM stock solution in $diH_2O$) was prepared in 3.0 mL of aqueous 0.1 M KCl (filtered through a 0.2 μm filter) in a quartz cuvette with a 1-cm pathlength, and the pH was adjusted to 4.0 using aqueous HCl (0.05 M, diluted from a standardized 0.1 M solution, Sigma-Aldrich). A combined potentiometric and spectrophotometric titration was carried out in the cuvette by the addition of HCl using various aliquot sizes and concentrations to adjust the pH between 4.0 and 1.2 (thermostat accessory set to 25° C.). After addition of each aliquot acid, the solution was equilibrated via magnetic stirring until the pH electrode stabilized, the potential was recorded (in mV), and an absorbance spectrum was acquired over the spectral window of 250-500 nm. After correcting for dilution, the absorbance data were analyzed by non-linear least-squares fitting to a single protonation (FIG. 13).

Example 4. Steady-State Absorption and Fluorescence Spectroscopy

General Spectroscopic Methods. All buffers and stock solutions used for spectroscopic measurements were prepared using either HPLC-grade water (JT Baker) or 18.2 MΩ.cm Mili-Q water and filtered through a 0.2 μm filter to remove interfering dust particles or fibers. UV-Vis measurements were performed on a Varian Cary Bio50 spectrophotometer with a constant temperature accessory (Peltier) at 25° C. Fluorescence measurements were performed with a PTI fluorimeter equipped with a 75 W xenon arc lamp excitation source and a photomultiplier detection system (PMT voltage was 1100 V for all experiments). Fluorescence spectra were corrected for the spectral response of the detection system and for the spectral irradiance of the excitation source (via a calibrated photodiode). For all experiments, both UV-Vis and fluorescence, a 1-cm path length quartz cuvette was used, except for quantum yield determinations, which were performed with a 10-cm path length quartz cuvette for absorbance measurements.

Determination of Fluorescence Quantum Yields. Fluorescence quantum yields of 1, 2, 3b and chromis-2 (4) were determined in aqueous buffer (10 mM PIPES, 0.1 M KCl) at pH 7.0 by a 4-point measurement over an OD range of 0.1-0.4 using a 10-cm cuvette, with fluorimeter excitation at 365 nm. For probes 3b and chromis-2, the solutions containing the free forms were supplemented with 20 μM EDTA (from a 30 mM stock solution in $diH_2O$) to sequester adventitious Zn(II), whereas to determine the Zn(II)-bound forms, the solutions were supplemented with 20 μM $ZnSO_4.7H_2O$ to ensure complete saturation of the fluorophore. Fluorescence quantum yields for all fluorophores were determined using quinine sulfate (Df=0.546 in 1.0 N $H_2SO_4$) as a fluorescence standard.[2] To determine the quantum yield of 3a, single-point measurements were performed in aqueous buffer (10 mM PIPES, 0.1 M KCl, pH 7.0) supplemented with 100 μM 4:1 DMPC:DMPG liposomes and at a probe concentration of 2 μM. The quantum yields were also referenced to quinine sulfate with an OD matching that of 3a (2 μM) in liposomes.

TABLE 6

Photophysical and spectral properties of compounds 1 and 2.

| | Neutral[a] | | Protonated[b] | |
| --- | --- | --- | --- | --- |
| | 1 | 2 | 1 | 2 |
| Abs $\lambda_{max}$ (nm)[b] | 346 | 345 | 397 | 386 |
| ε($10^4$ $M^{-1}cm^{-1}$)[c] | 1.80 | 2.25 | 1.96 | 2.05 |
| Em $\lambda_{max}$ (nm)[f] | 489 | 467 | 582 | 565 |
| $\Phi_F$[g] | 0.65 | 0.80 | n.d. | n.d. |

TABLE 6-continued

Photophysical and spectral properties of compounds 1 and 2.

| | Neutral[a] | | Protonated[b] | |
|---|---|---|---|---|
| | 1 | 2 | 1 | 2 |
| $pK_a$ | — | — | 4.49 | 2.34 |
| $pK_a^*$ | — | — | 11.7 | 9.5 |

[a]10 mM PIPES, 100 mM KCl, pH 7.0;
[b]0.1N HCl (pH 1.0);

Fluorescence Deuterium-Isotope Studies of Compounds 1 & 2. Comparison of the fluorescence intensities of compounds 1 and 2 were conducted in deuterated and non-deuterated buffer (10 mM PIPES, 100 mM KCl, pH/D 7.0, 25° C.). A 3.0-mL solution of aqueous buffer was supplemented with 10 µM of each compound (from 3 mM stock solutions in H$_2$O), and after thorough mixing via magnetic stirring, fluorescence spectra of 1 were acquired over the spectral window of 380-700 nm with excitation at x nm and analogous fluorescence spectra of 2 were acquired over the spectral window of 380-650 nm with excitation at x nm.

Figure 14A:
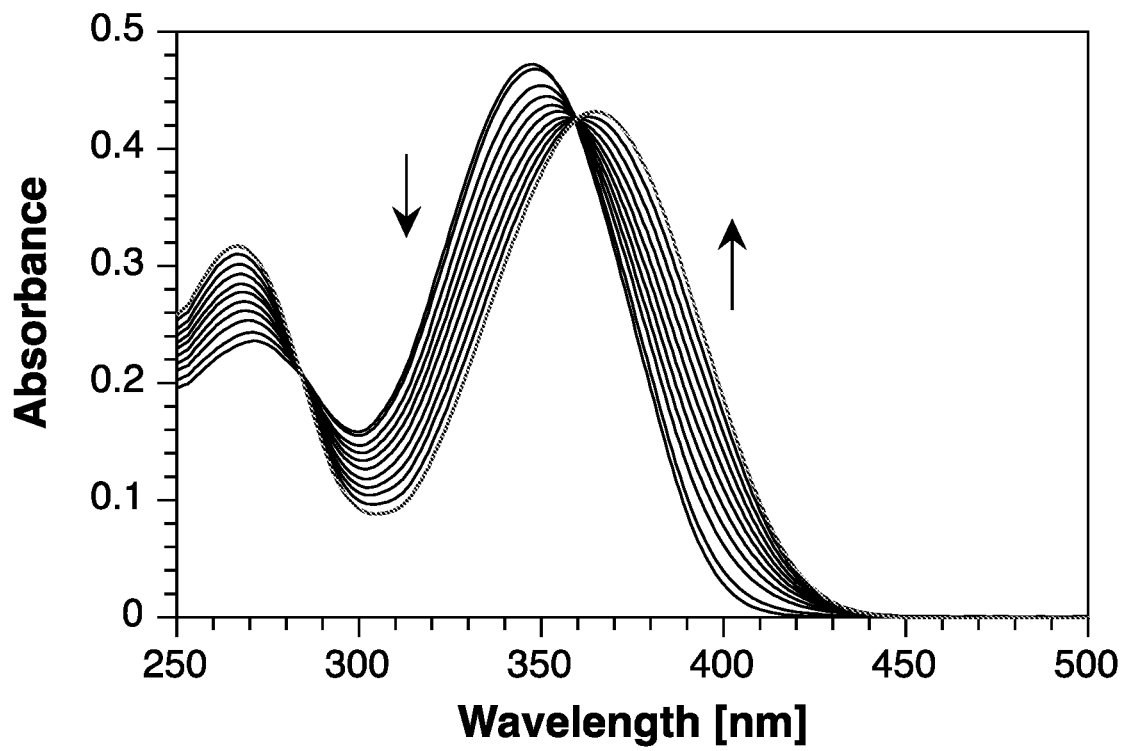
FIG. 14A-14B. Absorption (FIG. 14A) and emission (FIG. 14B) spectra of compound 3b via molar ratio titrations at pH 7.0 buffer (10 mM PIPES, 100 mM KCl, 25° C.).
Figure 14B:
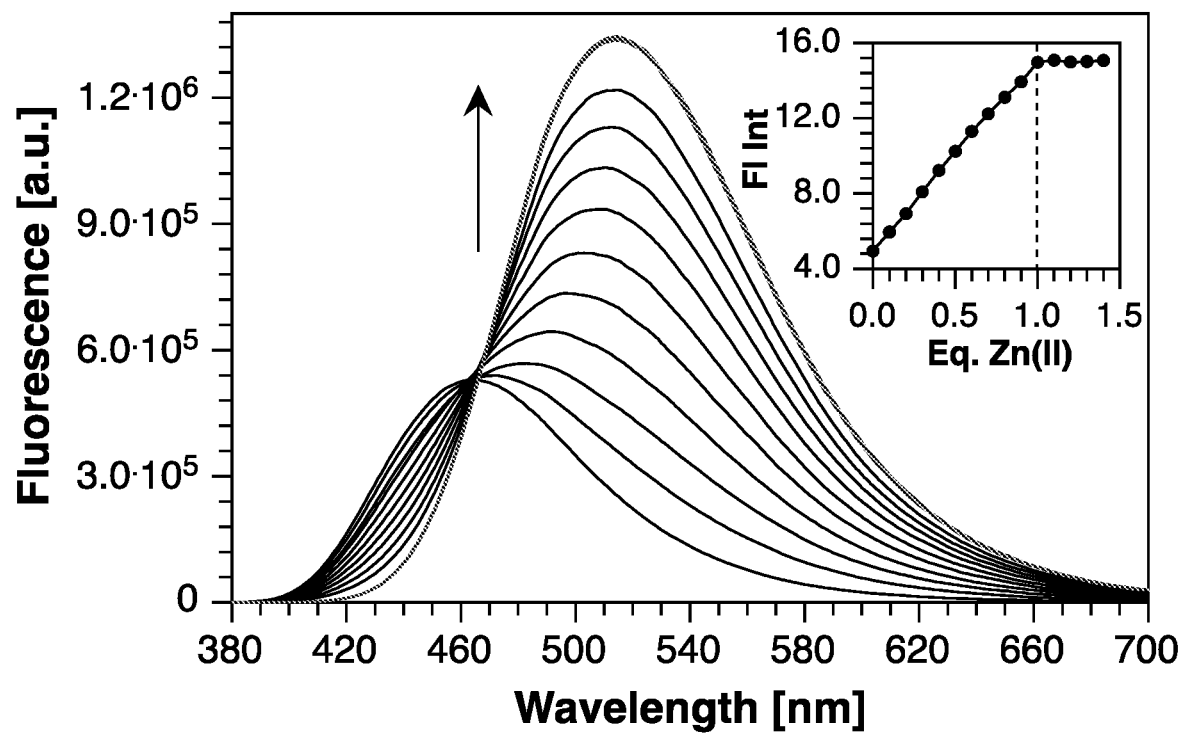

Molar Ratio Titration of Probe 3b with Zn(II). A 20 µM solution of 3b in pH 7.0 buffer (3.0 mL, 10 mM PIPES, 0.1 M KCl, 25° C.) prepared in a quartz cuvette with a 1-cm pathlength was titrated with ZnSO$_4$.7H$_2$O (from a 3 mM aqueous stock solution) in 2 µM (0.1 eq.) increments. After each aliquot, the solution was equilibrated for 30 seconds by magnetic stirring, and an absorbance (spectral window: 250-500 nm) (FIG. 14A) and fluorescence spectrum (excitation: 361 nm, spectral window: 380-700 nm) (FIG. 14B) were acquired.

Figure 15:
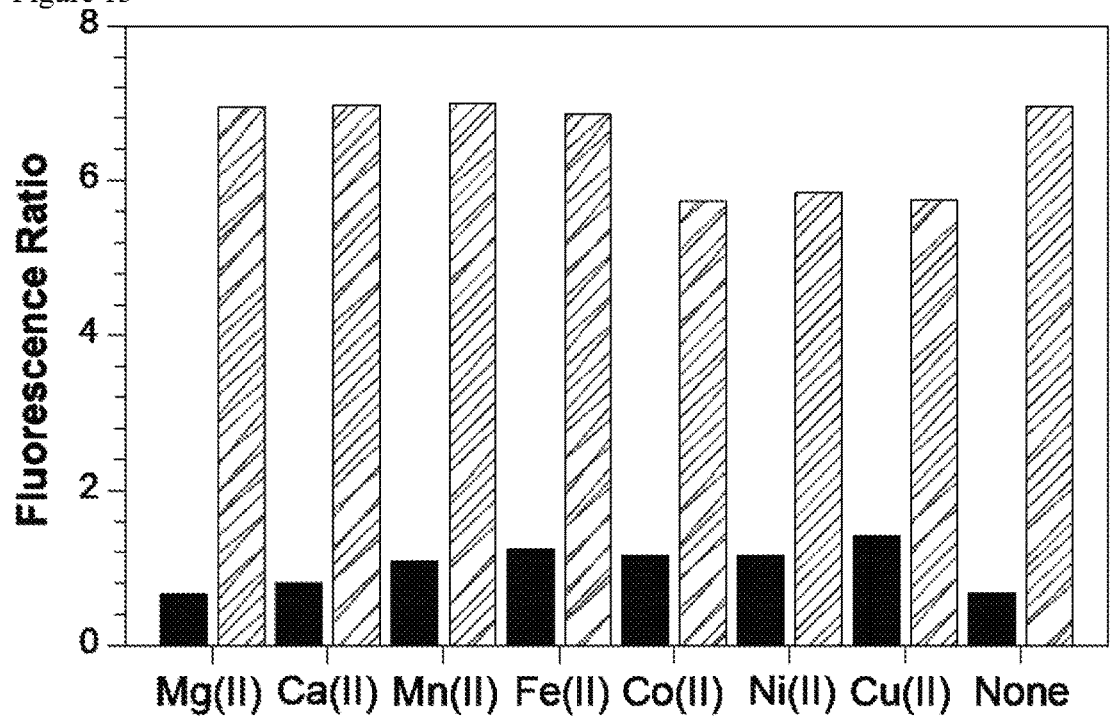
FIG. 15. Emission response of compound 3b towards interfering divalent metal ions.
Figure 16A:
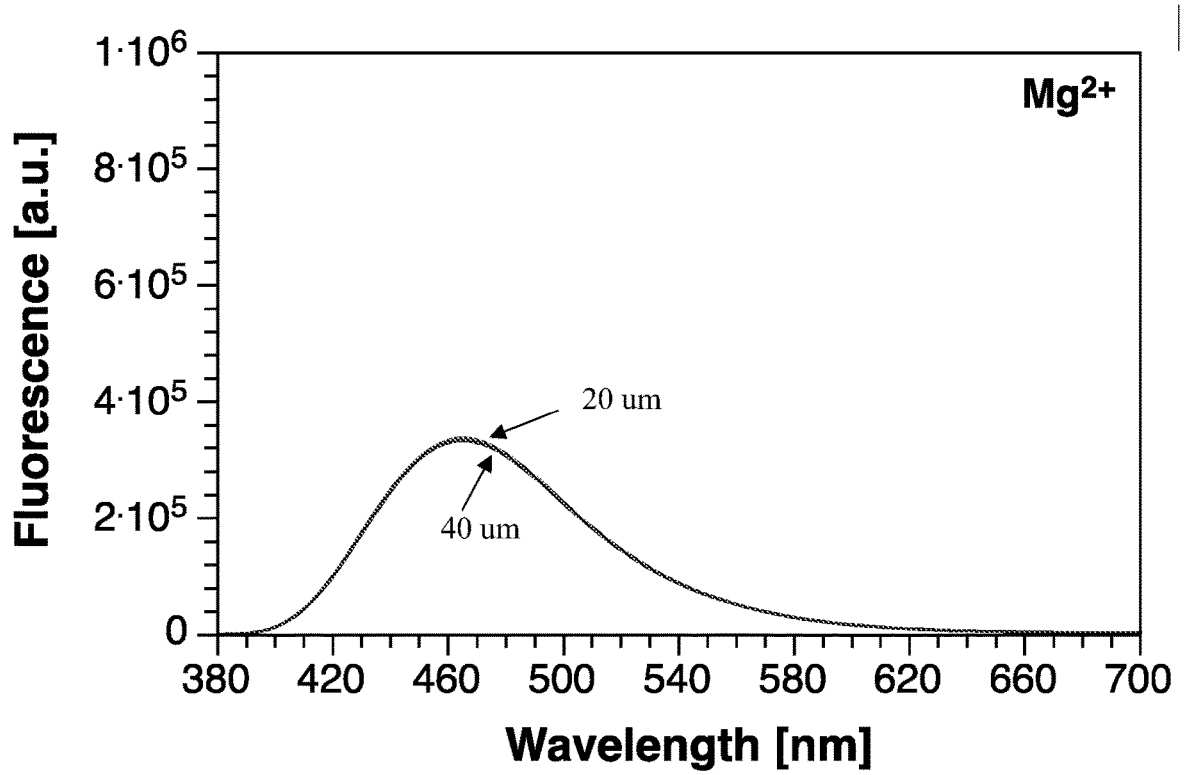
FIG. 16A-16H. Fluorescence response of compound 3b in the presence of 4.0 equivalents of interfering divalent metal ions.
Figure 16B:
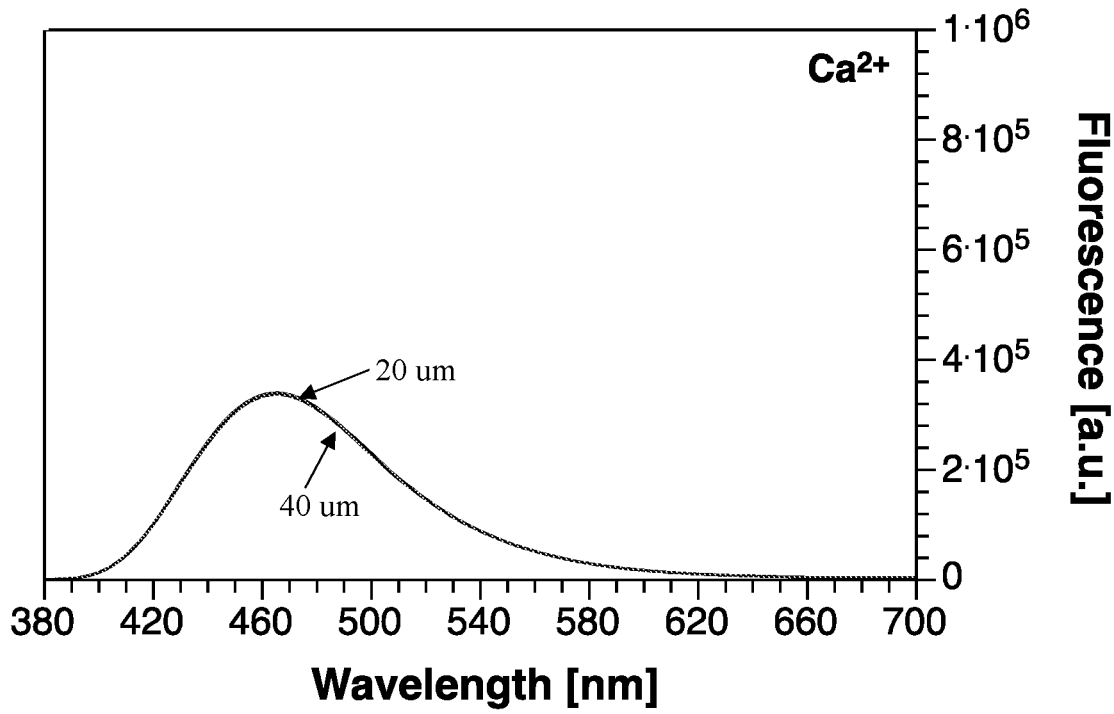
Figure 16C:
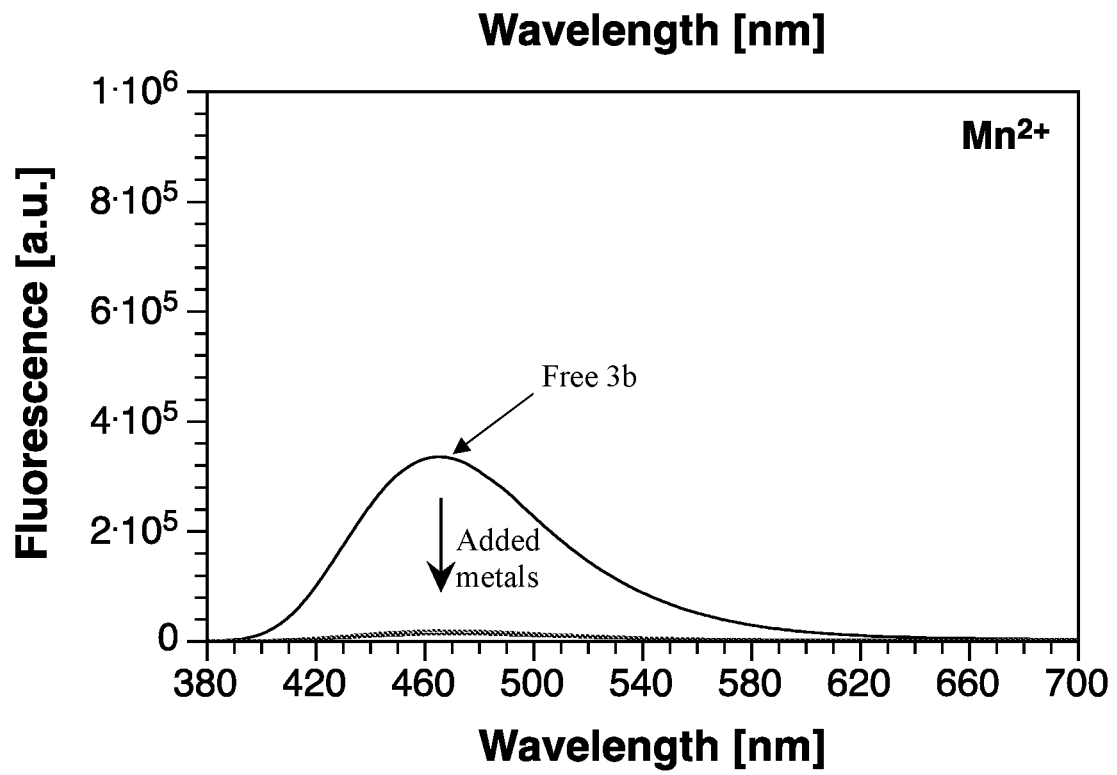
Figure 16D:
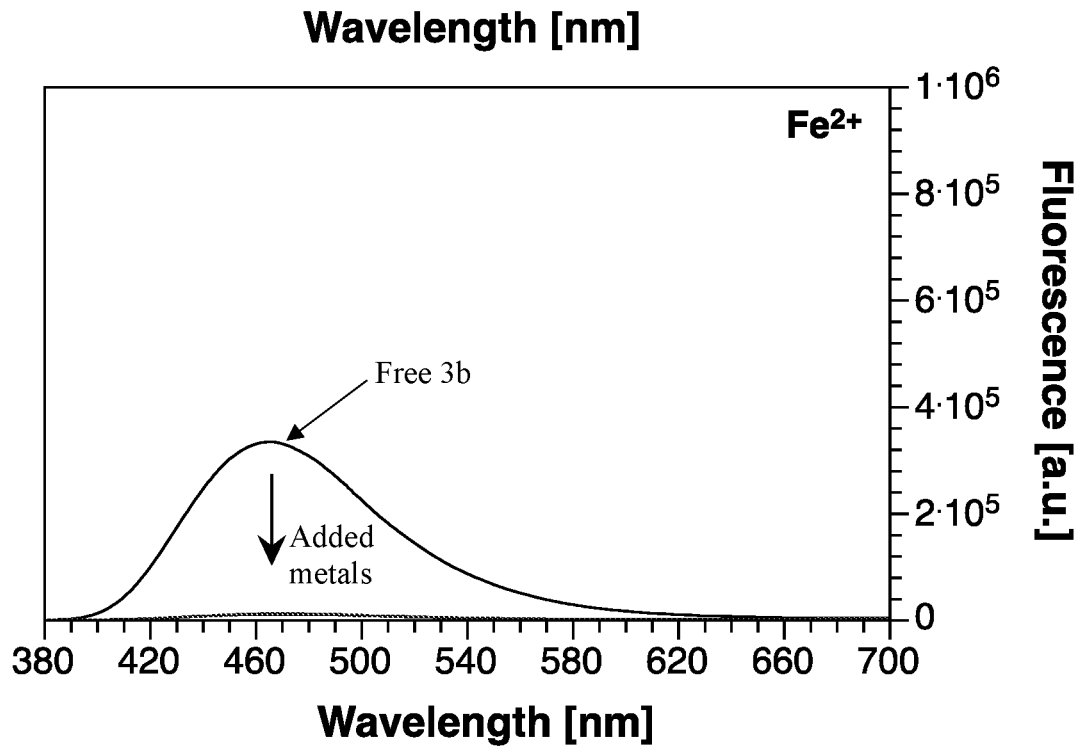
Figure 16E:
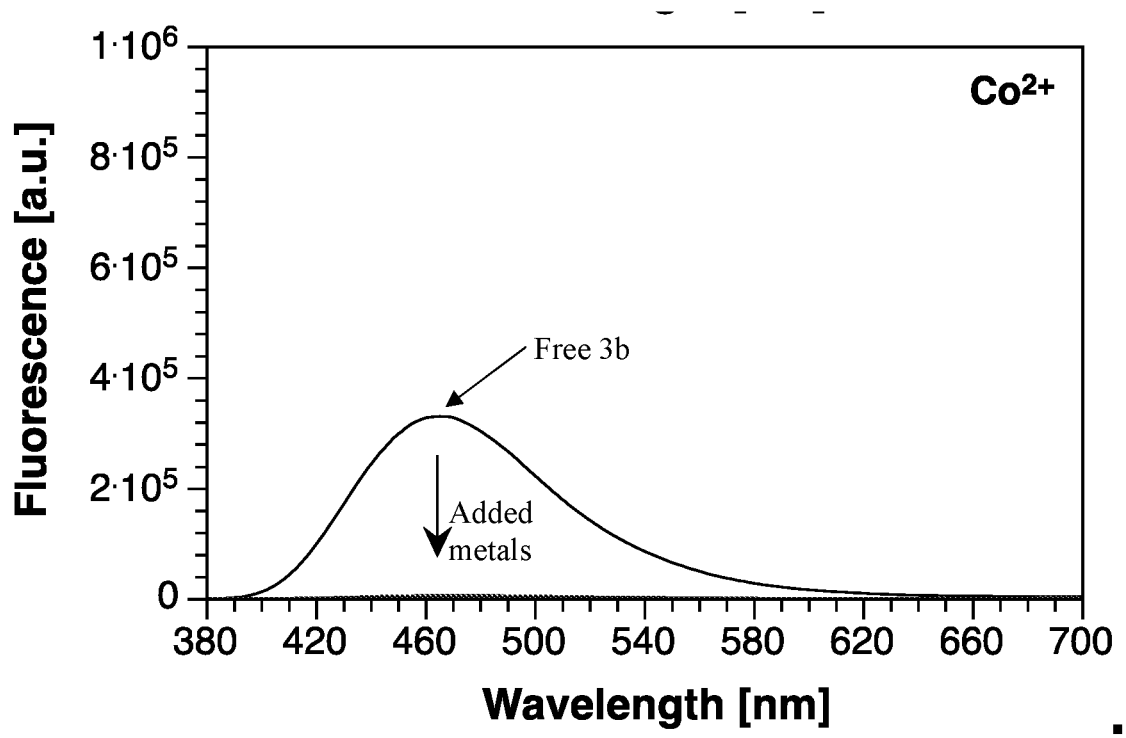
Figure 16F:
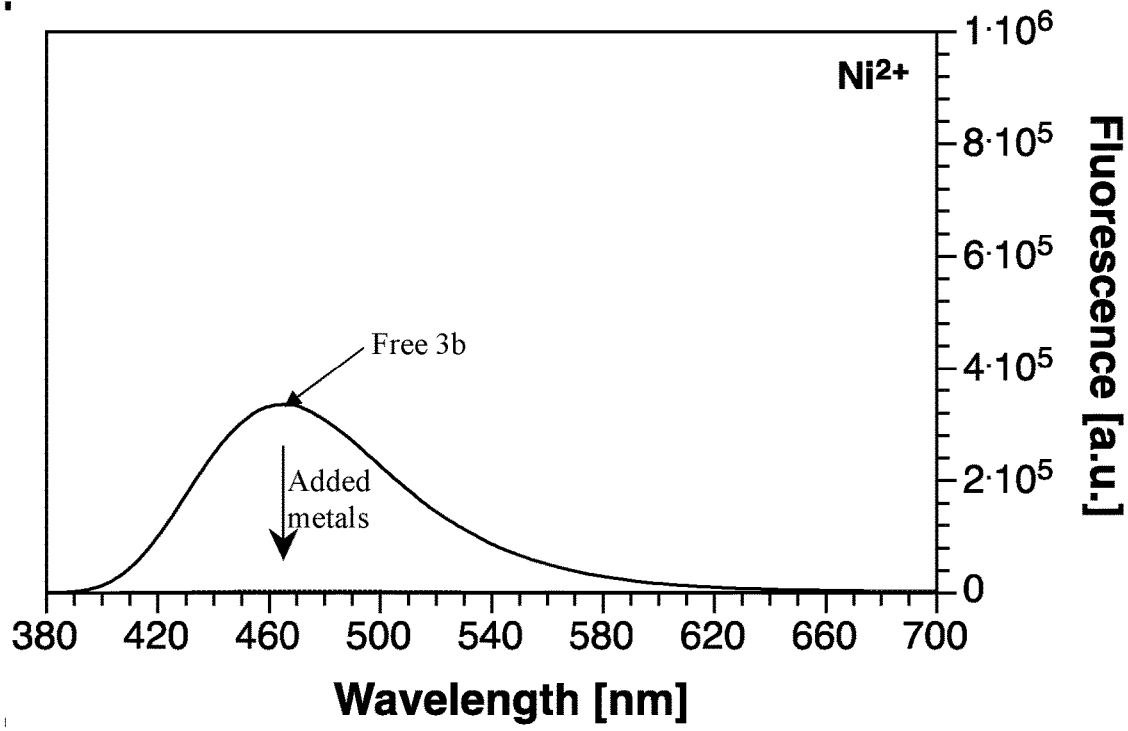
Figure 16G:
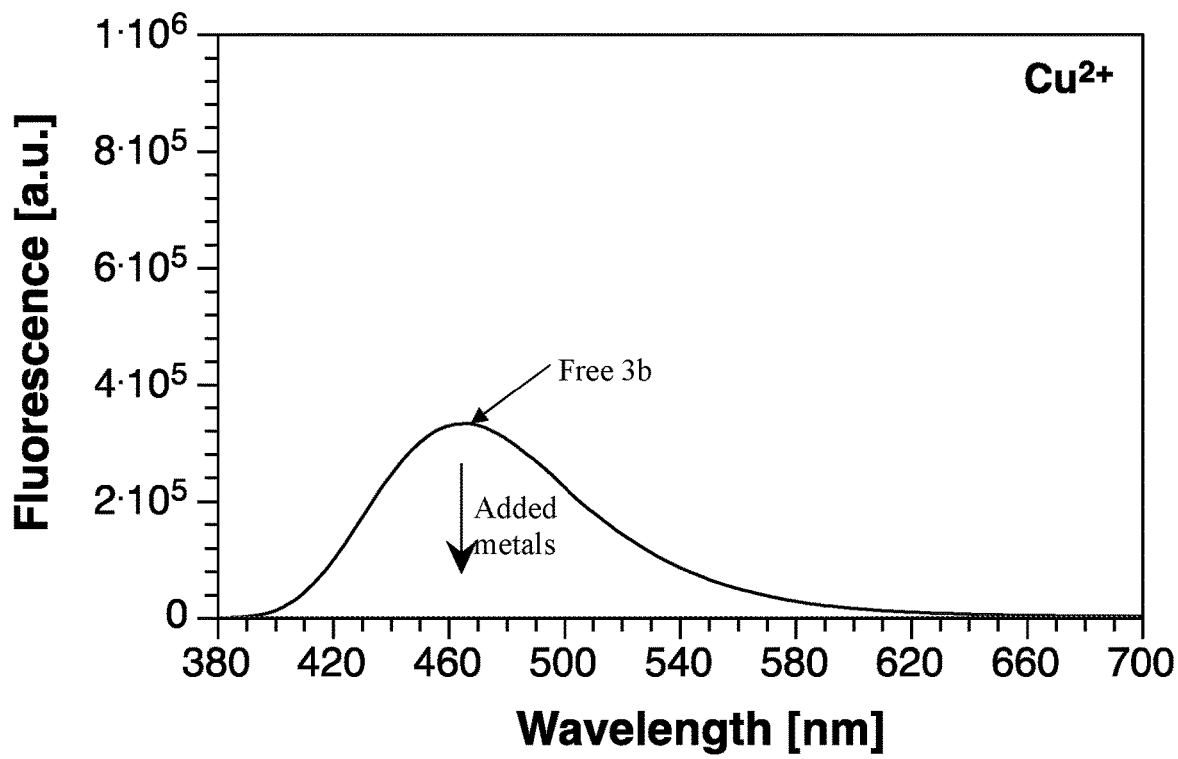
Figure 16H:
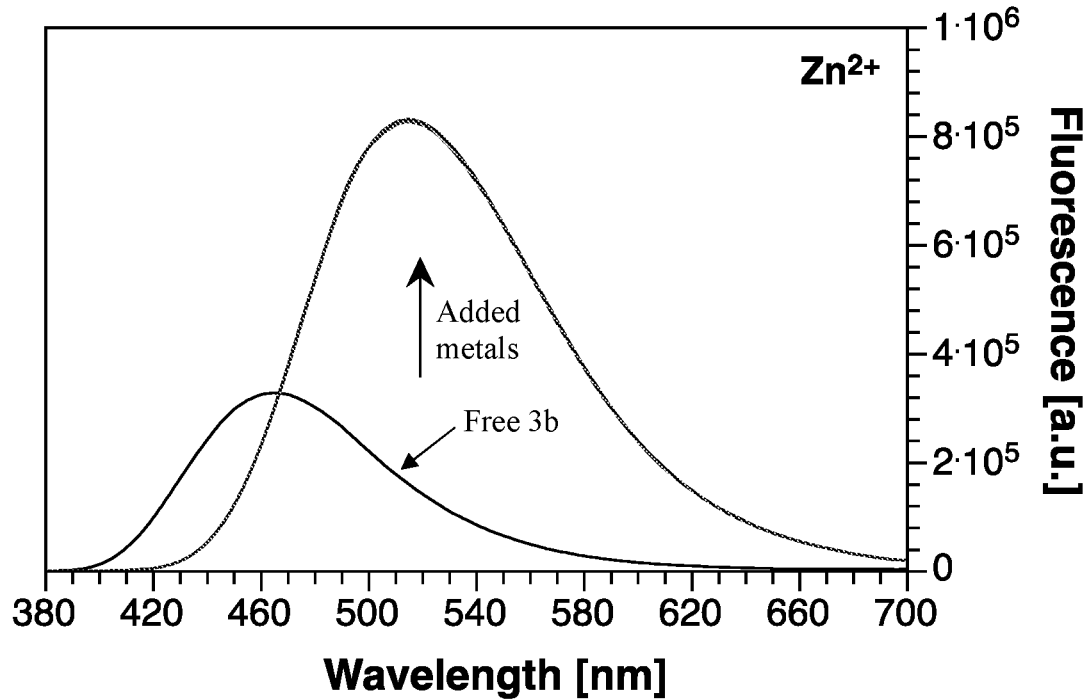
Figure 17A:
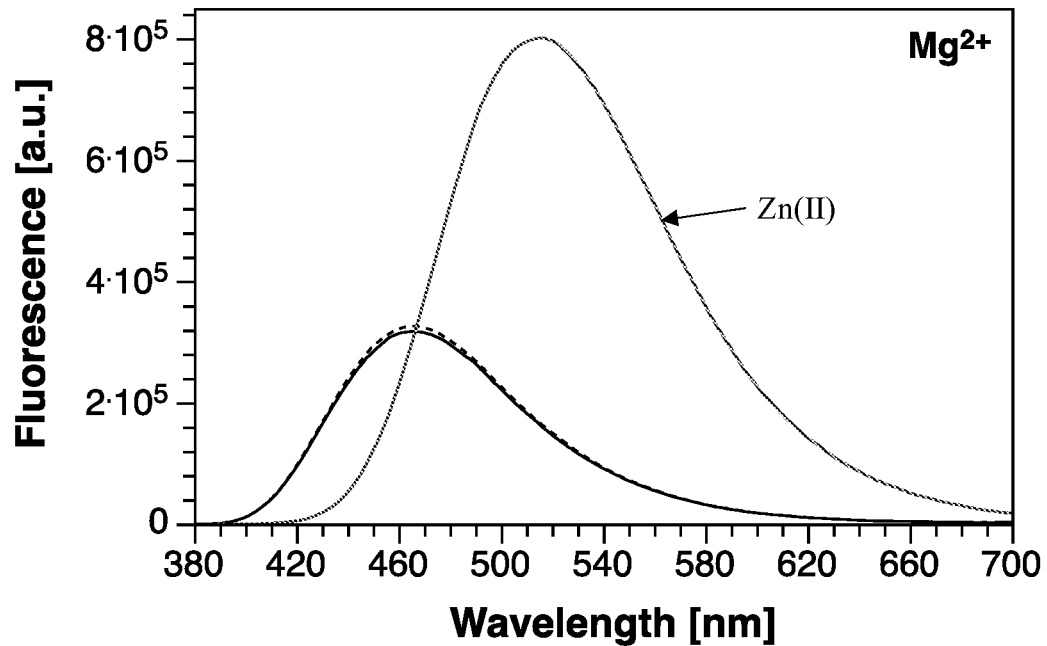
FIG. 17A-17H. Fluorescence response of compound 3b in the presence of 4.0 equivalents of interfering divalent metal ions.
Figure 17B:
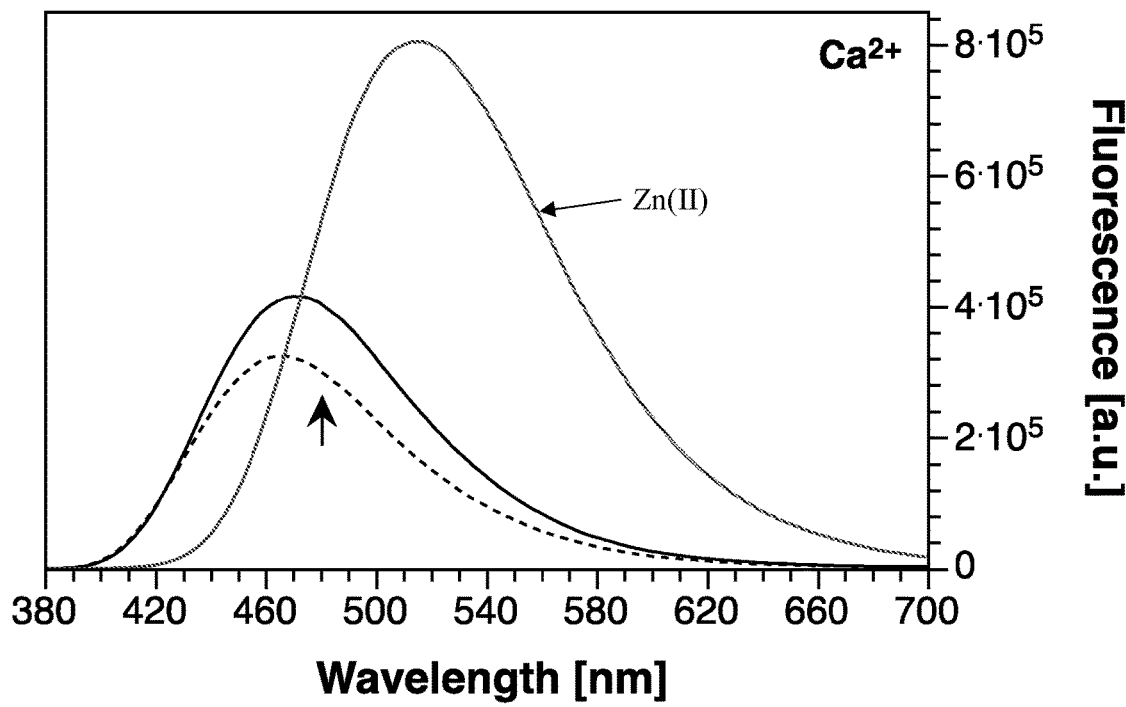
Figure 17C:
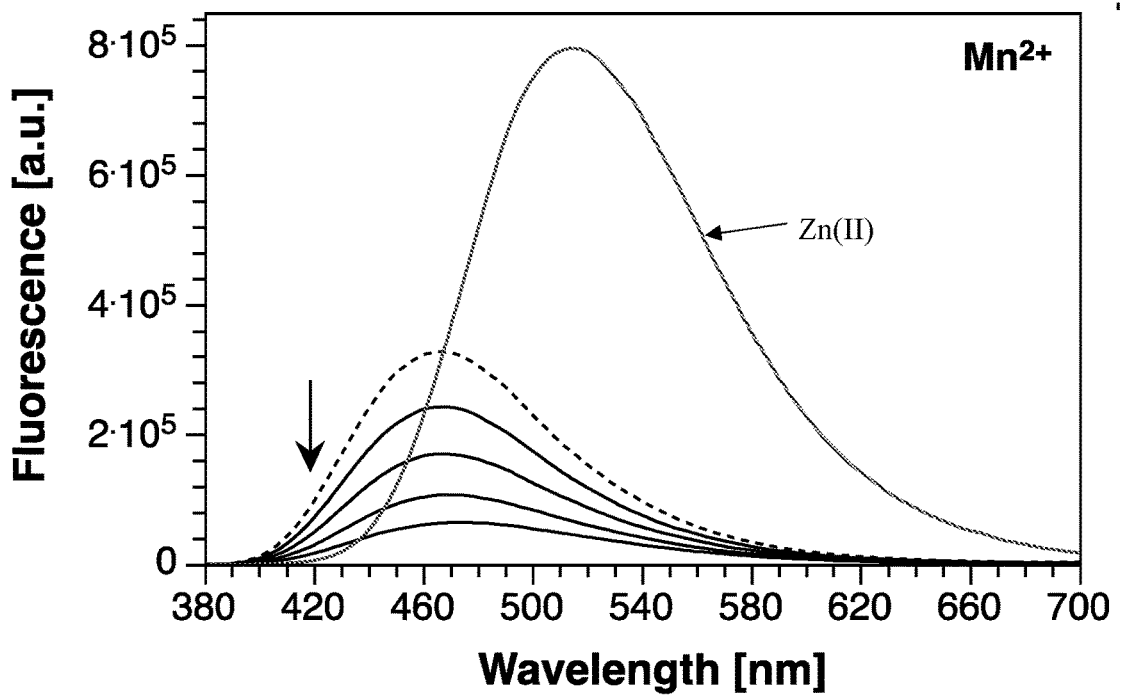
Figure 17D:
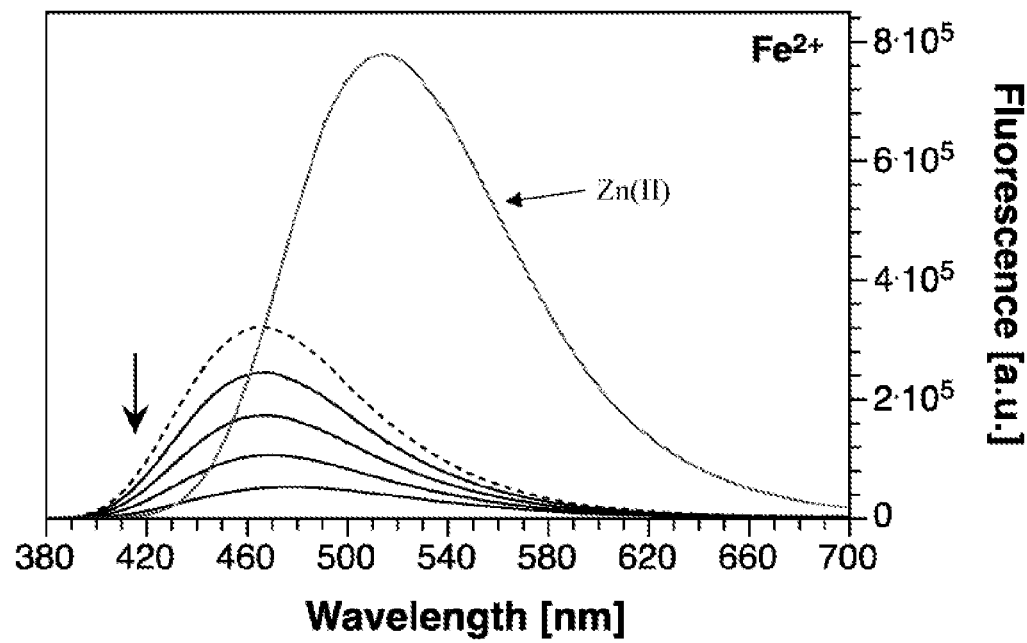
Figure 17E:
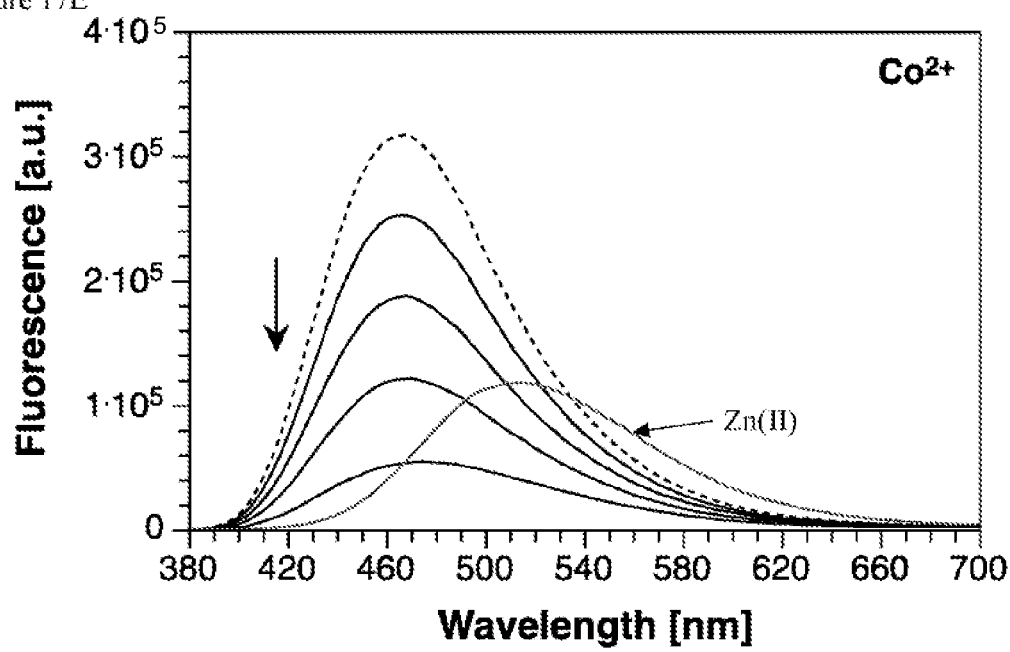
Figure 17F:
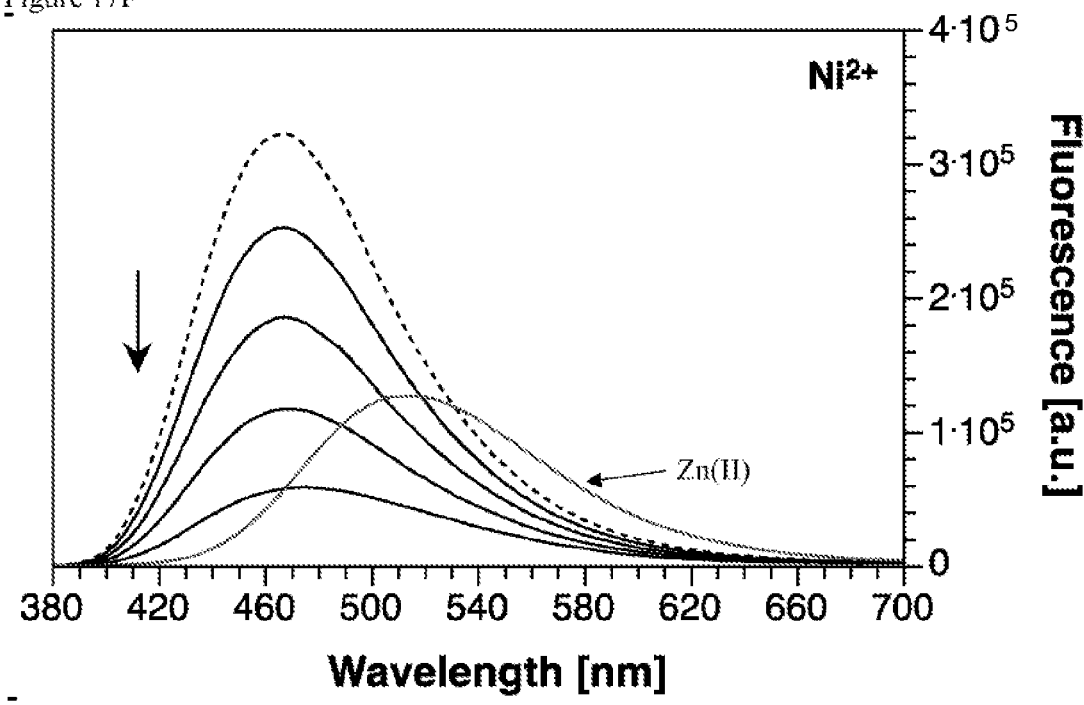
Figure 17G:
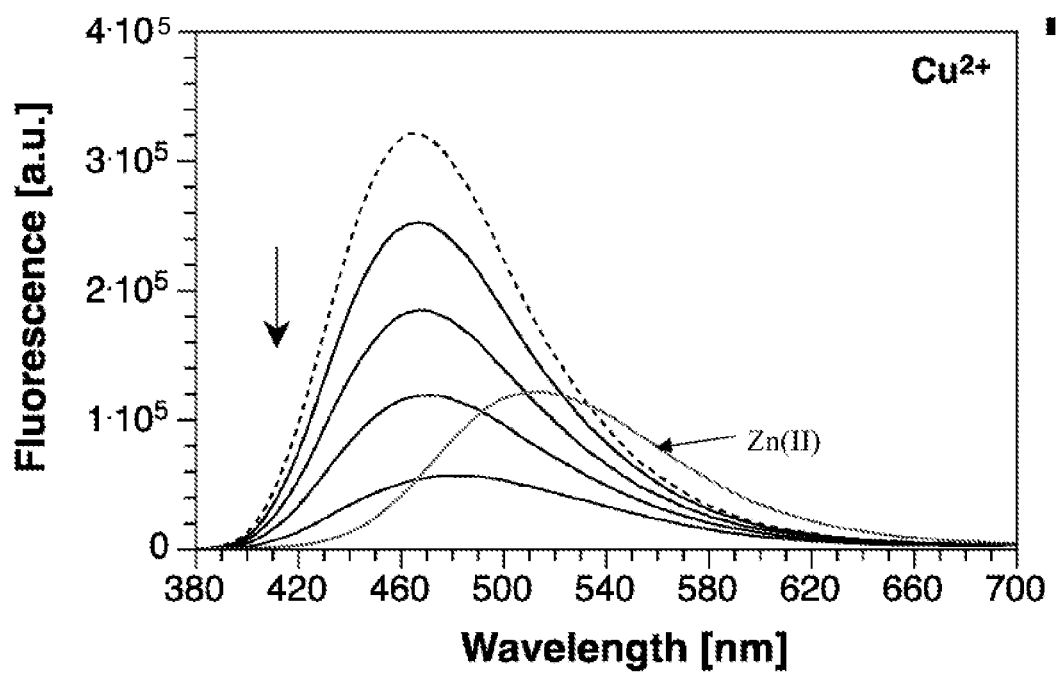
Figure 17H:
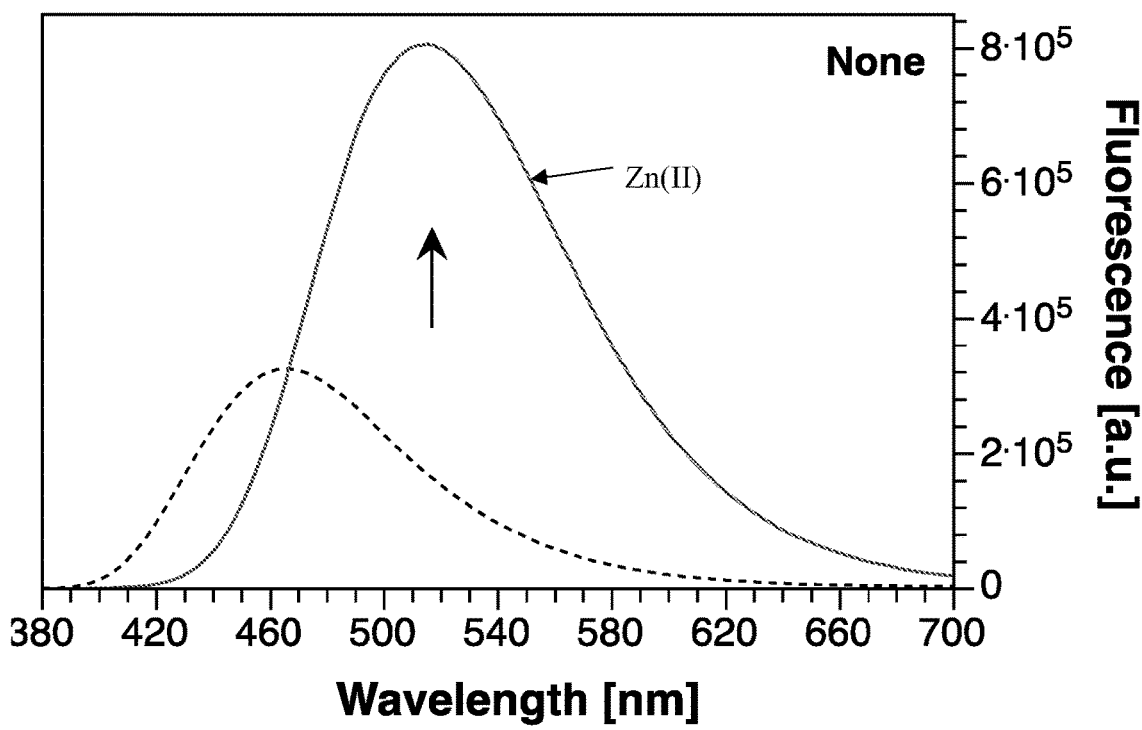

Analyte Selectivity of Ligand 3b. A 5 µM solution (30 mL) of 3b was prepared in pH 7.0 aqueous buffer (10 mM PIPES, 100 mM KCl, 25° C.) that had been previously equilibrated with Chelex® and filtered through a 0.2 µm filter. An aliquot (2.0 mL) of the solution was transferred to a quartz cuvette with a 1-cm path length, and a fluorescence spectrum was acquired over the emission range of 380-700 nm with excitation at 361 nm. Under magnetic stirring, the solution was supplemented with each divalent metal cation (4 µM for transitions metals, corresponding to 80% fractional saturation of 3b; 2 mM Ca(II) and Mg(II)), and a fluorescence spectrum was immediately acquired. The solution was then supplemented with ZnSO$_4$.7H$_2$O (1 mM stock solution in 18.2 MΩ.cm H$_2$O) to a final concentration of 1 µM (for Co(II), Ni(II), and Cu(II)) or 5 µM (for all other metals: Mg(II), Ca(II), Mn(II), Fe(II)), and a fluorescence spectrum was immediately acquired (FIG. 15). For Fe(II), the fluorescence spectrum was acquired after a 30-min equilibration to ensure that the [(3b)Zn(II)] complex had completely formed. The emission spectra corresponding to the addition of 80% fractional saturation with the interfering metal ions, as well as the addition of Zn(II) were integrated over the ranges of 440-495 nm (CH1) and 510-570 nm (CH$_2$), and the resulting intensities were computed as a ratio of CH2/CH1. Metal cations were supplied as aqueous stock solutions of the following salts: Mg(II), Ca(II) as chlorides (1 M stocks); Co(II) as CoN(O$_3$)$_2$ (1 µM stock); Mn(II), Fe(II), Cu(II), and Zn(II) as sulfates (1 µM stocks). To avoid aerial oxidation of Fe(II), the stock solution was freshly prepared in 10 mM H$_2$SO$_4$ before use.

To measure the fluorescence response of chromis-2 upon complete saturation of the probe, a 5 µM solution (15 mL) of chromis-2 was prepared in aqueous buffer (10 mM PIPES, 100 mM KCl, 25° C., pH 7.0) that had been supplemented with 2.0 equivalents (10 µM from a 30 mM stock solution in H$_2$O) of EDTA. A fluorescence spectrum was acquired of the free probe over the spectral window of 380-700 nm with excitation at 361 nm. The solution was supplemented with interfering divalent metal ions (30 mM stocks solutions of each metal in H$_2$O) to final concentrations of 20 and 40 µM, with a fluorescence spectrum acquired immediately after the addition of each aliquot (FIG. 16A-16H showing free 3b and FIGS. 17A-17H showing free 3.3b).

Figure 18:
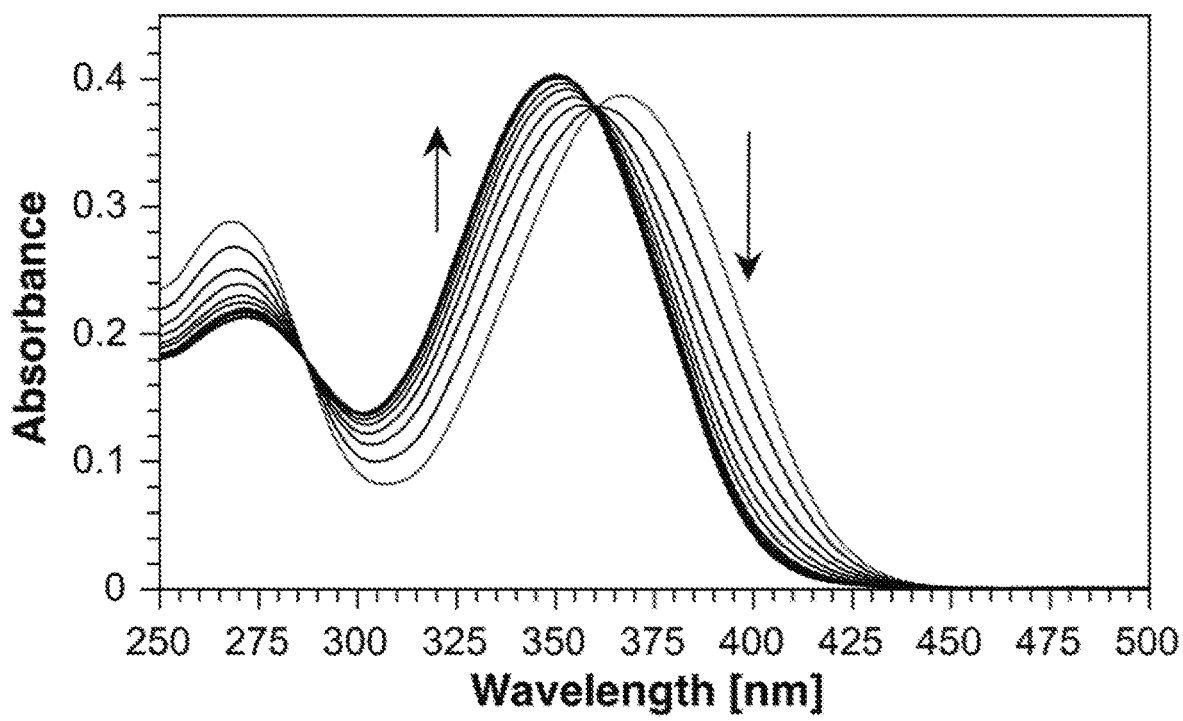
FIG. 18. Spectrophotometric determination of the Zn(II) stability constant of compound 3b via competition with HEDTA. Spectrophotometric titration of [(compound 3b)Zn (II)] with HEDTA as the competing ligand in pH 7.0 buffer (10 mM PIPES, 0.1 M KCl, 25° C.). The red trace represents the Zn(II)-saturated ligand before addition of HEDTA. Non-linear least-squares fitting of the absorbance data, showing the change in absorbance and corresponding fit at 366 nm. Fitting the absorbance data over the entire spectral window (250-500 nm) yielded an average Log $K_{Zn(II)L}$=11.0±0.05.

Determination of the Zn(II)-Binding Affinity of Ligand 3b. The Zn(II) stability constant of 3b was determined through a spectrophotometric titration using HEDTA [(2-hydroxyethyl)ethylenediaminetriacetic acid] as the competing ligand (FIG. 18). A 20 µM solution of 3b (from a 3 mM stock solution in H$_2$O) was equilibrated with equimolar ZnSO$_4$.7H$_2$O (from a 15 mM analytical stock solution in H$_2$O) in 3.00 mL of aqueous buffer (10 mM PIPES, 0.1 M KCl, pH 7.0) at 25° C. The in situ-generated [(3b)Zn(II)] complex was then titrated with HEDTA (from a 1.5 mM analytical stock solution in H$_2$O) from 4-40 µM. After the addition of each aliquot of HEDTA, the solution was equilibrated by magnetic stirring, and an absorbance spectrum was acquired over the spectral window of 250-500 nm. The absorbance data were analyzed by non-linear least-squares fitting using Specfit[3] to provide an average Log K=11.0±0.05.

Fluorescence Comparison of 3b and chromis-2 (4). Fluorescence comparison measurements of 3b and chromis-2 were conducted in deuterated and non-deuterated buffer (10 mM PIPES, 100 mM KCl, pH/D 7.0, 25° C.). A quartz cuvette with a 1-cm path length containing 3.0 mL of aqueous buffer was supplemented with 5 µM 3b (from a 3 mM stock solution in H$_2$O), and after a 30-second equilibration via magnetic stirring, a fluorescence spectrum was acquired over the spectral window of 380-700 nm with excitation at 361 nm. The probe was then saturated with 5 µM ZnSO$_4$.7H$_2$O (from a 3 mM stock solution in H$_2$O), and a fluorescence spectrum was acquired. This was repeated for 3b in deuterated buffer, but with supplementation of 5 µM ZnSO$_4$.7H$_2$O from a 3 mM stock solution in D$_2$O. To compare the fluorescence intensities and profiles of 3b to chromis-2, these procedures were repeated, except that the buffers were supplemented with 5 µM chromis-2 from a 3 mM stock solution in DMSO.

Molar Ratio Titration of Chromis-2 with Zn(II). A 10 µM solution of chromis-2 in 3.0 mL of pH 7.0 buffer (10 mM PIPES, 0.1 M KCl, 25° C.) prepared in a quartz cuvette with a 1-cm pathlength was titrated with ZnSO$_4$.7H$_2$O (from a 3 mM aqueous stock solution) in 1 µM (0.1 eq.) increments. After each aliquot, the solution was equilibrated for 30 seconds by magnetic stirring, and an absorbance (spectral window: 250-500 nm) and fluorescence spectrum (excitation: 361 nm, spectral window: 380-700 nm) were acquired.

Figure 19A:
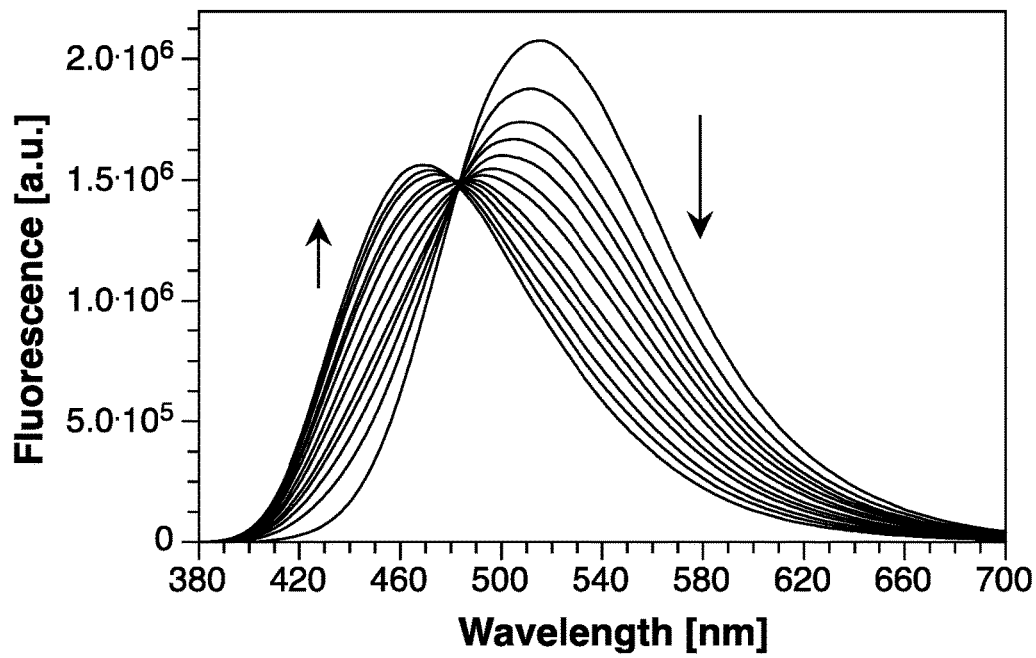
FIG. 19A-19B. Spectrophotometric determination of the Zn(II) stability constant of ligand chromis-2 (compound 4) via competition with EGTA.
Figure 19B:
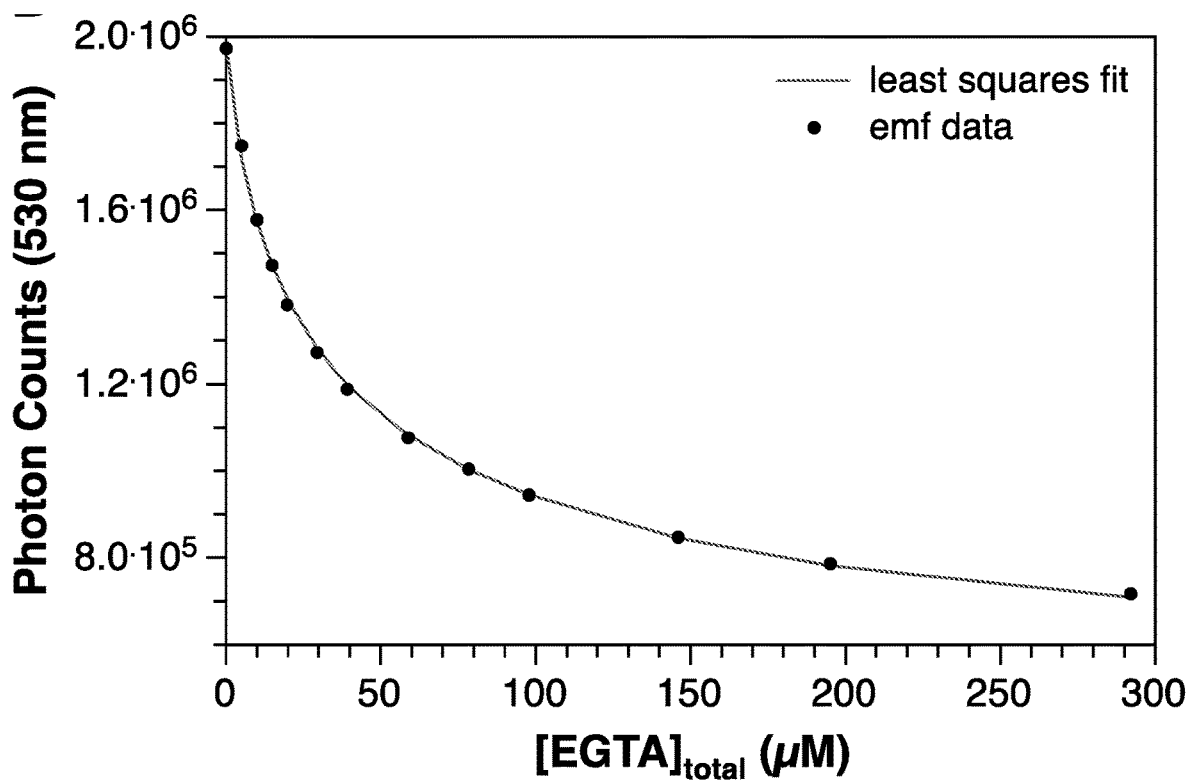
Figure 20A:
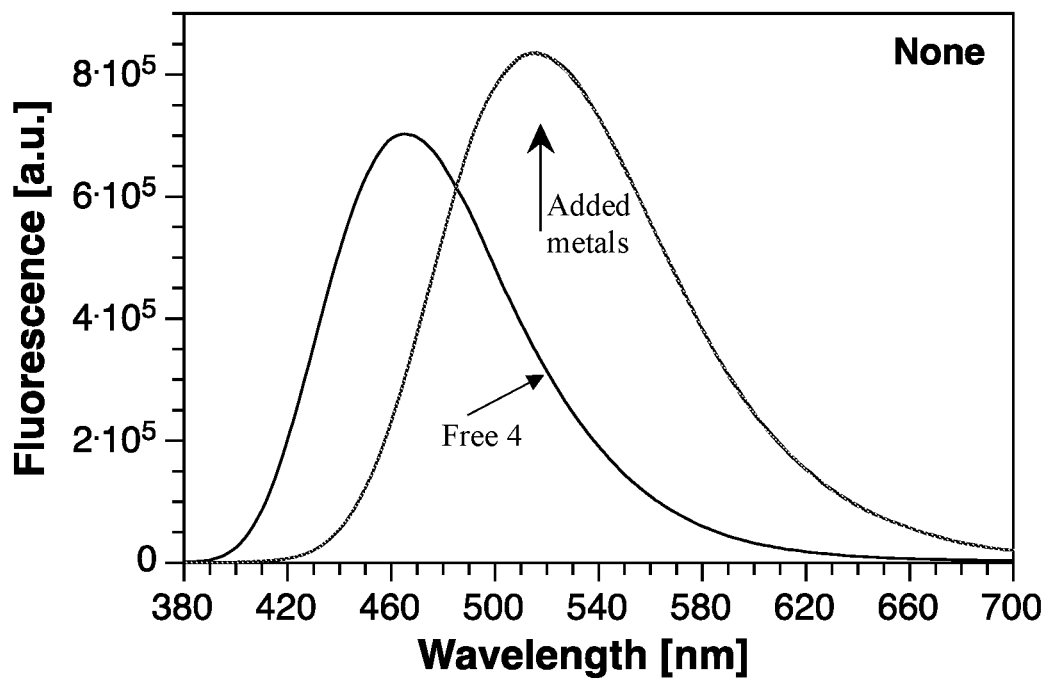
FIG. 20A-20H. Fluorescence response of chromis-2 in the presence of 4.0 equivalents of interfering divalent metal ions.
Figure 20B:
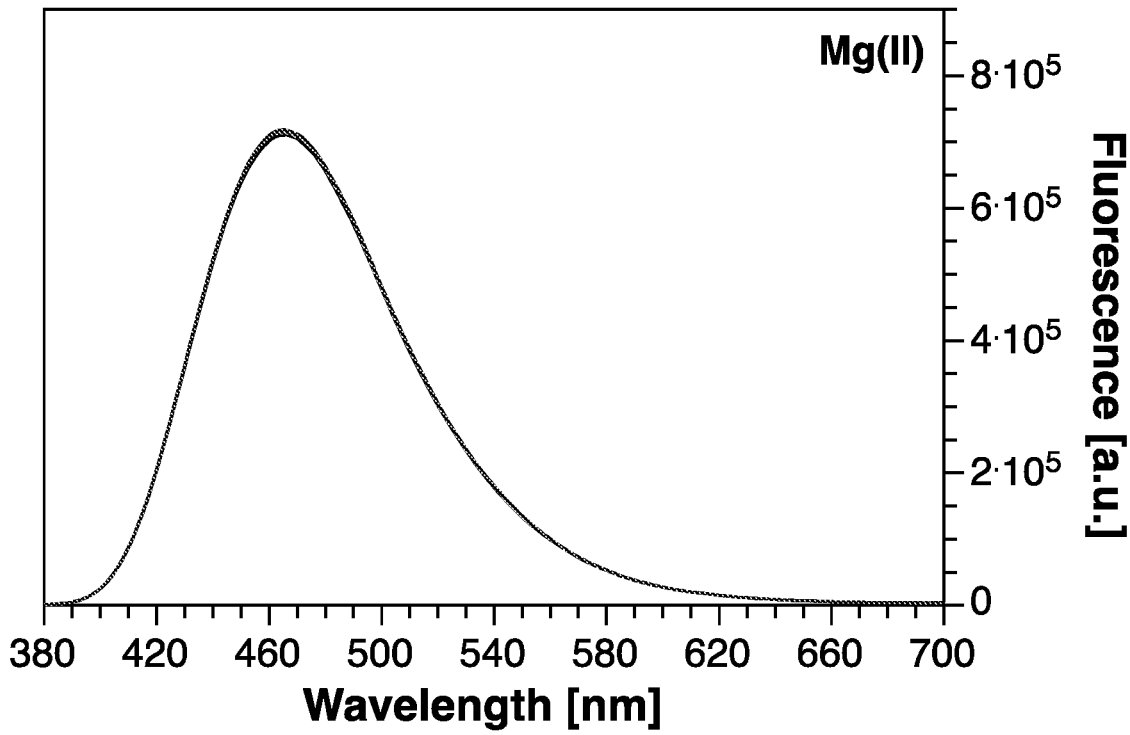
Figure 20C:
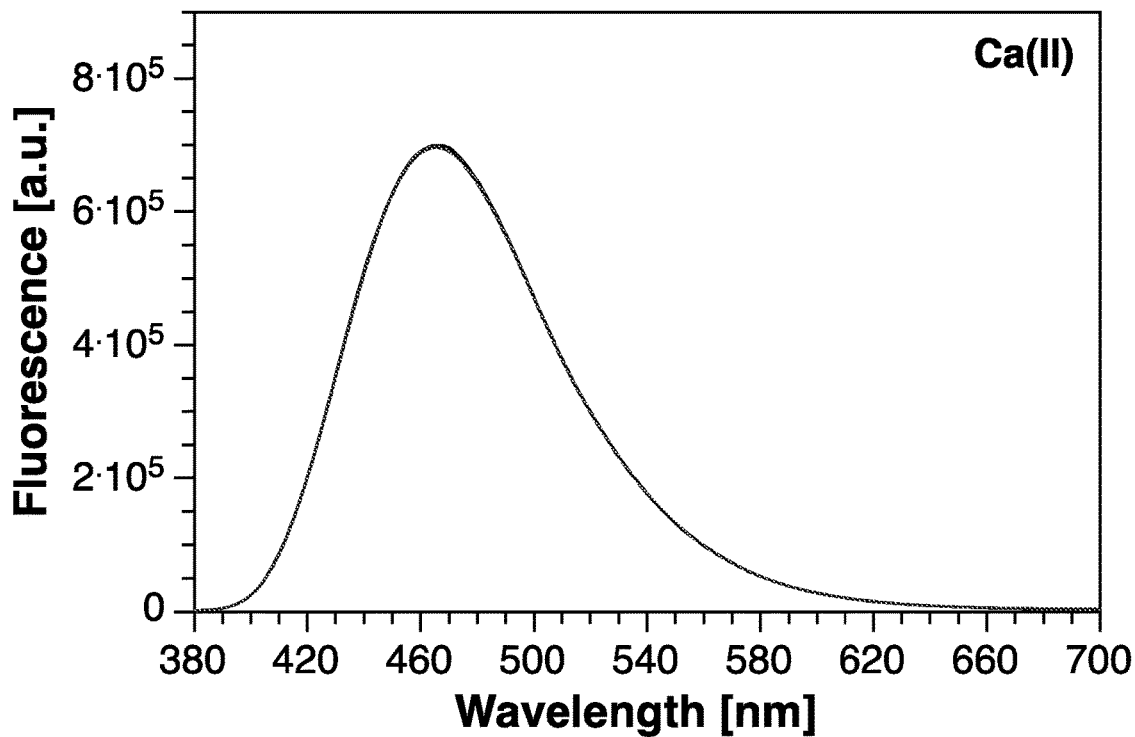
Figure 20D:
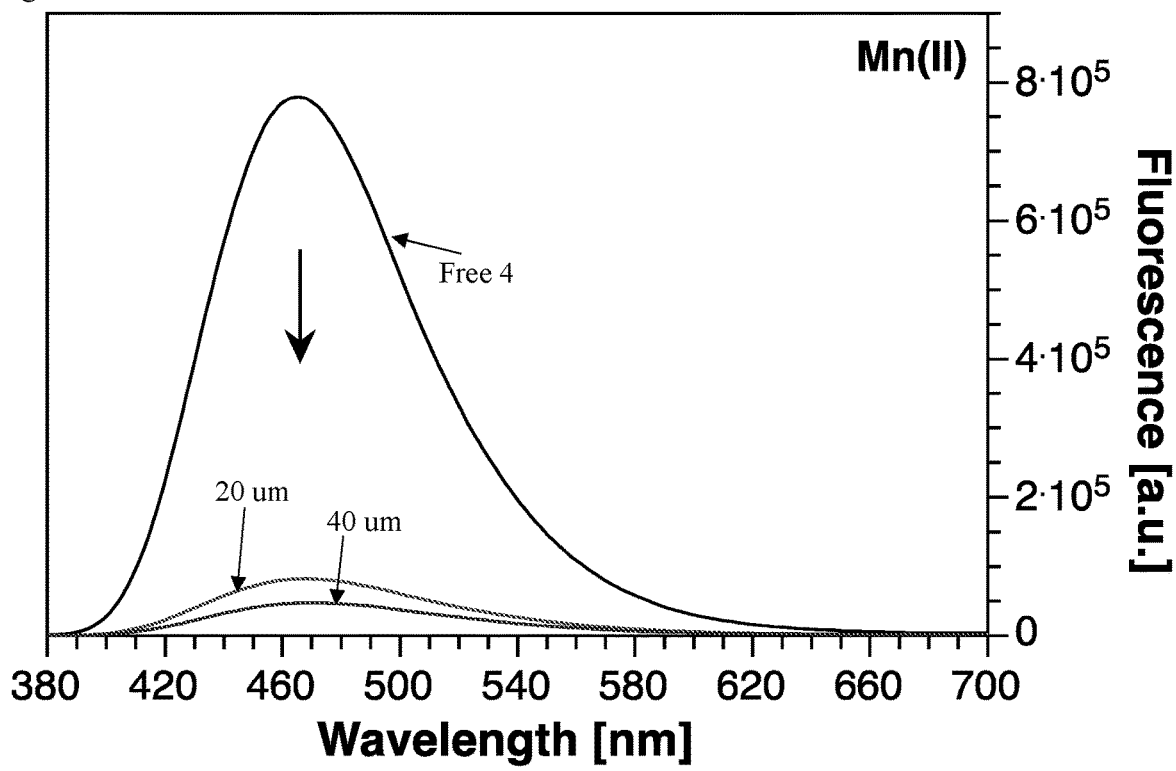
Figure 20E:
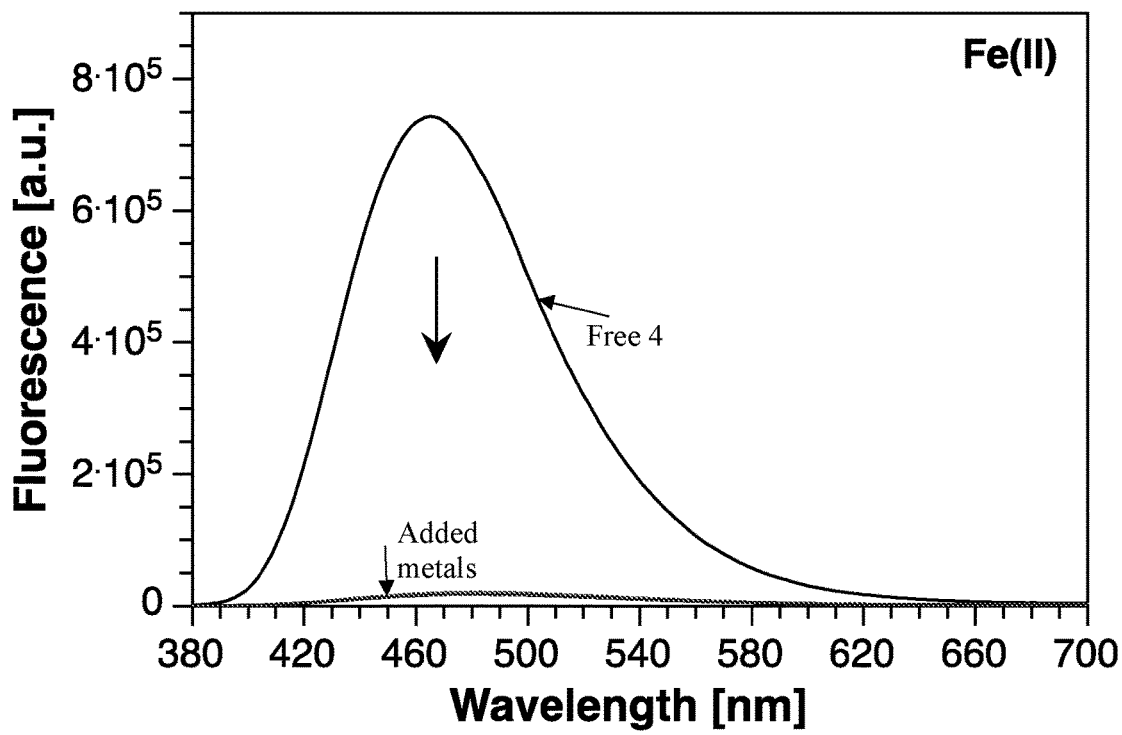
Figure 20F:
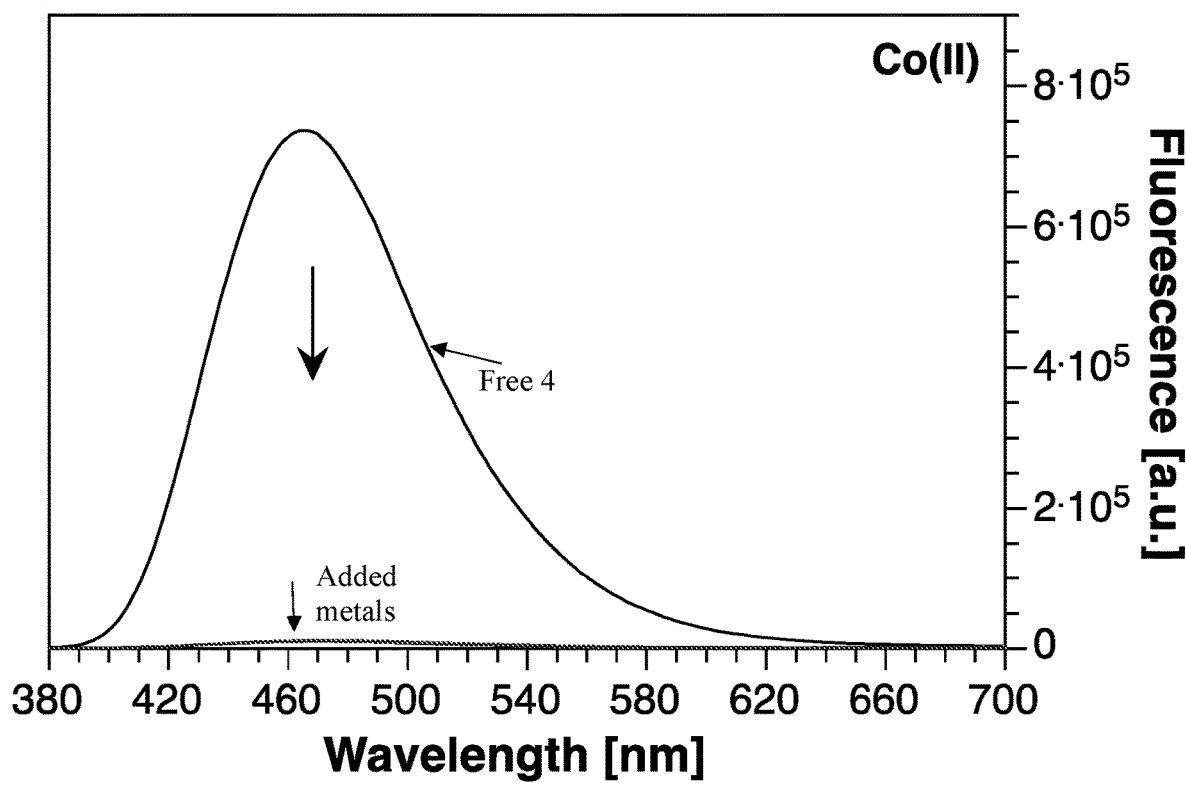
Figure 20G:
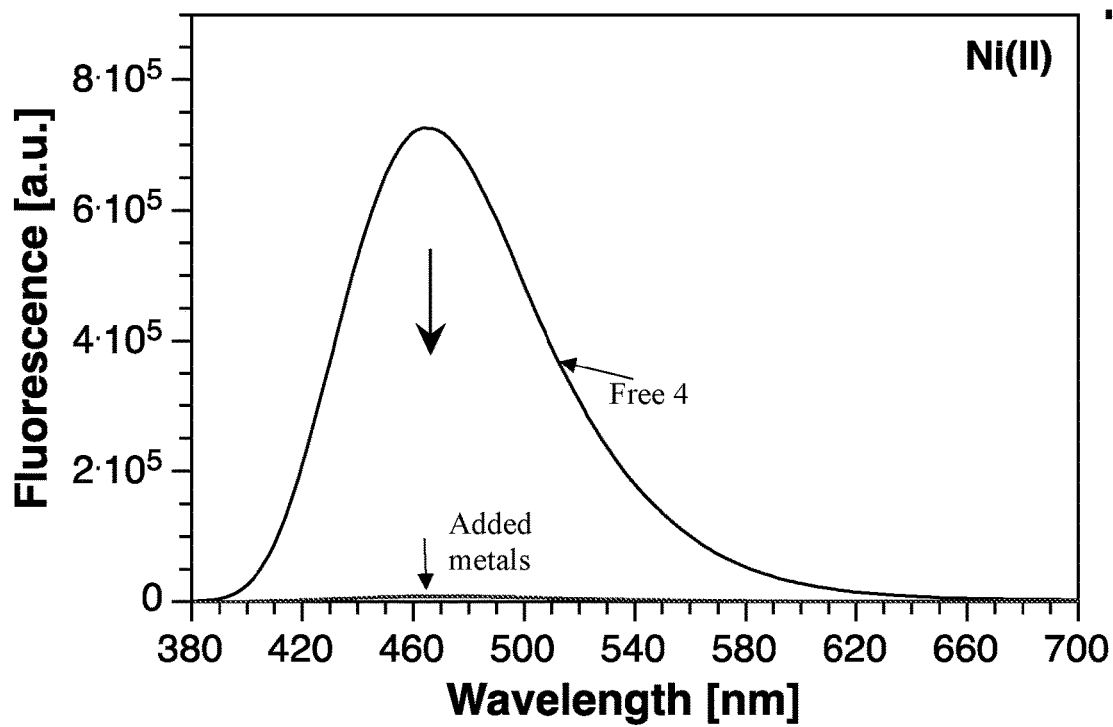
Figure 20H:
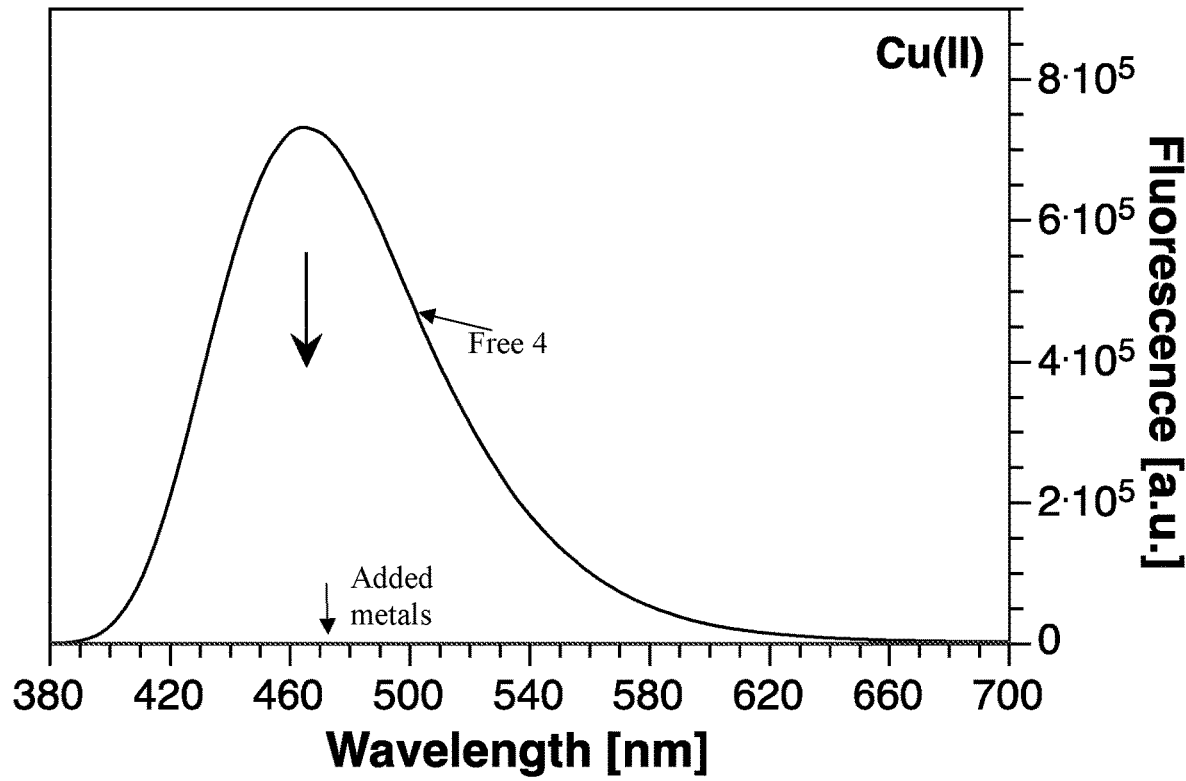
Figure 21A:
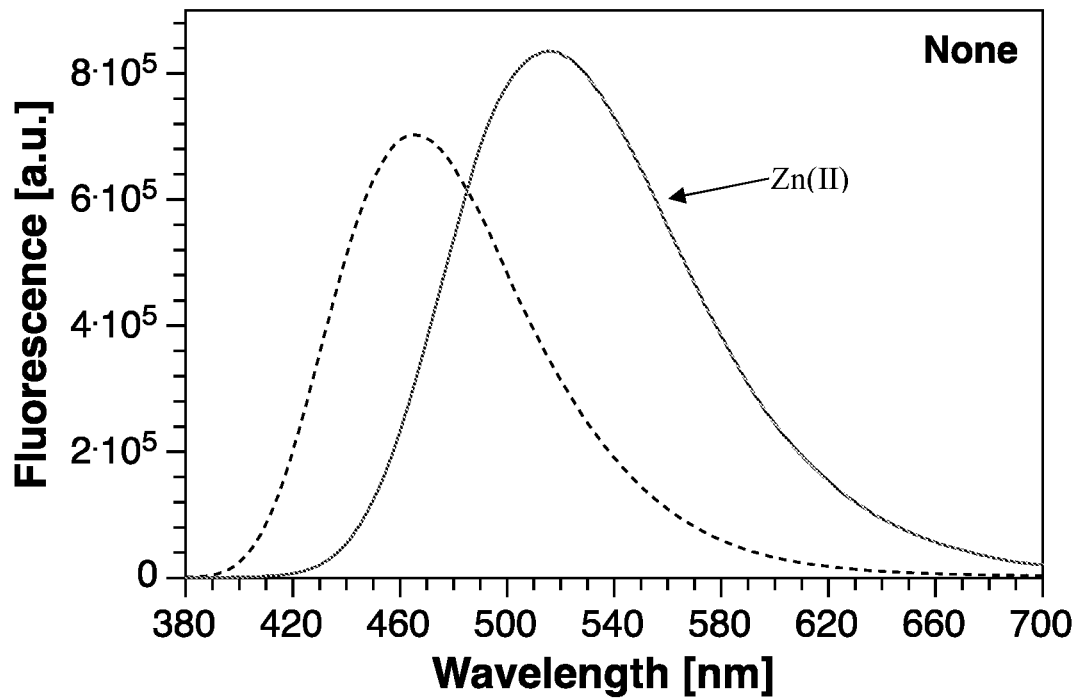
FIG. 21A-21H. Fluorescence response of chromis-2 in the presence of 4.0 equivalents of interfering divalent metal ions.
Figure 21B:
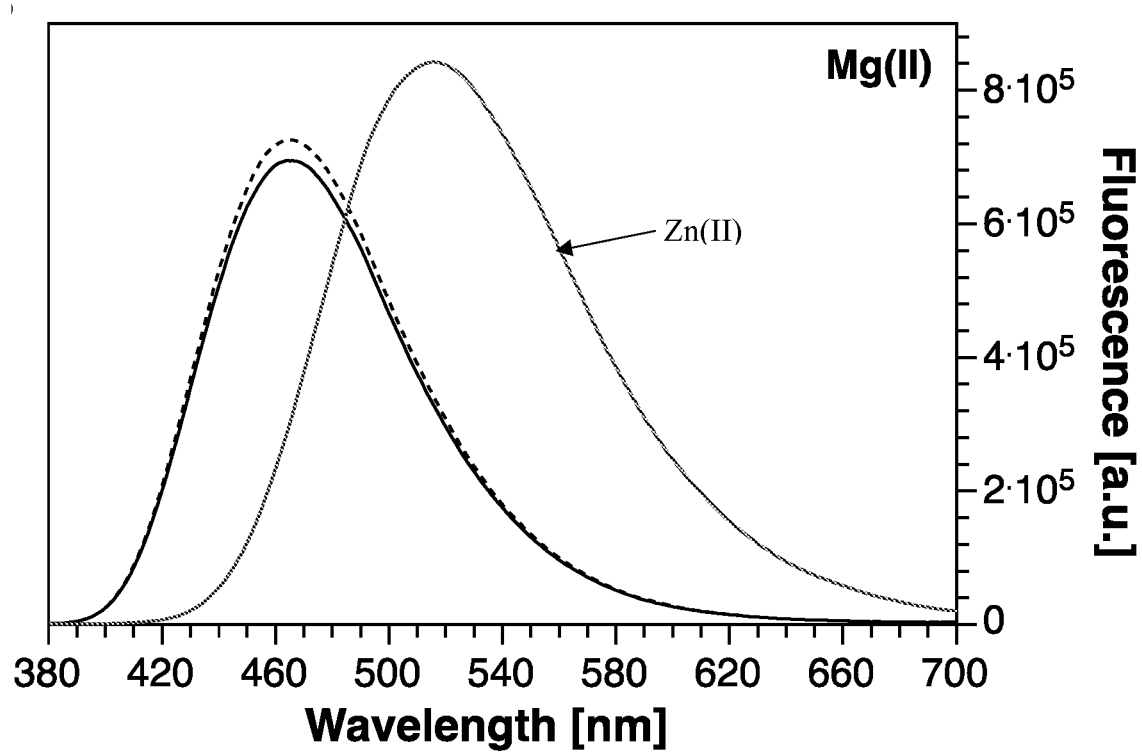
Figure 21C:
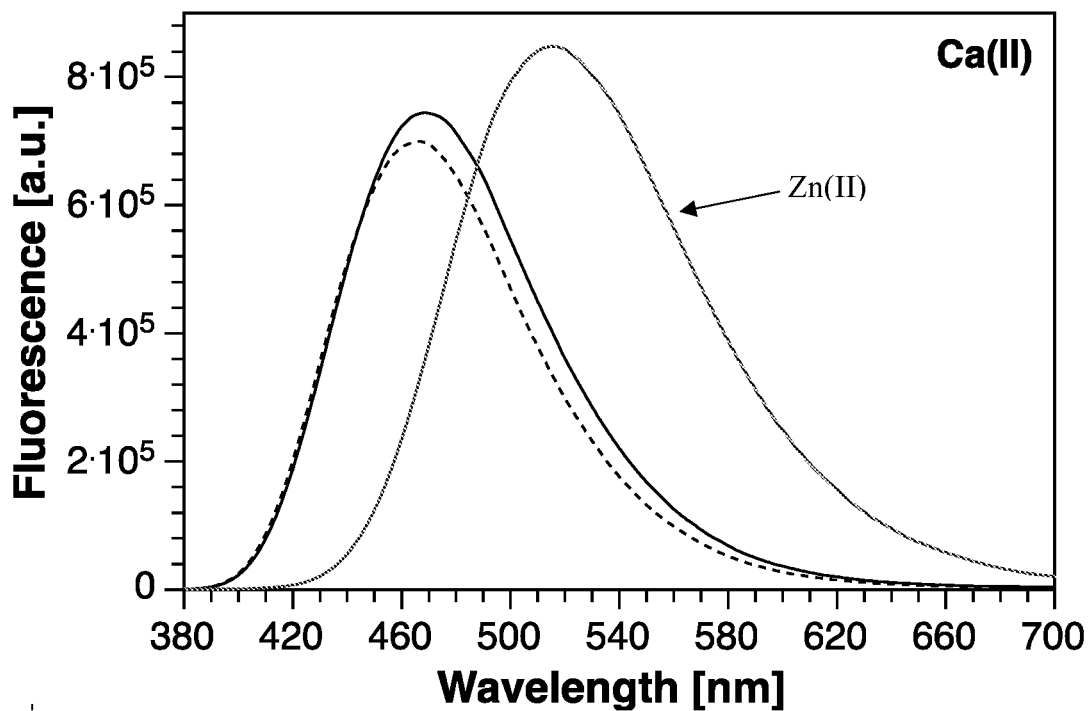
Figure 21D:
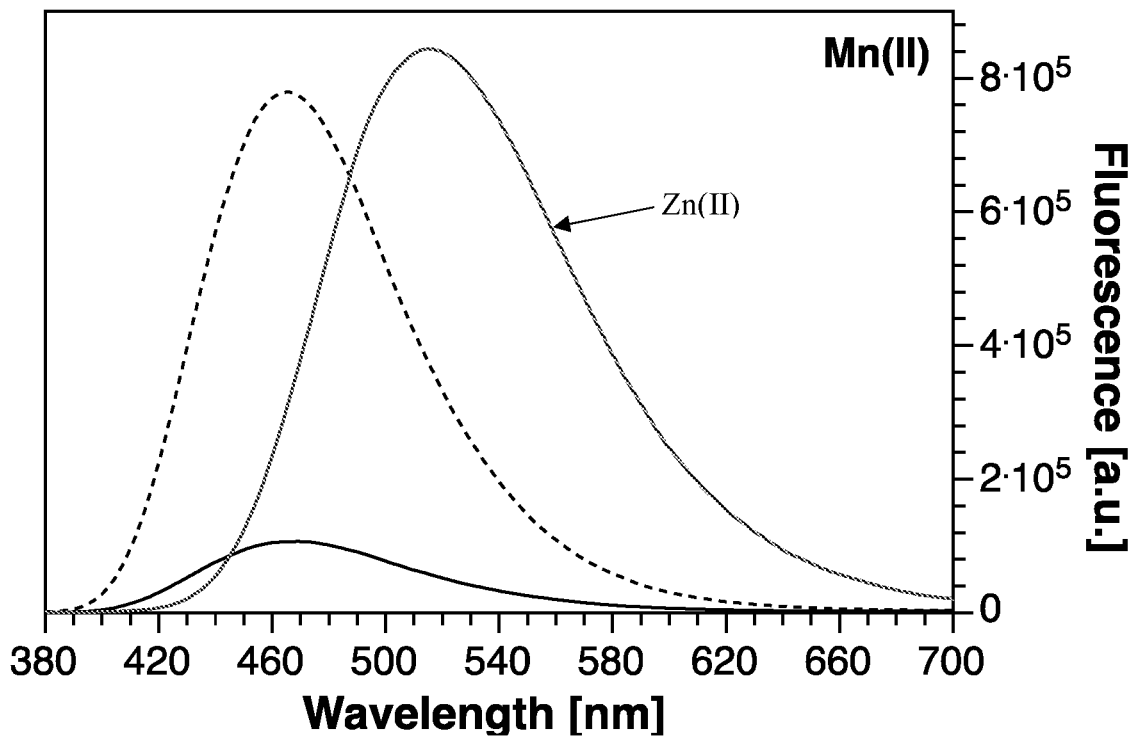
Figure 21E:
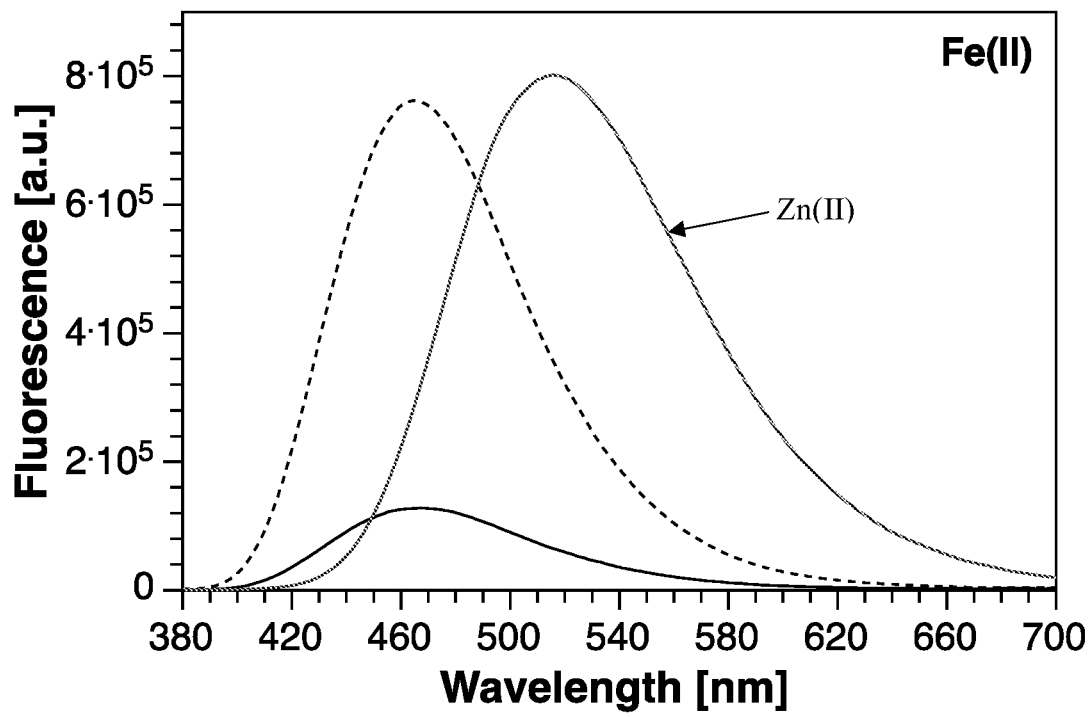
Figure 21F:
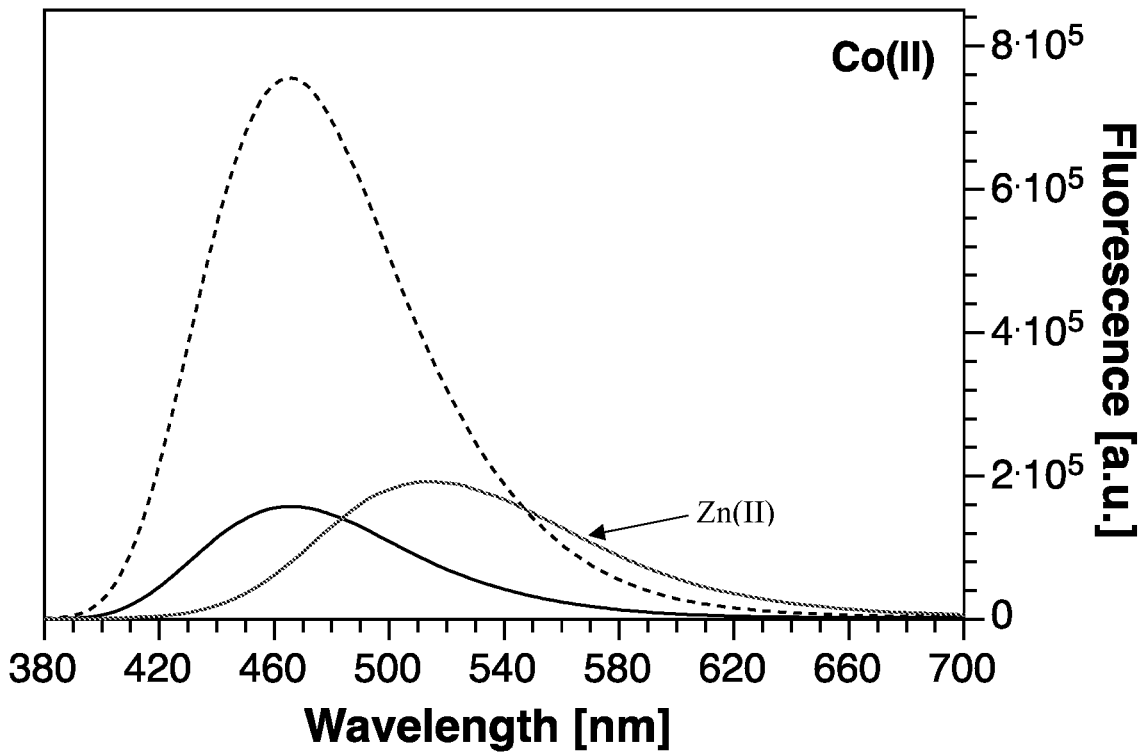
Figure 21G:
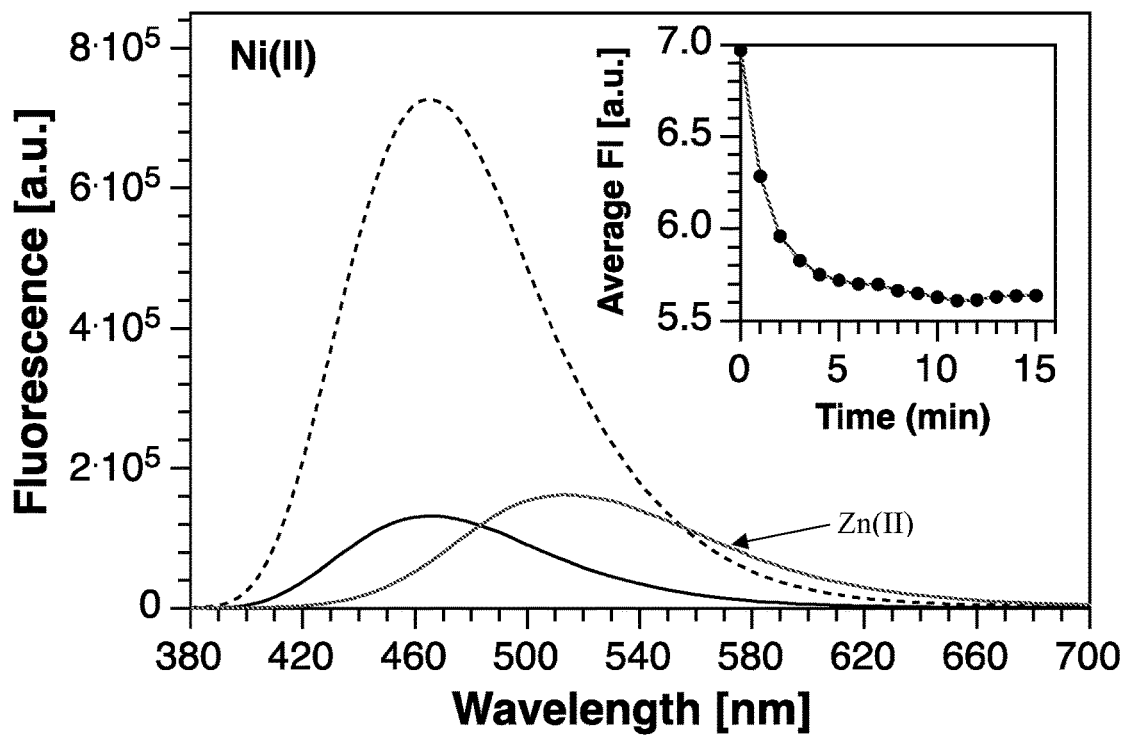
Figure 21H:
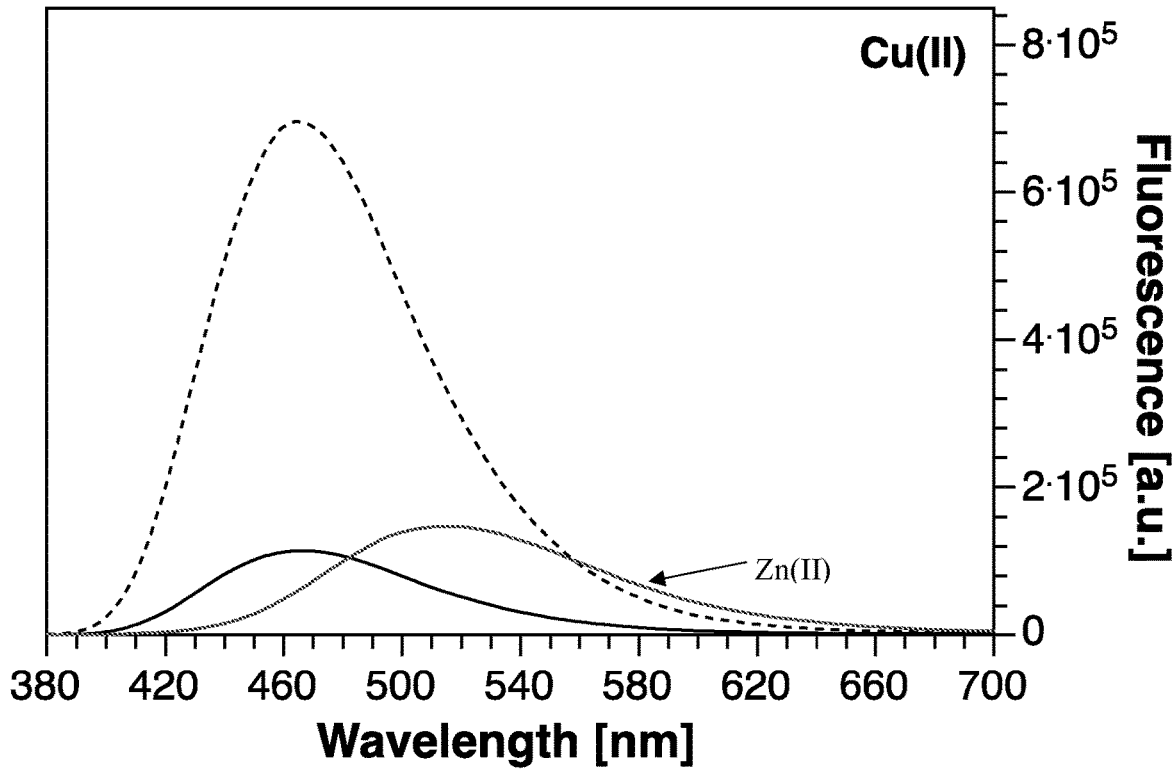

Determination of the Zn(II)-Binding Affinity of Chromis-2. The Zn(II) stability constant of chromis-2 was determined via a fluorimetric titration using EGTA [Ethylene glycol-bis (2-aminoethylether)-N,N,N',N'-tetraacetic acid] as the competing ligand (FIG. 19A-19B). A 10 µM solution of chromis-2 (from a 3 mM stock solution in DMSO) was equilibrated with 10 µM ZnSO$_4$.7H$_2$O (from a 5 mM analytical stock solution in H$_2$O) in 3.00 mL of aqueous buffer (10 mM PIPES, 0.1 M KCl, pH 7.0) at 25° C. The in situ-generated [(chromis-2)Zn(II)] complex was then titrated with EGTA (from 3, 20, and 300 mM analytical stock solutions in H$_2$O) from 0-300 µM. After the addition of each aliquot of EGTA, the solution was equilibrated by magnetic stirring, and a fluorescence spectrum was acquired over the spectral window of 380-700 nm with excitation at 361 nm. The fluorescence data were analyzed by non-linear least-squares fitting using the Specfit software to provide an average Log K=7.97±0.03 (FIG. 19A-19B).

Analyte Selectivity of Chromis-2. A 5 μM solution (40 mL) of chromis-2 was prepared in pH 7.0 aqueous buffer (10 mM PIPES, 100 mM KCl, 25° C.) that had been previously equilibrated with Chelex (1% w/v, Biorad) and filtered through a 0.2 μm filter. An aliquot (2.0 mL) of the solution was transferred to a quartz cuvette with a 1-cm path length, and a fluorescence spectrum was acquired over the emission range of 380-700 nm with excitation at 361 nm. Under magnetic stirring, the solution was supplemented with each divalent metal cation (4 μM for transitions metals, corresponding to 80% fractional saturation of 3b; 2 mM Ca(II) and Mg(II)), and a fluorescence spectrum was immediately acquired (FIG. 20A-20H). The solution was then supplemented with $ZnSO_4.7H_2O$ (1 mM stock solution in 18.2 MΩ.cm $H_2O$) to a final concentration of 1 μM (for Co(II), Ni(II), and Cu(II)) or 5 μM (for all other metals: Mg(II), Ca(II), Mn(II), Fe(II)), and a fluorescence spectrum was immediately acquired (FIG. 21A-21H). For Fe(II), the fluorescence spectrum was acquired after a 30-min equilibration to ensure that the [(3b)Zn(II)] complex had completely formed. The emission spectra corresponding to the addition of 80% fractional saturation with the interfering metal ions, as well as the addition of Zn(II) were integrated over the ranges of 440-495 nm ($CH_1$) and 510-570 nm ($CH_2$), and the resulting intensities were computed as a ratio of $CH_2/CH_1$. Metal cations were supplied as aqueous stock solutions of the following salts: Mg(II), Ca(II) as chlorides (1 M stocks); Co(II) as $Co(NO_3)_2$ (1 mM stock); Mn(II), Fe(II), Cu(II), and Zn(II) as sulfates (1 mM stocks). To avoid aerial oxidation of Fe(II), the stock solution was freshly prepared in 10 mM $H_2SO_4$ before use.

To measure the fluorescence response of chromis-2 upon complete saturation of the probe, a 5 μM solution (15 mL) of chromis-2 was prepared in aqueous buffer (10 mM PIPES, 100 mM KCl, 25° C., pH 7.0) that had been supplemented with 2.0 equivalents (10 μM from a 30 mM stock solution in $H_2O$) of EDTA. A fluorescence spectrum was acquired of the free probe over the spectral window of 380-700 nm with excitation at 361 nm. The solution was supplemented with interfering divalent metal ions (30 mM stocks solutions of each metal in $H_2O$) to final concentrations of 20 and 40 μM, with a fluorescence spectrum acquired immediately after the addition of each aliquot.

Figure 22A:
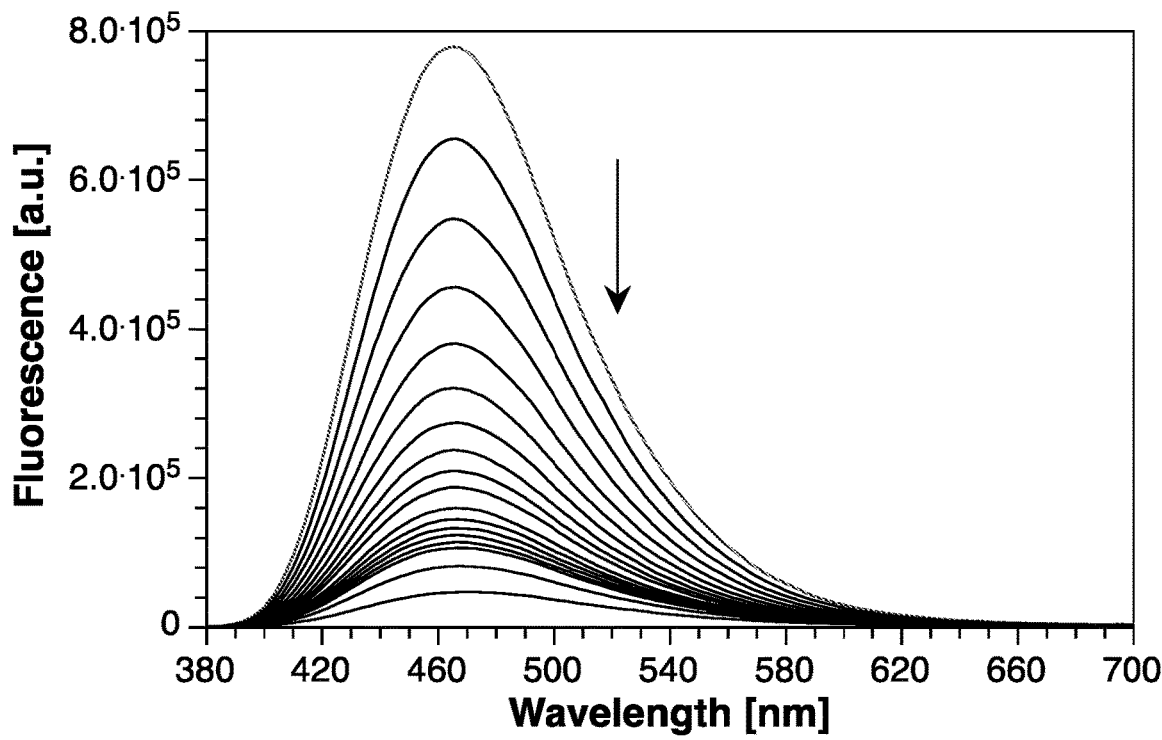
FIG. 22A-22B. Fluorimetric determination of the Mn(II) stability constant of chromis-2 (compound 4, 5 μM) via a metal-addition titration.
Figure 22B:
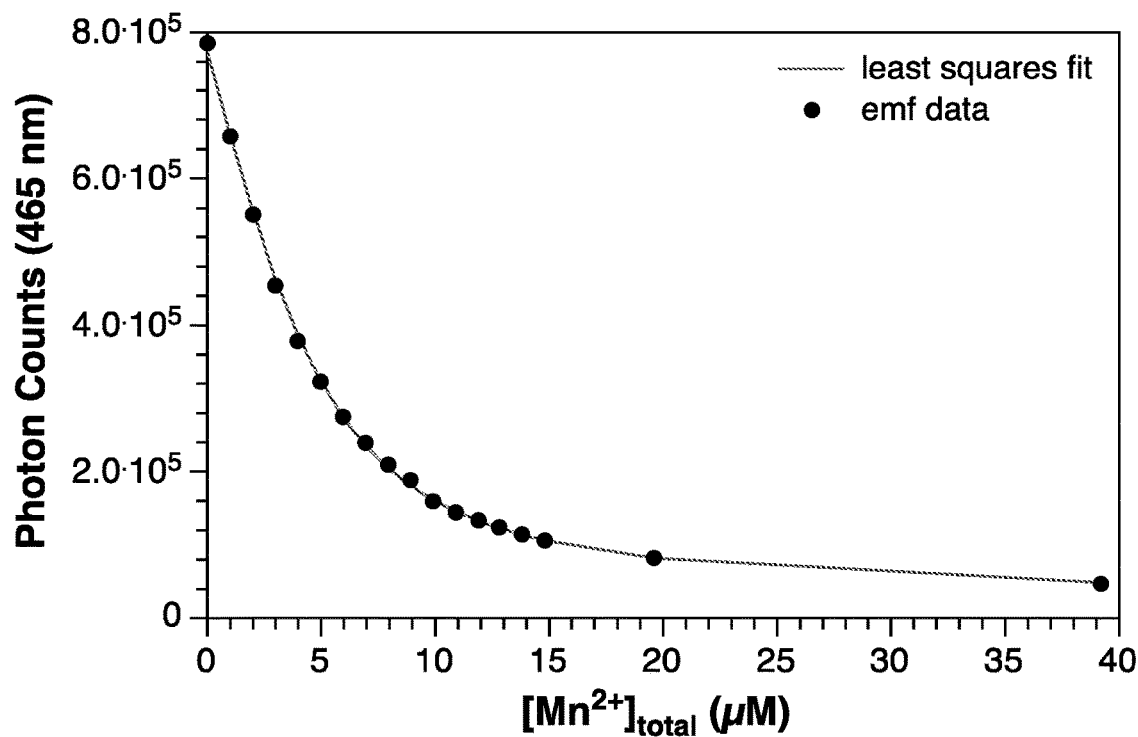

Fluorimetric determination of the Mn(II) stability constant of chromis-2 (4, 5 μM) via a metal-addition titration (FIG. 22A-22B). Fluorimetric titration of chromis-2 with MnSO4.H2O in pH 7.0 aqueous buffer (10 mM PIPES, 0.1 M KCl, 25° C.) (FIG. 22A). The red trace represents free chromis-2 before addition of Mn(II). Non-linear least-squares fitting of the absorbance data, showing the change in fluorescence and corresponding fit at 465 nm. Fitting the absorbance data over the entire spectral window (250-500 nm) yielded an average Log $K_{Zn(II)L}$=7.97±0.03 (n=2) (FIG. 22B).

Figure 23A:
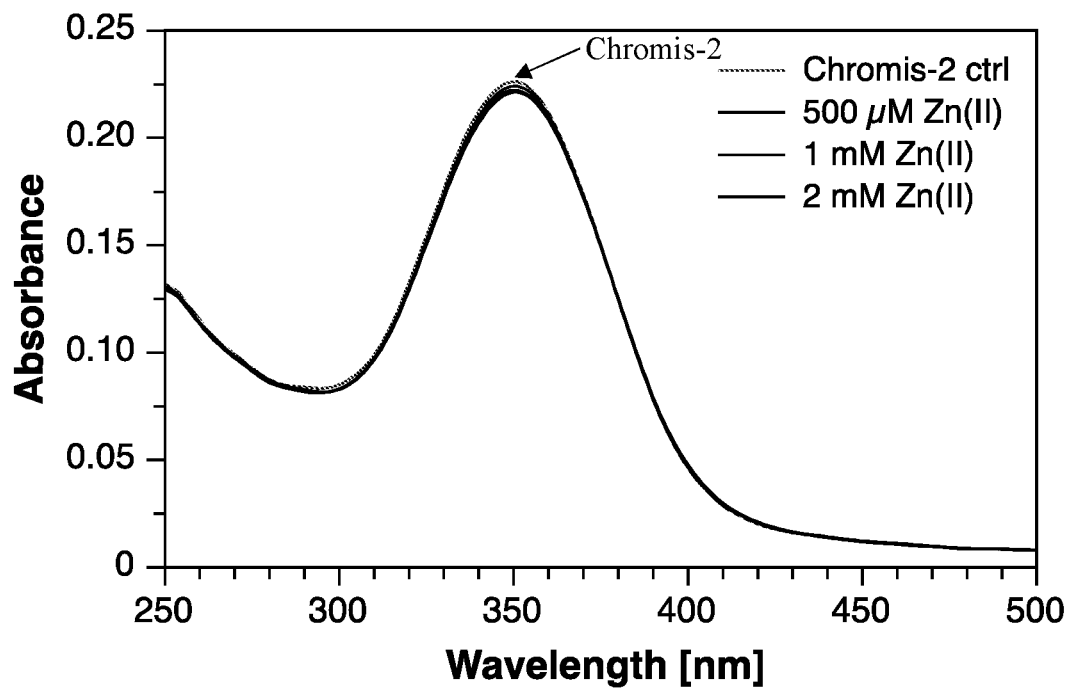
FIG. 23A-23B. Spectrophotometric (FIG. 23A) and fluorimetric (FIG. 23B) titration of chromis-2 ctrl (compound 4a) with Zn(II) from 500 μm to 2 mM in pH 7.0 buffer (10 mM PIPES, 0.1 M KCl, 25° C.). The red trace presents chromis-2 ctrl (4a) (10 μm) before addition of Zn(II). Excitation: 350 nm.
Figure 23B:
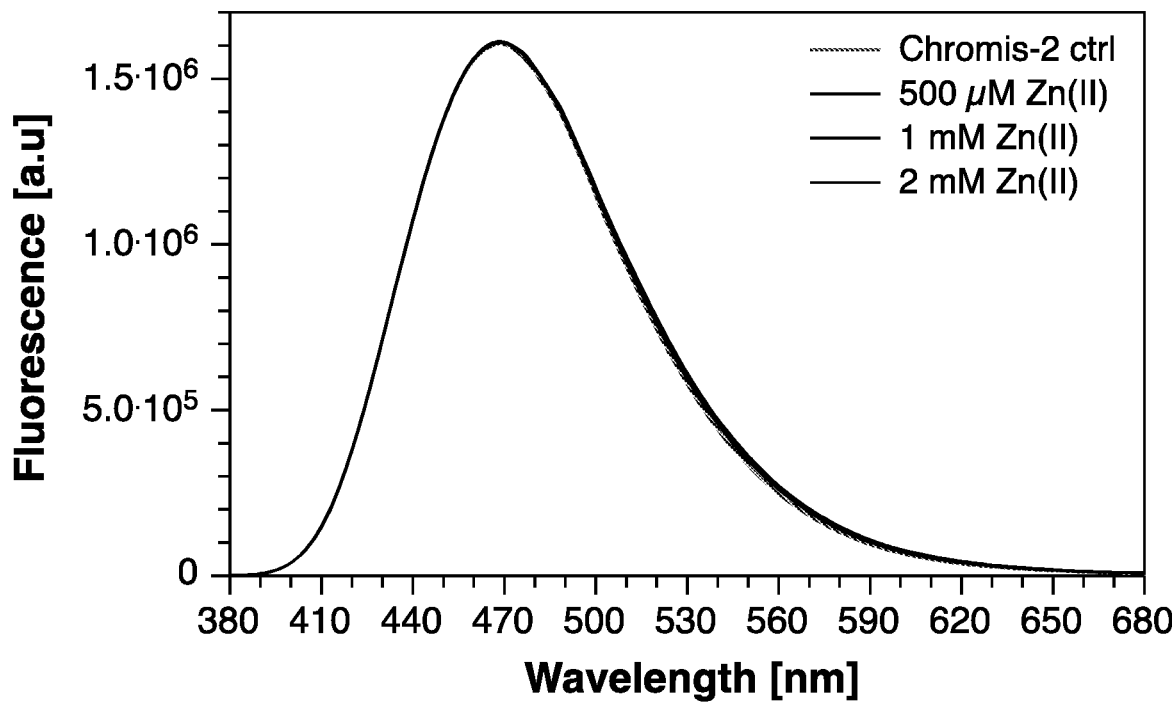

Determination of the Effect of Zn(11) Binding to Chromis-2 Ctrl (4a). The effect of Zn(II) binding to chromis-2 ctrl (compound 4a) was determined by a tandem fluorimetric and spectrophotometric titration. A 10 μM solution of chromis-2 (from a 3 mM stock solution in DMSO) was equilibrated in 3.00 mL of aqueous buffer (10 mM PIPES, 0.1 M KCl, pH 7.0, filtered through a 0.2 μM filter) at 25° C. in a quartz cuvette with a 1-cm pathlength. Both a fluorescence spectrum over the spectral window of 380-700 nm with excitation at 361 nm (FIG. 23A) and an absorbance spectrum over the spectral window of 250-500 nm (FIG. 23B) were acquired. The probe solution was supplemented with $ZnSO_4.7H_2O$ (from a 500 mM stock solution in analytical-grade $H_2O$) from 0.5-2 mM, and after the addition of each aliquot of $ZnSO_4.7H_2O$, the solution was equilibrated by magnetic stirring for 5 minutes, and fluorescence and absorbance spectra were acquired.

Example 5: Ratiometric Imaging of Dynamic Fluxes of Labile Zn(II) in Live Cells

Figure 25:
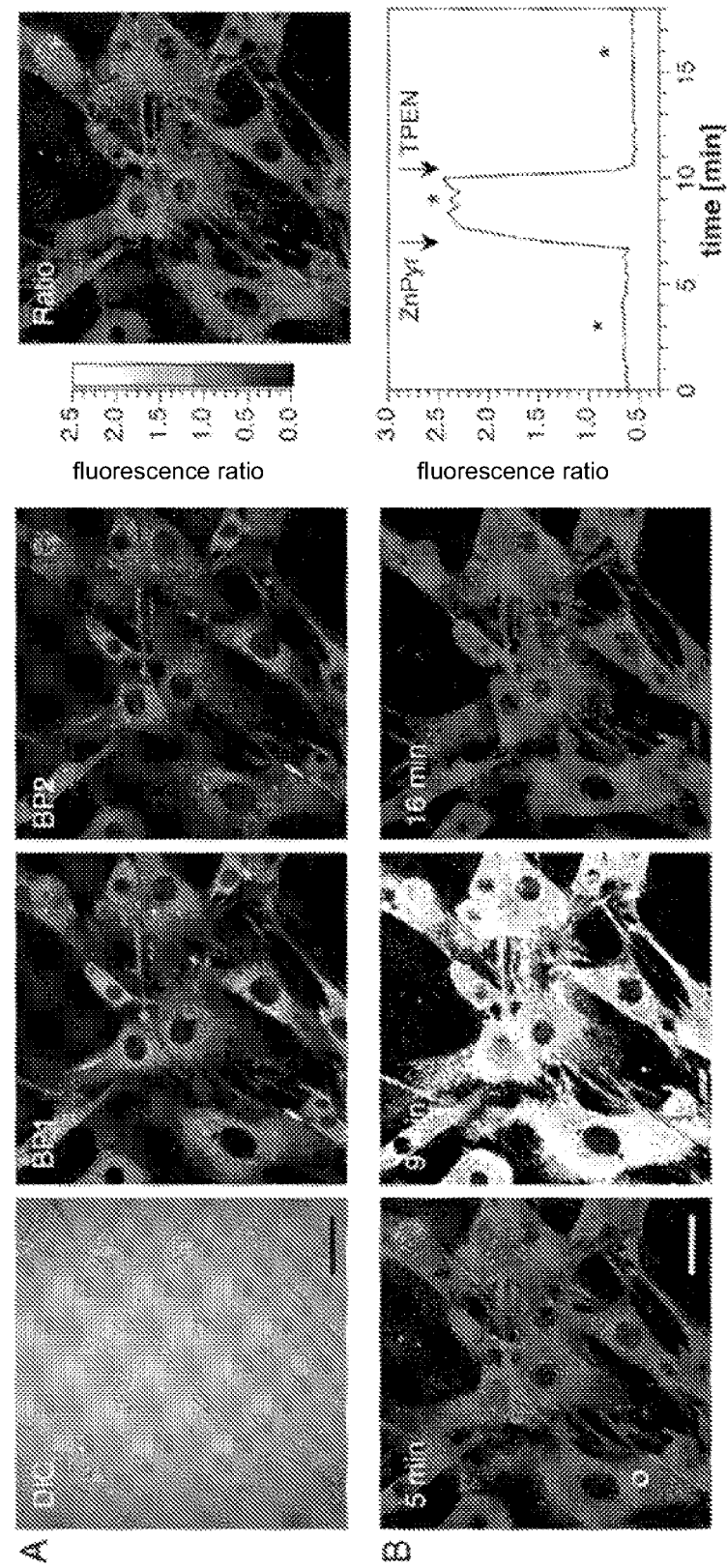
FIG. 25A-25B. Ratiometric imaging of labile Zn(II) pools in live NIH 3T3 mouse fibroblasts with chromis-2 by TPEM (excitation at 720 nm).

To evaluate the Zn(II)-dependent ratiometric response of chromis-2 within the chemical complexity of a live cell, we performed a perfusion experiment with NIH 3T3 mouse fibroblasts as model system (FIG. 25). To this end, fibroblast cells were cultured in Dulbecco's modified Eagle's medium (DMEM, Lonza) supplemented with 10% bovine serum (Gemini), penicillin/streptomycin (50 IU/mL), 200 μM L-glutamine, and 100 μM sodium pyruvate at 37° C. under an atmosphere of humidified air containing 5% $CO_2$. For imaging experiments, cells were grown to 70% confluency on MatTek glass bottom culture dishes pre-coated with poly-L-lysine using phenol red-free DMEM (10% bovine serum, 50 IU/mL penicillin/streptomycin, 200 μM L-glutamine, and 100 μM sodium pyruvate). After replacing the growth medium with serum-free DMEM containing chromis-2 (10 μM), cells were incubation for 30 minutes at 37° C. (5% $CO_2$ atmosphere), and the incubation solution was again replaced with pre-warmed full media. Cells were imaged in an atmospheric chamber at 37° C., 8% humidity, and 5% $CO_2$ using a Zeiss LSM confocal NLO 710 microscope equipped with a femtosecond pulsed Ti:sapphire laser. Scanning fluorescence micrographs were acquired with excitation at 720 nm, and the integrated emission intensity was simultaneously collected through two band pass filters between 425-462 nm and 478-540 nm. The corresponding ratio-images were derived with ImageJ based on the integrated photon counts on a pixel-per-pixel basis (FIG. 25A, right). As evident from the intensity images (FIG. 25A, middle), chromis-2 readily entered cells to yield bright fluorescence throughout the cytoplasm but was excluded from cell nuclei. Although the fluorescence intensity distribution appears uneven, including distinct punctate localizations, the corresponding ratio-image indicates a rather even fractional saturation with an average ratio R of 0.64±0.2. Upon exposure to a mixture of $ZnSO_4$ and pyrithione, a membrane-permeable ionophore for Zn(II), the intensity ratio rapidly increased by more than 4-fold to R=2.36±0.6, indicating saturation of the probe with Zn(II) (FIG. 25B). Addition of the membrane-permeant high-affinity chelator TPEN (N,N,N',N'-tetrakis(2-pyridylmethyl)ethylenediamine, apparent $K_d$=9.3 fM at pH 7.0) elicited a ratio response towards a slightly lower R value of 0.55±0.2 compared to the initial conditions. A plot of the intensity ratio vs. time revealed a rapid dynamics for Zn(II)-binding and release, both of which occurred within a few seconds (FIG. 25B, right).

Example 6: Compounds, I, II, III—Synthesis and Characterization

The effect of increasing the pi-conjugation length or donor strength with regard to the excitation wavelength was shown.

Structures of Compounds I, II, and III. Compounds I, II, and III have the following structures:

Compound I

Compound II

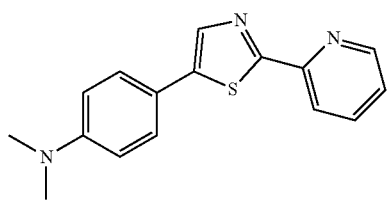

Compound III

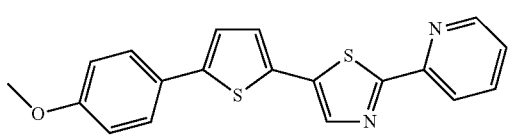

Synthesis of Compounds II and III. Compounds II and III were synthesized starting from picolinic acid and the corresponding ketone-derivative as outlined for the synthesis of chromis-2.

Compound II: $^1$H NMR (CDCl$_3$, 400 MHz) δ 3.00 (s, 6H), 6.74 (d, J=8.9 Hz, 2H), 7.28 (t, J=8.5 Hz, 1H), 7.82 (d, J=8.9 Hz, 2H), 7.77 (dt, J=7.7, 1.6 Hz, 1H), 7.94 (s, 1H), 8.16 (d, J=8.0 Hz, 1H), 8.60 (d, J=5.3 Hz, 1H). $^{13}$C NMR (CDCl$_3$, 100 MHz) δ 40.5, 112.6, 119.4, 124.0, 127.8, 137.0, 137.6, 142.8, 149.5, 150.6, 151.9, 165.8.

Compound III: $^1$H NMR (CDCl$_3$, 400 MHz) δ 3.85 (s, 3H), 6.93 (d, J=8.7 Hz, 2H), 7.15 (d, J=3.8 Hz, 1H), 7.21 (d, J=3.8 Hz, 1H), 7.32 (t, J=6.7 Hz, 1H), 7.54 (d, J=8.7 Hz, 2H), 7.80 (t, J=7.6 Hz, 1H), 7.95 (s, 1H), 8.17 (d, J=7.9 Hz, 1H), 8.62 (d, J=4.4 Hz, 1H). $^{13}$C NMR (CDCl$_3$, 100 MHz) δ 55.5, 114.6, 119.6, 123.0, 124.5, 126.7, 127.0, 127.2, 131.7, 135.3, 137.2, 139.5, 144.9, 149.6, 151.5, 159.7, 167.1.

Figure 26:
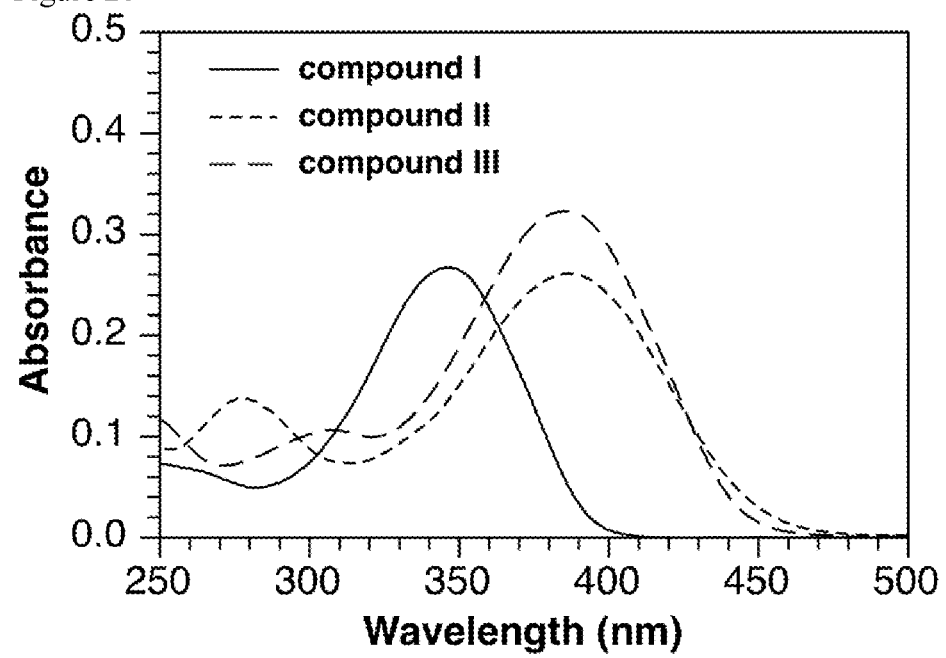
FIG. 26: UV-vis absorption spectra of compounds I, I, III in methanol at 298 K.

UV-vis Spectral Characterization of Compounds I, II, and III. FIG. 26 shows UV-vis absorption spectra of compounds I, I, III in methanol at 298 K. Both the increased donor strength of the dimethyl amino group in compound II or extension of the pi-bridge length in compound III elicit a red-shifted absorption spectrum. Compounds II and II demonstrate the effect of increasing the pi-conjugation length or donor strength with regard to the excitation wavelength and the red-shift associated therewith.

The invention claimed is:
1. A compound according to Formula I:

Formula I

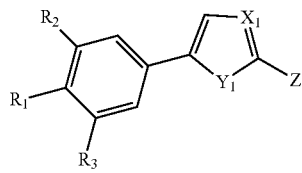

wherein Z is

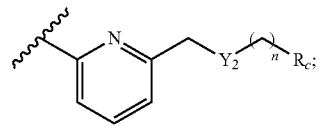

Y$_1$ is selected from —NR$_4$— and —S—;
Y$_2$ is selected from —NR$_5$—, —S—, and —O—;
R$_c$ is Ar, —OR$_4$, or —N((CH$_2$)$_q$—Ar)$_2$;
R$_1$ is selected from hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroalkyl, substituted or unsubstituted heteroalkenyl, substituted or unsubstituted heteroalkynyl, substituted or unsubstituted heterocycloalkyl, substituted or unsubstituted heterocycloalkenyl, substituted or unsubstituted heteroaryl, —OCH$_3$, —OCH$_2$COOR$_9$, —OCH$_2$CH$_2$COOR$_9$, —OCH$_2$CH$_2$CH$_2$SO$_2$R$_9$, —NH$_2$, —NHR$_9$, and —N(R$_9$)$_2$; R$_2$ is selected from hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroalkyl, substituted or unsubstituted heteroalkenyl, substituted or unsubstituted heteroalkynyl, substituted or unsubstituted heterocycloalkyl, substituted or unsubstituted heterocycloalkenyl, and substituted or unsubstituted heteroaryl; or in the alternative, R$_1$ and R$_2$ join together to form a moiety selected from substituted or unsubstituted cycloalkyl, substituted or unsubstituted cycloalkenyl, substituted or unsubstituted aryl, substituted or unsubstituted heterocycloalkyl, substituted or unsubstituted heterocycloalkenyl, and substituted or unsubstituted heteroaryl;

R$_3$ and R$_4$ are each independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroalkyl, substituted or unsubstituted heteroalkenyl, substituted or unsubstituted heteroalkynyl, substituted or unsubstituted heterocycloalkyl, substituted or unsubstituted heterocycloalkenyl, and substituted or unsubstituted heteroaryl;

R$_5$ is selected from C$_{1-3}$-alkyl optionally substituted with —OR$_4$ or Ar;

R$_9$ is selected from —CH$_3$, —C$_2$H$_5$, substituted or unsubstituted heteroalkyl, substituted or unsubstituted heteroalkenyl, substituted or unsubstituted heteroalkynyl, and substituted or unsubstituted heteroaryl;

n is 1, 2, or 3;
q is 1, 2, or 3;
Ar is independently at each occurrence a substituted or unsubstituted six-membered heteroaryl selected from:

61

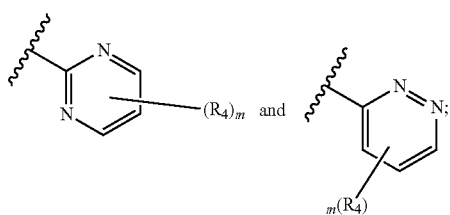

and m is any integer from 0 to 3.

2. The compound of claim 1, wherein:

Z is selected from:

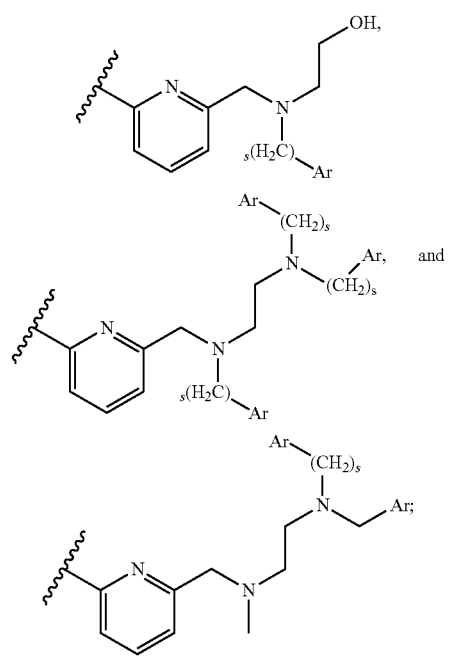

and s is 1, 2, or 3.

3. The compound of claim 1, wherein:

Z is selected from:

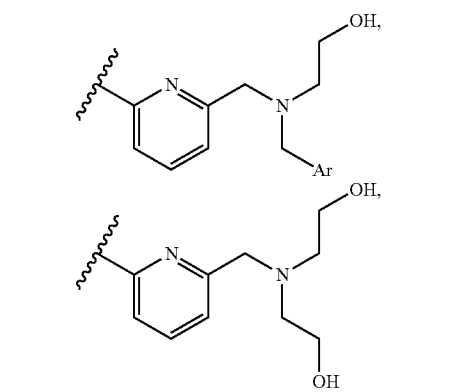

62

-continued

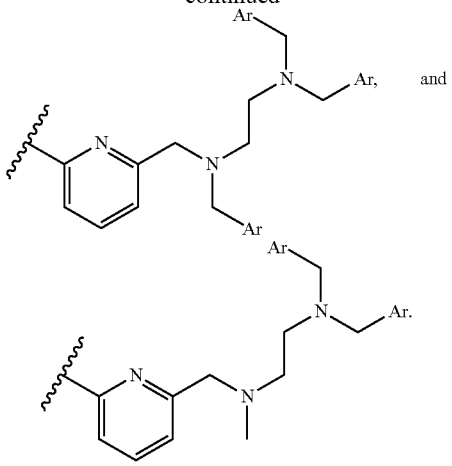

4. The compound of claim 1, wherein Ar is the same at each occurrence.

5. A compound according to the following formula:

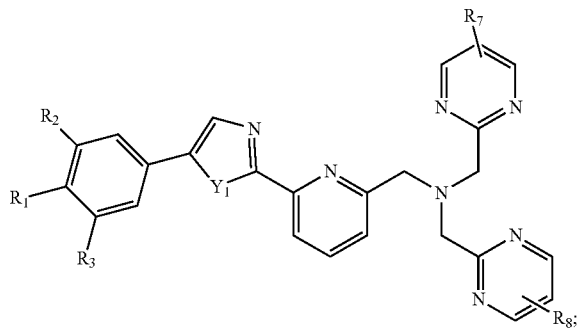

wherein:

$Y_1$ is selected from —$NR_4$— and —S—;

$R_1$ is selected from hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroalkyl, substituted or unsubstituted heteroalkenyl, substituted or unsubstituted heteroalkynyl, substituted or unsubstituted heterocycloalkyl, substituted or unsubstituted heterocycloalkenyl, substituted or unsubstituted heteroaryl, —$OCH_3$, —$OCH_2COOR_9$, —$OCH_2CH_2COOR_9$, —$OCH_2CH_2CH_2SO_2R_9$, —$NH_2$, —$NHR_9$, and —$N(R_9)_2$; $R_2$ is selected from hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroalkyl, substituted or unsubstituted heteroalkenyl, substituted or unsubstituted heteroalkynyl, substituted or unsubstituted heterocycloalkyl, substituted or unsubstituted heterocycloalkenyl, and substituted or unsubstituted heteroaryl; or in the alternative, $R_1$ and $R_2$ join together to form a moiety selected from substituted or unsubstituted cycloalkyl, substituted or unsubstituted cycloalkenyl, substituted or unsubstituted aryl, substituted or unsubstituted heterocycloalkyl, substituted or unsubstituted heterocycloalkenyl, and substituted or unsubstituted heteroaryl;

R₃ and R₄ are each independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroalkyl, substituted or unsubstituted heteroalkenyl, substituted or unsubstituted heteroalkynyl, substituted or unsubstituted heterocycloalkyl, substituted or unsubstituted heterocycloalkenyl, and substituted or unsubstituted heteroaryl;

R₇ and R₈ are each independently selected from —H, —CH₃, —OR₄, —CF₃, —F, —Cl, —CN, —COOR₄, and —SO₂R₄; and R₉ is selected from —CH₃, —C₂H₅, substituted or unsubstituted heteroalkyl, substituted or unsubstituted heteroalkenyl, substituted or unsubstituted heteroalkynyl, and substituted or unsubstituted heteroaryl.

6. A compound having a formula selected from:

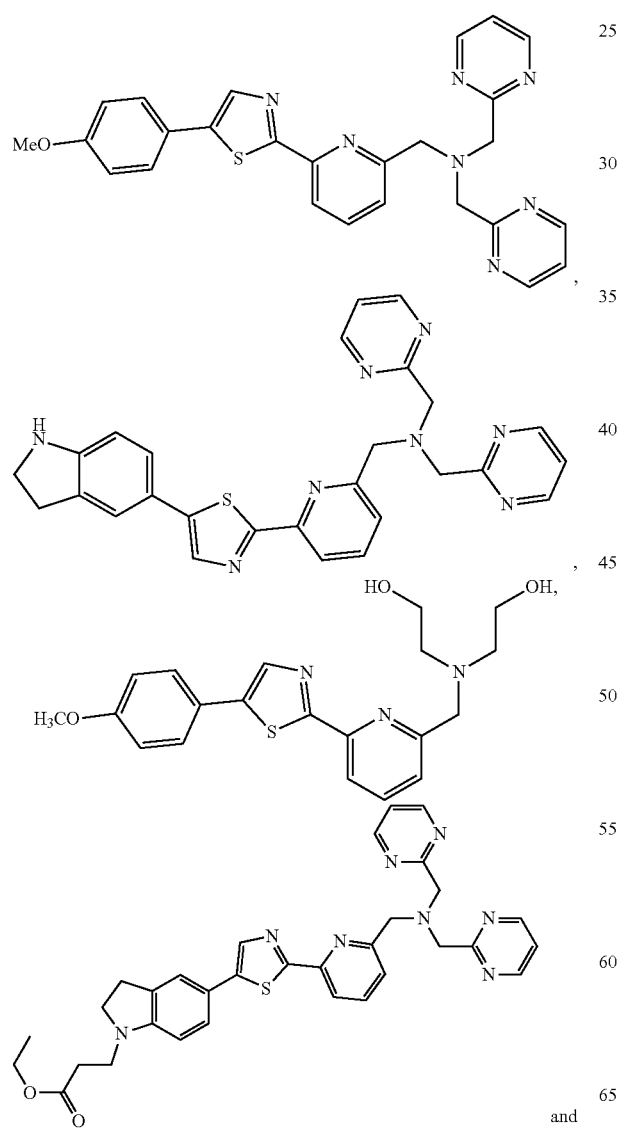

7. A compound having a formula selected from:

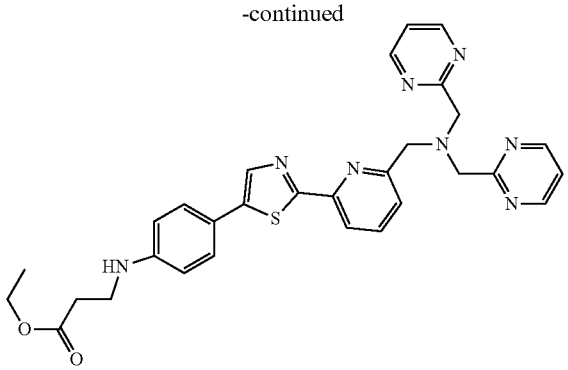

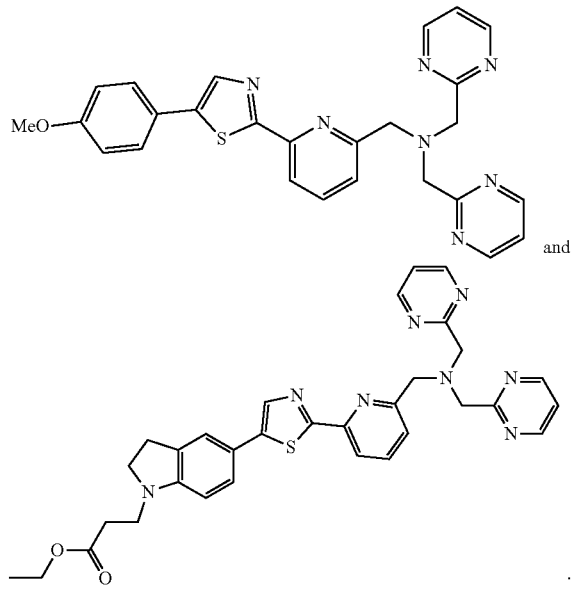

8. A fluorescent complex comprising the compound of claim 1 and zinc(II) in a 1:1 stoichiometric ratio.

9. The fluorescent complex of claim 8, wherein the fluorescent complex further comprises a ligand.

10. The fluorescent complex of claim 8, wherein a maximum absorption wavelength of the fluorescent complex is from about 15 nm to about 50 nm greater than a maximum absorption wavelength of the compound of Formula I.

11. The fluorescent complex of claim 8, wherein a maximum emission wavelength of the fluorescent complex is from about 40 nm to about 60 nm greater than a maximum emission wavelength of the compound of Formula I.

12. A method of detecting zinc in a sample comprising:
treating the sample with the compound according to claim 1,
detecting a first wavelength emission intensity of the sample at a first wavelength and a second wavelength emission intensity of the sample at a second wavelength, wherein the first wavelength emission intensity is associated with the compound not being bonded to zinc and the second wavelength emission intensity is associated with the compound being bonded to zinc; and
comparing the first wavelength emission intensity to the second wavelength emission intensity to determine the concentration of zinc in the sample.

13. The method of claim 12, wherein the first wavelength is from about 380 nm to about 700 nm;
wherein the second wavelength is about 40 nm to about 80 nm greater than the first wavelength; and
wherein the sample is a biological sample.

14. A method of detecting zinc in a sample comprising:
treating a sample with the compound according to claim 7;
detecting a first wavelength emission intensity of the sample at a first wavelength and a second wavelength emission intensity of the sample at a second wavelength, wherein the first wavelength emission intensity is associated with the compound not being bonded to zinc and the second wavelength emission intensity is associated with the compound being bonded to zinc; and
detecting zinc in the sample by comparing the first wavelength emission intensity to the second wavelength emission intensity.

15. The method according to claim 14 further comprising determining the concentration of zinc in the sample.

\* \* \* \* \*

UNITED STATES PATENT AND TRADEMARK OFFICE
CERTIFICATE OF CORRECTION

PATENT NO. : 11,604,141 B2
APPLICATION NO. : 16/619620
DATED : March 14, 2023
INVENTOR(S) : Fahrni et al.

It is certified that error appears in the above-identified patent and that said Letters Patent is hereby corrected as shown below:

In the Claims

Claim 1, Column 59, Line 60, replace "$X_1$" with "N" in Formula I.

Signed and Sealed this
Fifth Day of November, 2024

Katherine Kelly Vidal
*Director of the United States Patent and Trademark Office*